United States Patent
Gong et al.

(10) Patent No.: US 7,368,575 B2
(45) Date of Patent: *May 6, 2008

(54) 6-ALKYLAMINO-2,2'-DISUBSTITUTED-7,8-DISUBSTITUTED-2H-1-BENZOPYRAN DERIVATIVES AS 5-LIPOXYGENASE INHIBITOR

(75) Inventors: Young-Dae Gong, Daejeon (KR); Hyae-Gyeong Cheon, Daejeon (KR); Young-Sik Cho, Daejeon (KR); Jin-Soo Seo, Daejeon (KR); Jong-Yeon Hwang, Jeonrabuk-Do (KR); Ji-Yeon Park, Gyeongsangbuk-do (KR); Sung-Eun Yoo, Chuncheongnam-Do (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 365 days.

This patent is subject to a terminal disclaimer.

(21) Appl. No.: 10/970,046

(22) Filed: Oct. 20, 2004

(65) Prior Publication Data

US 2005/0203145 A1   Sep. 15, 2005

(30) Foreign Application Priority Data

Mar. 10, 2004   (KR) ...................... 10-2004-0016206

(51) Int. Cl.
*C07D 311/00* (2006.01)
*C07D 405/00* (2006.01)

(52) U.S. Cl. .................... 546/282.1; 548/454; 549/60; 549/365; 549/404

(58) Field of Classification Search ................ 549/404, 549/60, 365; 546/282.1; 548/454
See application file for complete search history.

(56) References Cited

U.S. PATENT DOCUMENTS 5,646,308 A   7/1997  Koga et al.
5,696,137 A * 12/1997  Heine et al. ................ 514/322
6,395,909 B1   5/2002  Bell et al.

FOREIGN PATENT DOCUMENTS

JP          176157     *  9/1997
WO     WO87/05020     *  8/1987

* cited by examiner

*Primary Examiner*—Janet L. Andres
*Assistant Examiner*—Raymond Covington
(74) *Attorney, Agent, or Firm*—Peter F. Corless; Edwards Angell Palmer & Dodge LLP

(57) ABSTRACT

When a multi-step process reaction is carried out in a solution, it generally requires several treatments and purification procedures to go through with after the reaction, however, the inventive method for preparing 2,2'-disubstituted-3,4-dihydro-7,8-disubstituted-6-amino benzopyran derivative using a solid-phased synthetic method simplifies the treatment and purification procedures after the reaction, which makes possible to efficiently construct numerous drug-like libraries. In particular, since the inventive method of the present invention comprises the steps of introducing a carbonate linker of formula 2 into Wang resin used as a common solid support (Step 1); synthesizing various benzopyran in a carbamate form of formula 3 as a key intermediate by reacting various amino benzopyran derivatives with the carbamate resin of formula 2 (Step 2); synthesizing 2,2'-disubstituted-3,4-2H-6-substituted benzopyran resin of formula 4 (Step 3); and synthesizing 2,2'-disubstituted-3,4-2H-6-alkylamino benzopyran derivative of formula 1 using a dichloromethane solution containing TFA or an organic solvent containing an organic acid, the inventive method is capable of efficiently synthesizing various 2,2'-disubstituted-3,4-2H-6-alkylamino benzopyran derivatives.

Consequently, the present invention has developed a new technique for constructing 2,2'-disubstituted-3,4-2H-6-alkylamino benzopyran library using a solid-phase parallel synthetic method and makes increased the applicability of combinatorial chemical synthetic method. Further, 2,2'-disubstituted-3,4-2H-6-alkylamino benzopyran derivative prepared by the inventive method has a high inhibitory effect to 5-lipoxygenase (5-LO) activity, and therefore, can be effectively used for developing a new propylactic or therapeutic drug for leukotriene activation-related diseases such as chronic inflammation, rheumatic arthritis, colitis, asthma and psoriasis.

3 Claims, No Drawings

6-ALKYLAMINO-2,2'-DISUBSTITUTED-7,8-DISUBSTITUTED-2H-1-BENZOPYRAN DERIVATIVES AS 5-LIPOXYGENASE INHIBITOR

FIELD OF THE INVENTION

The present invention relates to novel 6-alkylamino-2,2'-disubstituted-7,8-disubstituted-2H-1-benzopyran derivatives, a method for the preparation thereof using a parallel synthetic method which is one of combinatorial chemical synthetic methods, a use of the novel compounds showing a high inhibitory effect to 5-lipoxygenase (5-LO) activity for preventing and treating leukotriene (LTA4, B4, C4, D4) activation-related diseases such as inflammatory diseases, rheumatic arthritis, colitis, asthma and psoriasis.

BACKGROUND OF THE INVENTION

5-Lipoxygenase (hereinafter referred to as 5-LO) is an enzyme involved in an arachidonic acid metabolism which synthesizes leukotriene by acting on the generatation of 5-HPETE from the arachidonic acid. LTB4, the most powerful chemottractant among thus synthesized leukotrienes, is a major cause for inducing several diseases such as chronic inflammation, rheumatic arthritis, allergy, asthma and psoriasis. When the cell content of leukotriene becomes increased, tissue and organ are acutly and chronically damaged by bacterial infection and an endotoxin generated thereby as well as inflammatory cells are activated, which then results in development of inflammatory diseases such as chronic inflammation and rheumatis.

Therefore, by developming a 5-LO inhibitor capable of preventing tissue and organ damages by inhibiting the activiation of inflammatory cells due to the increase in cellular leukotriene, it is made possible to prevent or treat several diseases caused by inflammation.

Since a natural product and synthetic compound having a benzopyran backbone show an antioxidant activity, they have been widely known as a privileged structure for developing a pharmacological therapeutic compound effective for treating nervous diseases, hypertension and diabetes and broadly employed in a medicinal chemistry field. However, there is no report that a compound having a benzopyran moiety as a privileged structure is developed as a therapeutic agent for an inflammatory disease.

Meanwhile, the construction of a benzopyran library having various derivatives using a combinatorial chemical synthetic method can be effectively used for screening a hit compound and lead compound at the early stage of a new drug development.

Particularly, it is very important to efficiently construct a large and focused library of small organic molecule, which is capable of introducing various derivatives within a molecule and does not significantly deviate from the range of Rule of 5 by Lipinsky, by using a combinatorial chemical synthetic method for securing molecular variety effective for the screening of a lead compound.

A combinatorial chemistry is a new synthetic thechnique for developing a new compound. While the conventional organic synthetic techniques can synthesize one kind of compound via a single reaction, the combinatorial chemical synthetic technique is highly efficient which can synthesize more various and numerous compounds at the same time or automatize the multi-step synthetic process. It has been easier to screen a hit compound and lead compound having a new structure and optimize their structure and activity due to the introduction of the combinatorial chemical synthetic method.

Further, the combinatorial chemical synthetic method carries out most reaction procedures on a solid support, which makes possible to automatize a successive multi-step reaction (and reaction procedure), and is capable of performing a high throughput screening (HTS) because it is very simple to purify final products.

Although the combinatorial chemical synthetic method solves the uneconomical and unefficient problems of the conventional synthetic methods, there are several reasons why this method does not be easily applied to an organic synthetic field. One representative reason among them is to cause an undesirable side-reaction because most chemical reactions carried on a solid support and used the excessive amount of reaction agents, and the other is to limit an employable solvent depending on the physical property of solid support, which makes narrow the range of chemical reaction to be selected. It has been widely employed Merrifield resin and Wang resin as the solid support in the combinatorial chemical synthesis. Since these solid supports show a significantly low swelling effect in high polar solvents such as alcohols and water, it is very restricted to select a solvent nessesary for the reaction. Accordingly, in order to synthesize various derivatives using solid-phase reaction, there is a need of selecting a solid support and linker, the examination of a reagent and reaction condition, and the selection of substituent group capable of diversly changing the chemical structure and physical property of a target compound. Consequently, for the construction of a target compound library using solid-phase synthesis, it has to be efficiently developed a reaction condition suitable for the characteristics of a target compound and a treatment procedure after a reaction.

The present inventors have found that 6-alkylamino benzopyran derivative significantly inhibits 5-LO activity. Further, the present inventors have endeavored to develop an optimized technique for screening a lead compound by constructing a library of 6-alkylamino benzopyran derivatives on solid-phase using a combinatorial chemical synthetic method. As a result, the conventional chemical reaction on solution-phase synthesizes a target compound by carrying out each reaction step for introducing a subtituent group, a purification step after the reaction and a structural confirmation test, while in oreder to synthesize a target compound library having various substituents using a solid-phase parallel synthesis, the present inventors have performed several reactions at the same time and an efficient treatment procedure after the reaction, to economically produce 6-alkylamino-2,2-disubstituted-7,8-disubstituted-2H-1-benzopyran library in a short period with high yields.

SUMMARY OF THE INVENTION

Accordingly, an object of the present invention is to provide 6-alkylamino-2,2'-disubstituted-7,8-disubstituted-2H-1-benzopyran derivative having a novel structure.

Another object of the present invention is to provide a method for preparing 6-alkylamino-2,2'-disubstituted-7,8-disubstituted-2H-1-benzopyran derivative using a solid-phase parallel synthetic method which can easily analyze the chemical structure of a final product via an automatic reaction procedure and purification step and show high yields.

Another object of the present invention is to provide a use of 6-alkylamino-2,2'-disubstituted-7,8-disubstituted-2H-1- benzopyran derivative showing a high inhibitory effect to 5-lipoxygenase (5-LO) activity for preventing and treating various inflammatory diseases caused by an inflammatory cell activation due to an increase of cellular leukotriene such as chronic inflammation, rheumatism and arthritis.

DETAILED DESCRIPTION OF THE INVENTION

In accordance with one aspect of the present invention, there are provided 6-alkylamino-2,2'-disubstituted-7,8-disubstituted-2H-1-benzopyran derivative having a novel structure and a method for the preparation thereof.

The present invention is characterized by 6-alkylamino-2,2'-disubstituted-7,8-disubstituted-2H-1-benzopyran derivative of formula 1.

<Formula 1>

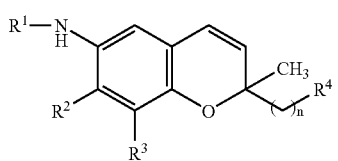

wherein $R^1$ is $C_1 \sim C_{10}$ alkyl, benzyl or substituted benzyl, phenethyl, 2-pyridinylmethyl, 2-thiophenemethyl, 5-methyl-2-thiophenemethyl, 3-thiophenemethyl, indolylmethyl, benzodioxoranylmethyl, naphtalenylmethyl, or furanylmethyl;

$R^2$ and $R^3$ are hydrogen, $C_1 \sim C_5$ alkyl, halogen, or phenyl and substituted phenyl, respectively;

$R^4$ is 5~7 membered heterocycle containing a heteroatom selected from the group consisting of $C_1 \sim C_{10}$ alkyl, phenyl or substituted phenyl, or oxygen and sulfur; and the phenyl or heterocycle is substituted with 1~4 substituents selected from the group consisting of $C_1 \sim C_6$ alkyl, $C_1 \sim C_6$ haloalkyl, halogen, nitro, cyano and $C_1 \sim C_6$ alkoxy, n is an integer ranging from 1 to 5.

Meanwhile, since 6-alkylamino-2,2'-disubstituted-7,8-disubstituted-2H-1-benzopyran derivative of formula 1 has a chiral carbon, the present invention also includes a racemic compound or each isomeric compound isolated by a conventional method and a mixture thereof in the scope of the invention.

Hereinafter, the present invention is described in detail.

The present invention is characterized by 6-alkylamino-2,2'-disubstituted-7,8-disubstituted-2H-1-benzopyran derivative of formula 1; a method for the preparation thereof using a combinatorial chemical synthetic method which can efficiently synthesize the novel benzopyran derivative using solid-phase parallel synthetic method rather than solution-phase chemical reaction; and a use of the novel compound for preventing and treating diseases caused by an inflammatory cell activation due to an increase of cellular leukotriene.

The method for preparing 6-alkylamino-2,2'-disubstituted-7,8-disubstituted-2H-1-benzopyran derivative of formula 1 using a combinatorial chemistry according to the present invention is described in Scheme 1 as follows.

<Scheme 1>

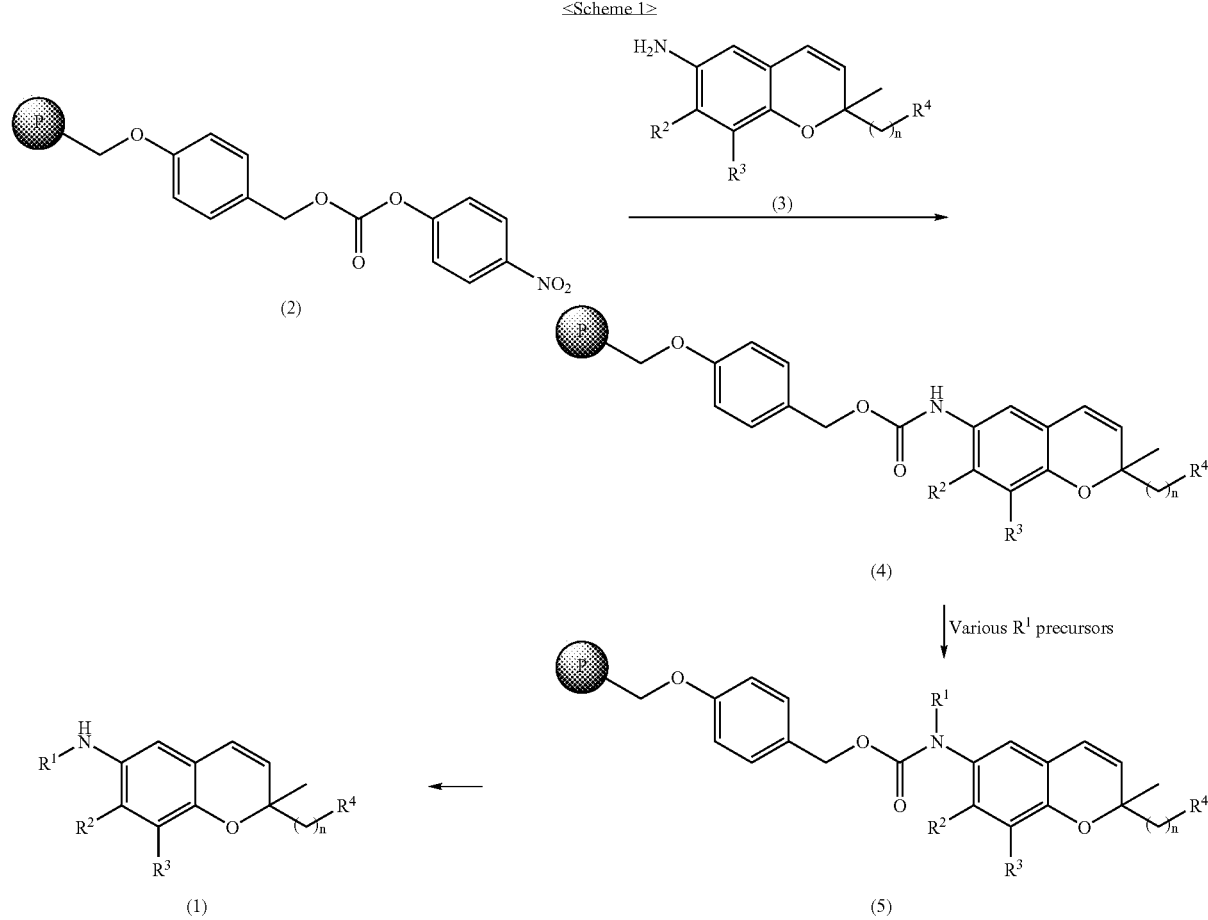

wherein $R^1$, $R^2$, $R^3$, $R^4$ and n are the same as described in Formula 1;

Ⓟ is a solid support in a form of high molecular weight polymer selected from the group consisting of polystyrene-divinylbenzen, methacrylic acid-dimethylacrylamide and hydroxyl methacrylic acid.

2,2'-disubstituted-7,8-disubstituted-2H-1-benzopyran-6-carbamate resin of formula 4 and 6-alkylamino-2,2'-disubstituted-7,8-disubstituted-2H-1-benzopyran resin of formula 5 prepared as a reaction intermediate in the inventive method are also an optical isomer, and therefore, it is possible to isolate them as an isomeric compound, recpectively, as occasion demans.

The inventive method of Scheme 1 comprises the following steps of:

synthesizing carbamate resin in a form of 6-amino-2,2'-disubstituted-7,8-disubstituted-2H-1-benzopyran of formula 4 by incorporating 6-amino-2,2'-disubstituted-7,8-disubstituted-2H-1-benzopyran of formula 3 into the solid support coupled with a carbonate linker of formula 2 (Step 1);

synthesizing resin in a form of 6-alkylamino-2,2'-disubstituted-7,8-disubstituted-2H-1-benzopyran of formula 5 by selectively incorporating $R^1$ substituent into a nitrogen atom of the benzopyran coupled with the carbamate linker of formula 4 (Step 2); and synthesizing 6-alkylamino-2,2'-disubstituted-7,8-disubstituted-2H-1-benzopyran derivative of formula 1 by deprotecting the compound of formula 5 with a dichloromethane solution containing trifluoroacetate (TFA) or an organic solvent containing an organic acid (Step 3).

According to the preferred embodiment of the present invention, when N-alkylation using the benzopyran resin in a form of carbamate on the solid support of formula 4 is carried out via a parallel synthetic method, it is capable of conducting numerous reaction and purification steps at the same time, which makes possible to synthesize various 6-alkylamino-2,2'-disubstituted-7,8-disubstituted-2H-1-benzopyran derivatives in a short period.

The preferred ranges of reaction procedure, solvent system composition and reaction condition in the inventive method are descrived in detail as follows.

The present invention employes an organic solvent which shows a high swelling effect of Wang resin or Merrifield resin.

Dimethylacetamide (DMA) is employed as a solvent in Step 1. It is preferable to employ a base in the amount of about 3 equivalents, and it is more economically preparable to employ the base in the amount of around 2 equivalents. At this time, the base employable in Step 1 of the inventive method includes N,N-diisopropylethylamine (DIPEA) and triethylamine ($Et_3N$).

Dimethylsulfoxide (DMSO) or tetrahydrofuran (THF) is employed as a solvent in Step 2. It it preferable to employ a base and $R^1$ substituent in the amount of about 3 equivalents, respectively, and it is more economically preferable to employ the base and $R^1$ substituent in the amount of aroud 2 equivalents. At this time, the base in Step 2 of the inventive method includes lithium-t-butoxide (LiOtBu), and $R^1$ substituent, alkyl halide, benzyl halide, substituted benzyl halide and alkyl halide substituted with a heterocyclic compound.

Step 3 synthesizes 6-alkylamino-2,2'-disubstituted-7,8-disubstituted-2H-1-benzopyran library of formula 1 by conducting a cleavage with a dichloromethane solution containing trifluoroacetic acid (TFA) or an organic solvent containing an organic acid.

Further, to confirm the synthesis of 6-alkylamino-2,2'-disubstituted-7,8-disubstituted-2H-1-benzopyran library of formula 1, a final product is subjected to structural analysis with NMR and Mass spectrum after the target compound cleavaged from 6-alkylamino-2,2'-disubstituted-7,8-disubstituted-2H-1-benzopyran resin of formula 5 in the final step is purified and isolated by a flash column chromatography using a multi-column equipment. Resins of formula 2, 4 and 5, a reaction intermediate, are subjected to measure ATR-FTIR to confirm the progress of reaction.

Meanwhile, the compounds of the present invention show a high inhibitory effect to 5-lipoxygenase (5-LO) activity, and therefore, can be efficiently used for preventing and treating inflammatory diseases caused by activation of leukotriene-relating receptor. Namely, the inventive compounds can be effectively used for developing a new prophylactic or therapeutic drug for rheumatism, asthma and allergy caused by an inflammatory cell activation.

Accordingly, the present invention includes a pharmaceutical composition for preventing and treating various diseases caused by a stimulation of 5-lipoxygenase (5-LO) or an activation of inflammatory cells which comprises 6-alkylamino-2,2'-disubstituted-7,8-disubstituted-2H-1-benzopyran derivative of formula 1 or a pharmaceutically acceptable salt thereof.

The pharmaceutically acceptable salt of the present invention can be prepared by a conventional method well-known in the art. The pharmaceutically acceptable salt includes, but is not limited to, an acidic salt formed by reacting with an inorganic acid such as hydrochloric acid, hydrogen bromide, sulfuric acid, sodium hydrogen sulfate, phosphoric acid and carbonic acid, or an organic acid such as formic acid, acetic acid, oxalic acid, benzoic acid, citric acid, tartaric acid, gluconic acid, gestisic acid, fumaric acid, lactobionic acid, salicylic acid and acetylsalicylic acid (aspirin); or a metal salt formed by reacting with an alkali metal ion such as sodium and potassium; or a form of pharmaceutically acceptable salt formed by reacting with an ammonium ion.

Further, the pharmaceutical composition comprising 6-alkylamino-2,2'-disubstituted-7,8-disubstituted-2H-1-benzopyran derivative of formula 1 or a pharmaceutically acceptable salt thereof may be prepared according to the conventional procedures in the art. In such preparation, it is preferable to mix, dilute or encapsulate the effective ingredient with a suitable carrier in the form of capsule, sachet or other container. Therefore, the composition of the present invention may be prepared as tablets, pills, dispersions, sachet, elixir, suspensions, emulsions, solutions, syrups, aerosols, soft or hard gelatin capsules, injection solutions or suspensions, ointments, creams or lotions.

Pharmaceutically acceptable carriers, excipients and diluents used in the inventive pharmaceutical composition include, are not but limited to, lactose, dextrose, sucrose, sorbitol, manitol, calcium silicate, cellulose, methyl cellulose, microcrystalline cellulose, polyvinylidone, water, methyl hydroxy benzoate, propyl hydroxy benzoate, talc, magnesium stearate and mineral oil. The composition of the present invention may further comprise fillers, anti-coagulants, lubricants, wetting agents, odoriferous substances, emulsifying agents or preservatives. The inventive pharmaceutical composition may be formulated to provide a rapid, continuous or delayed release of the effective ingredient after administering to a mammal according to the conventional procedures in the pharmaceutical field.

The inventive pharmaceutical composition can be administered orally or via parental routes such as percutaneous, subcutaneous, intravenous or intramuscular.

For the purpose of a clinical administration, a typical daily dose of 6-alkylamino-2,2'-disubstituted-7,8-disubstituted-2H-1-benzopyran derivative of formula 1 or a pharmaceutically acceptable salt thereof may range from 0.01 to 1,000 mg/70 kg body weight, and can be administrated in a single dose or in a divided dose. However, it can be changed into the higher or lower daily dose of the effective ingredient depending on a certain disease. Further, it should be understood that the amount of the effective ingredient actually administrated to a certain patient ought to be determined in light of various relevant factors including the kind of effective compound administered, body weight, age, sex, health conditions, diet and excretion rate of an individual patient, the chosen route of administration, the combination of drugs and the severity of the patient's symptom.

The following Examples and Test Examples are given for the purpose of illustration purpose only, and are not intended to limit the scope of the invention.

EXAMPLE

Example I

Synthesis and Confirmation of 6-amino-2,2'-disubstituted-2H-1-benzopyran resin (Formula 4)

(I-1) Synthesis and Confirmation (4-1-1) of 6-amino-2,2-dimethyl-2H-1-benzopyran carbamate resin (4-1)

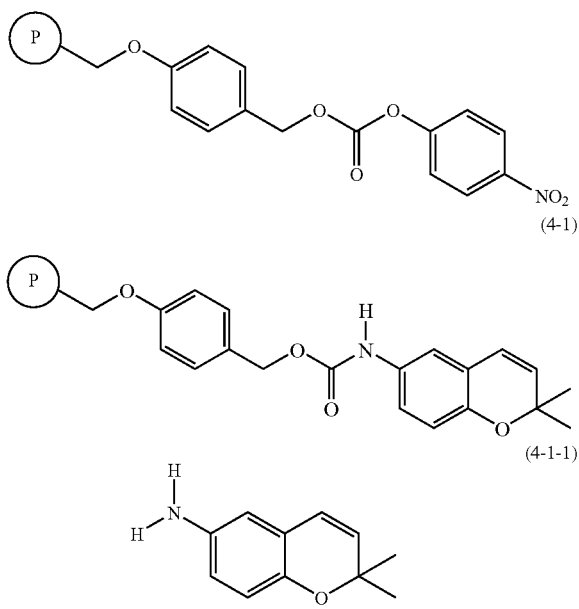

After a carbonate resin (0.80 mmol/g, 10 g, 8.0 mmol) of formula 2 was mixed with dimethylacetamide (DMA, 50 mL) by shaking at room temperature for 10 min, 6-amino-2,2-dimethyl-2H-1-benzopyran (2.80 g, 16.0 mmol) and N,N-diisopropylethylamine (DIPEA; 5.17 mg, 40.0 mmol) were successively added thereto and shaked at 25° C. for 15 hrs. After the reaction was completed, the reaction mixture was subjected to filtration and repeatedly washed with DMF, DCM, DCM/MeOH and MeOH, to obtain a solid resin (Formula 4-1; 11.5 g). (ATR-FTIR; carbamate: 1725 cm$^{-1}$)

To a suspension of the resin (200 mg, 0.16 mmol) of formula 4-1 in DCM (5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain an oil of formula 4-1-1 (19.3 mg, resin 2; yield=68% from loading capacity 0.80 mmol/g).

(I-2) Synthesis and Confirmation (4-4-1) of 2H-6-amino-2-methyl-2-phenethyl-benzopyran carbamate resin (4-4)

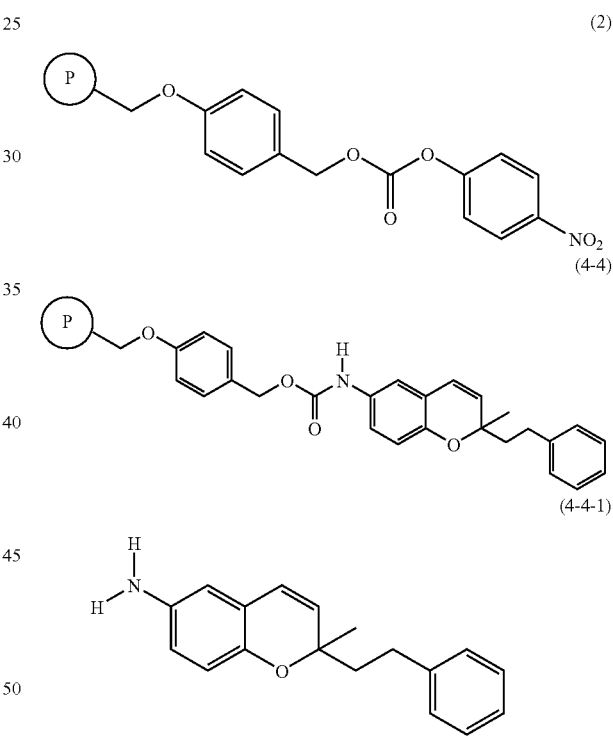

After a carbonate resin (0.80 mmol/g, 10 g, 8.0 mmol) of formula 2 was mixed with dimethylacetamide (DMA, 50 mL) by shaking at room temperature for 10 min, 2H-6-amino-2-methyl-2'-phenethyl-benzopyran (4.25 g, 16.0 mmol) and diisopropylethyl amine (DIPEA; 5.17 mg, 40.0 mmol) were successively added thereto and mixed by shaking at 25° C. for 15 hrs. After the reaction was completed, the reaction mixture was subjected to filtration and repeatedly washed with DMF, MC, MC/MeOH and MeOH, to obtain a solid resin (Formula 4-4; 12.2 g). (ATR-FTIR; carbamate: 1725 cm$^{-1}$)

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain an oil of formula 4-4-1 (26.5 mg, resin 2; yield=63% from loading capacity 0.80 mmol/g).

(I-3) Synthesis and Confirmation (4-7-1) of 2,7-dimethyl-2-ethyl-2H-6-amino benzopyran carbamate resin (4-7)

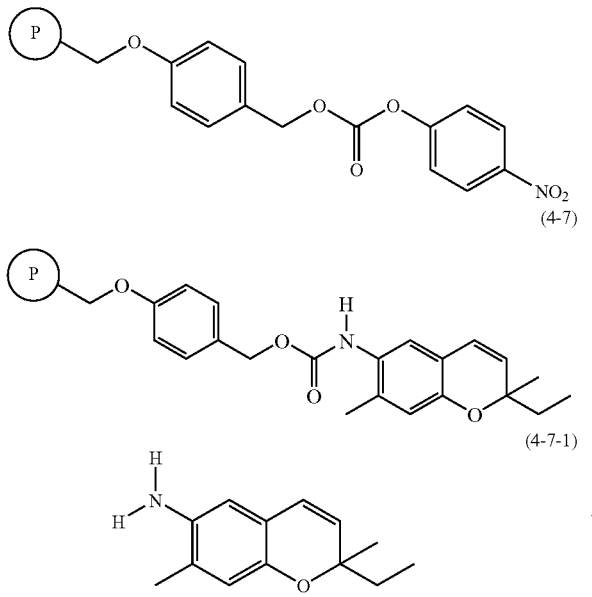

After a carbonate resin (0.80 mmol/g, 10 g, 8.0 mmol) of formula 2 was mixed with dimethylacetamide (DMA, 50 mL) by shaking at room temperature for 10 min, 6-amino-2,7-dimethyl-2'-ethyl-2H-benzopyran (3.25 g, 16.0 mmol) and diisopropylethyl amine (DIPEA; 5.17 mg, 40.0 mmol) were successively added thereto and mixed by shaking at 25° C. for 15 hrs. After the reaction was completed, the reaction mixture was subjected to filtration and repeatedly washed with DMF, DCM, DCM/MeOH and MeOH, to obtain a solid resin (Formula 4-7; 11.7 g). (ATR-FTIR; carbamate: 1725 cm$^{-1}$)

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain an oil of formula 4-7-1 (24.4 mg, resin 2; yield=75% from loading capacity 0.80 mmol/g).

(I-4) Synthesis and Confirmation (4-10-1) of 6-amino-2,2,7-trimethyl-2H-benzopyran carbamate resin (4-10)

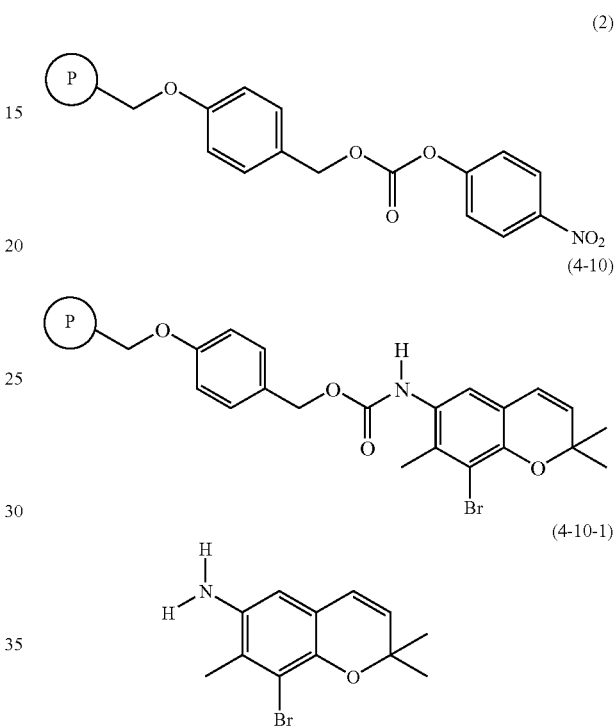

After a carbonate resin (0.80 mmol/g, 10 g, 8.0 mmol) of formula 2 was mixed with dimethylacetamide (DMA, 50 mL) by shaking at room temperature for 10 min, 6-amino-8-bromo-2,2,7-trimethyl-2H-benzopyran (4.29 g, 16.0 mmol) and diisopropylethyl amine (DIPEA; 5.17 mg, 40.0 mmol) were successively added thereto and mixed by shaking at 25° C. for 15 hrs. After the reaction was completed, the reaction mixture was subjected to filtration and repeatedly washed with DMF, DCM, DCM/MeOH and MeOH, to obtain a solid resin (Formula 4-10; 12.2 g). (ATR-FTIR; carbamate: 1725 cm$^{-1}$)

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain an oil of formula 4-10-1 (29.5 mg, resin 2; yield=69% from loading capacity 0.80 mmol/g).

(I-5) Synthesis and Confirmation (4-11-1) of 2H-6-amino-2,2-dimethyl-8-phenyl benzopyran carbamate resin (4-11)

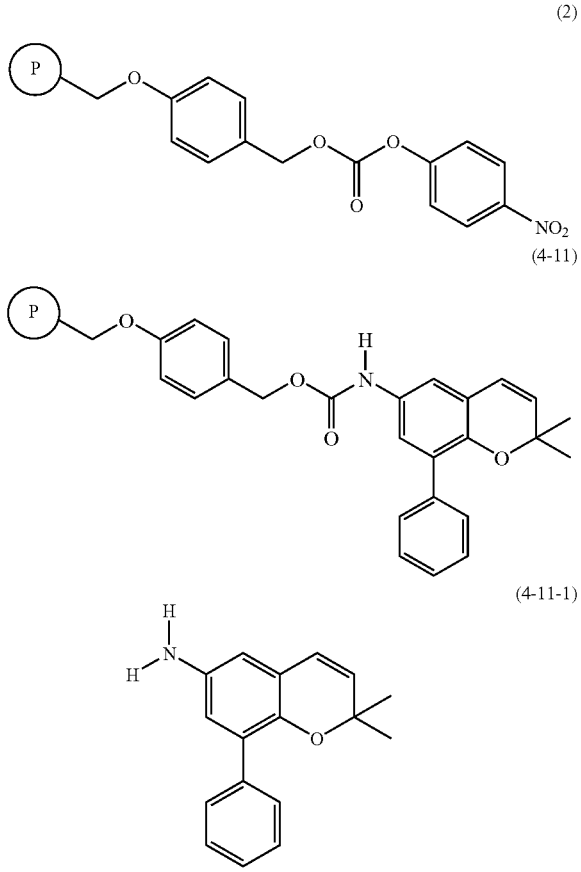

After a carbonate resin (0.80 mmol/g, 10 g, 8.0 mmol) of formula 2 was mixed with dimethylacetamide (DMA, 50 mL) by shaking at room temperature for 10 min. 2,2-dimethyl-8-phenyl-20-6-amindgenzopyran (4.02 g, 16.0 mmol) and diisopropylethyl amine (DIPEA; 5.17 mg, 40.0 mmol) were successively added thereto and mixed by shaking at 25° C. for 15 hrs. After the reaction was completed, the reaction mixture was subjected to filtration and repeatedly washed with DMF, DCM, DCM/MeOH and MeOH, to obtain a solid resin (Formula 4-11; 12.1 g). (ATR-FTIR; carbamate: 1725 cm$^{-1}$)

To a suspension of the resin (200 mg, 0 g0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain an oil of formula 4-11-1 (32.6 mg, resin 2; yield=81.1% from loading capacity 0.80 mmol/g).

Example II

N-alkylation using 2H-6-amino-2,2'-disubstituted benzopyran resin (Formula 4) and Synthesis of a Target Compound (Formula 1)

(II-1) N-benzylation (5-1) and deprotection (1-1) of 2H-6amino-2,2-dimethyl benzopyran resin (4-1)

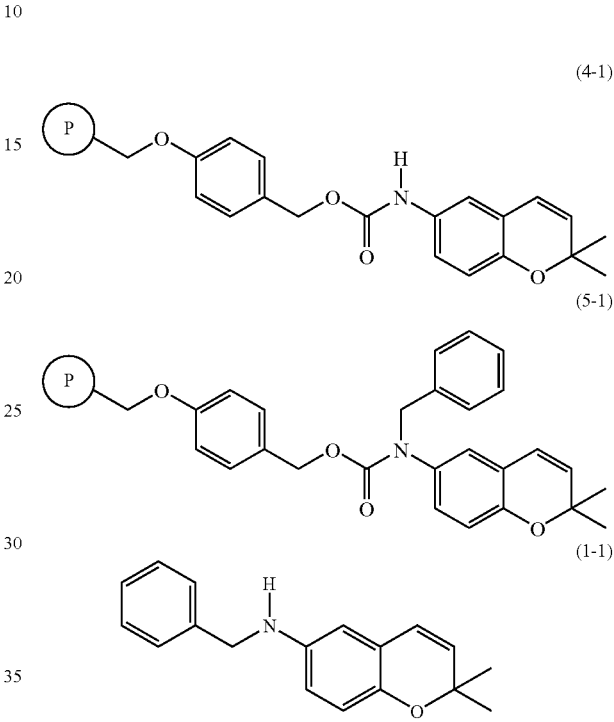

After carbamate resin of formula 4-1 (200.00 mg, 0.11 mmol) in a form of benzopyran was mixed with dimethylsulfoxide (DMSO, 3 mL) by shaking at room temperature for 10 min, 1 M lithium t-butoxide (LiOtBu-; 0.33 mL, 0.33 mmol) dissolved in tetrahydrofuran (THF) was added thereto and mixed by shaking at the same temperature for 20 min. Benzyl bromide (BnBr; 0.039 mL, 0.33 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-1; 203.9 mg). (ATR-FTIR; N-methylation carbamate: 1700 cm$^{-1}$)

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-1 (25.0 mg, resin 4-1; yield=85% from loading capacity 0.55 mmol/g).

$^1$H NMR (300 MHz, CDCl$_3$): δ(ppm) 7.39~7.26 (m, 5H), 6.64 (d, 1H, J=8.5 Hz), 6.45 (dd, 1H, J=8.5 Hz, J=2.8 Hz), 6.33 (d, 1H, J=2.8 Hz), 6.24 (d, 1H, J=9.7 Hz), 5.60 (d, 1H, J=9.7 Hz), 4.27 (s, 2H), 1.39 (s, 6H)

(II-2) N-(4-trifluoromethyl)benzylation (5-25) and deprotection (1-25) of 2H-6amino-2,2-dimethyl benzopyran resin (4-1)

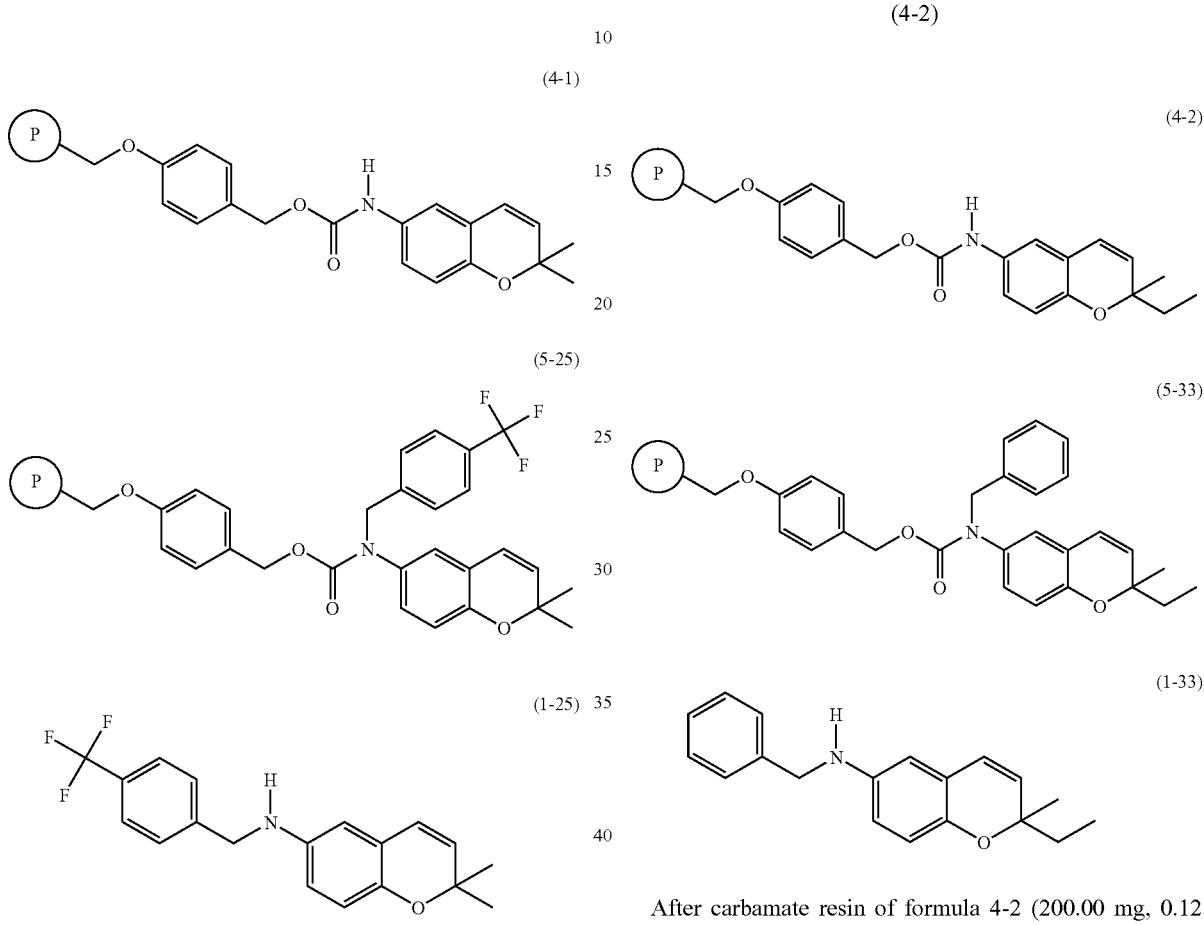

After carbamate resin of formula 4-1 (200.00 mg, 0.11 mmol) in a form of benzopyran was mixed with dimethylsulfoxide (DMSO, 3 mL) by shaking at room temperature for 10 min, 1 M lithium t-butoxide (LiOtBu-; 0.33 mL, 0.33 mmol) dissolved in tetrahydrofuran (THF) was added thereto and mixed by shaking at the same temperature for 20 min. 4-Trifluorobenzyl bromide (4-CF$_3$BnBr; 0.083 mL, 0.33 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-25; 202.7 mg).

To a suspension of the resin (200 mg, 0.16 mmol) of formula 4-1 in is DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-25 (28.9 mg, resin 4-1; yield=79% from loading capacity 0.55 mmol/g).

(II-3) N-benzylation (5-35) and deprotection (1-33) of 6-amino-2-ethyl-2-methyl-2H-benzopyran resin (4-2)

After carbamate resin of formula 4-2 (200.00 mg, 0.12 mmol) in a form of benzopyran was mixed with dimethylsulfoxide (DMSO, 3 mL) by shaking at room temperature for 10 min, 1 M lithium t-butoxide (LiOtBu-; 0.33 mL, 0.36 mmol) dissolved in tetrahydrofuran (THF) was added thereto and mixed by shaking at the same temperature for 20 min. Benzyl bromide (BnBr; 0.043 mL, 0.36 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-33; 204.3 mg).

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-33 (27.5 mg, resin 4-2; yield=82% from loading capacity 0.60 mmol/g).

(II-4) N-(2-methyl)benzylation (5-48) and deprotection (1-48) of 6-amino-2-tehyl-2-methyl-2H-benzopyran resin (4-2)

(II-5) N-benzylation (5-81) and deprotection (1-81) of 6-amino-2-methyl-2-propyl-2H-benzopyran resin (4-3)

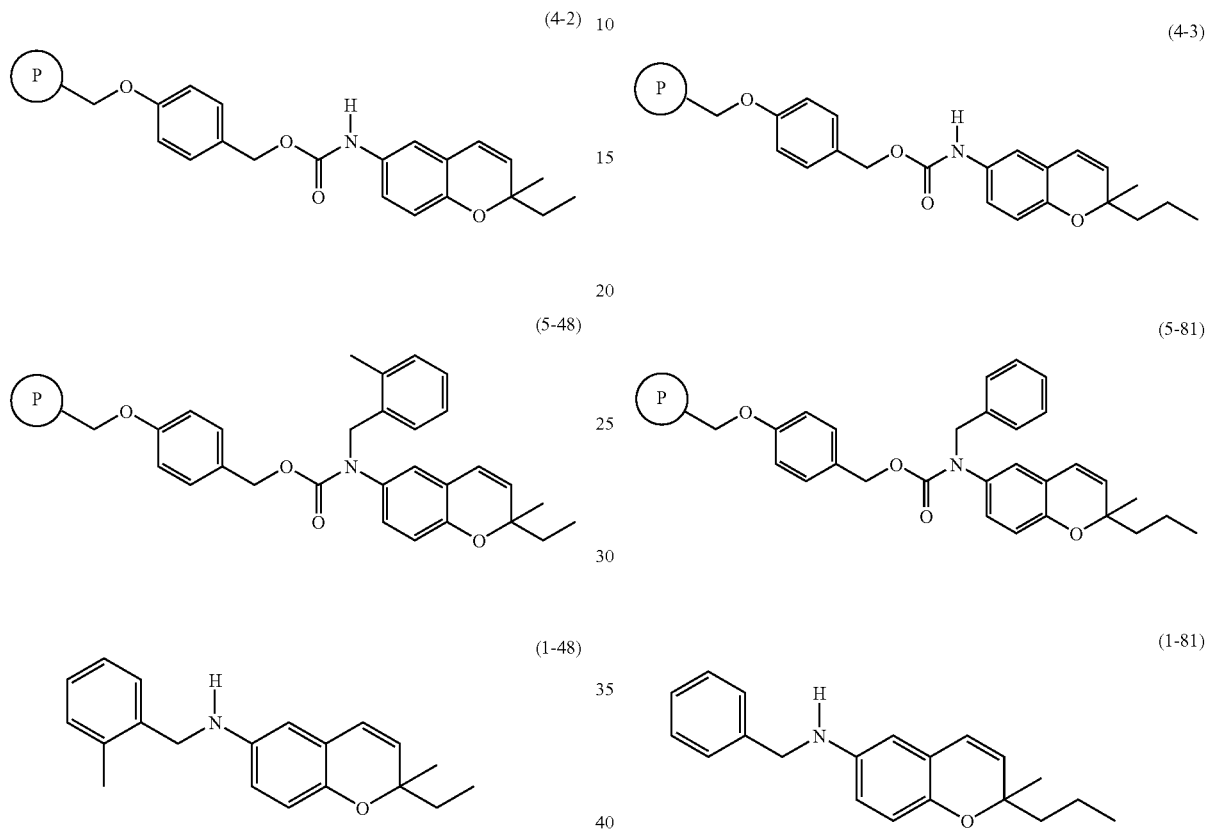

After carbamate resin of formula 4-2 (200.00 mg, 0.12 mmol) in a form of benzopyran was mixed with dimethylsulfoxide (DMSO, 3 mL) by shaking at room temperature for 10 min, 1 M lithium t-butoxide (LiOtBu-; 0.36 mL, 0.36 mmol) dissolved in tetrahydrofuran (THF) was added thereto and mixed by shaking at the same temperature for 20 min. 2-Methylbenzyl bromide (2-MeBnBr; 67 mg, 0.36 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-48; 206.3 mg).

To a suspension of the resin (200 mg, 0.16 mmol) of formulae 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-48 (27.1 mg, resin 4-2; yield=77% from loading capacity 0.60 mmol/g).

After carbamate resin of formula 4-3 (200.00 mg, 0.11 mmol) in a form of benzopyran was mixed with dimethylsulfoxide (DMSO, 3 mL) by shaking at room temperature for 10 min, 1 M lithium t-butoxide (LiOtBu-; 0.33 mL, 0.33 mmol) dissolved in tetrahydrofuran (THF) was added thereto and mixed by shaking at the same temperature for 20 min. 2-Benzyl bromide (BnBr; 0.039 mL, 0.33 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-81; 204.2 mg).

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-81 (25.4 mg, resin 4-3; yield=79% from loading capacity 0.55 mmol/g).

(II-6) N-(4-methyl)benzylation (5-90) and deprotectin (1-90) of 6-amino-2-methyl-2-propyl-2H-benzopyran resin (4-3)

(II-7) N-benzylation (5-121) and deprotection (1-121) of 6-amino-2-methyl-2-phenethyl-2H-benzopyran resin (4-4)

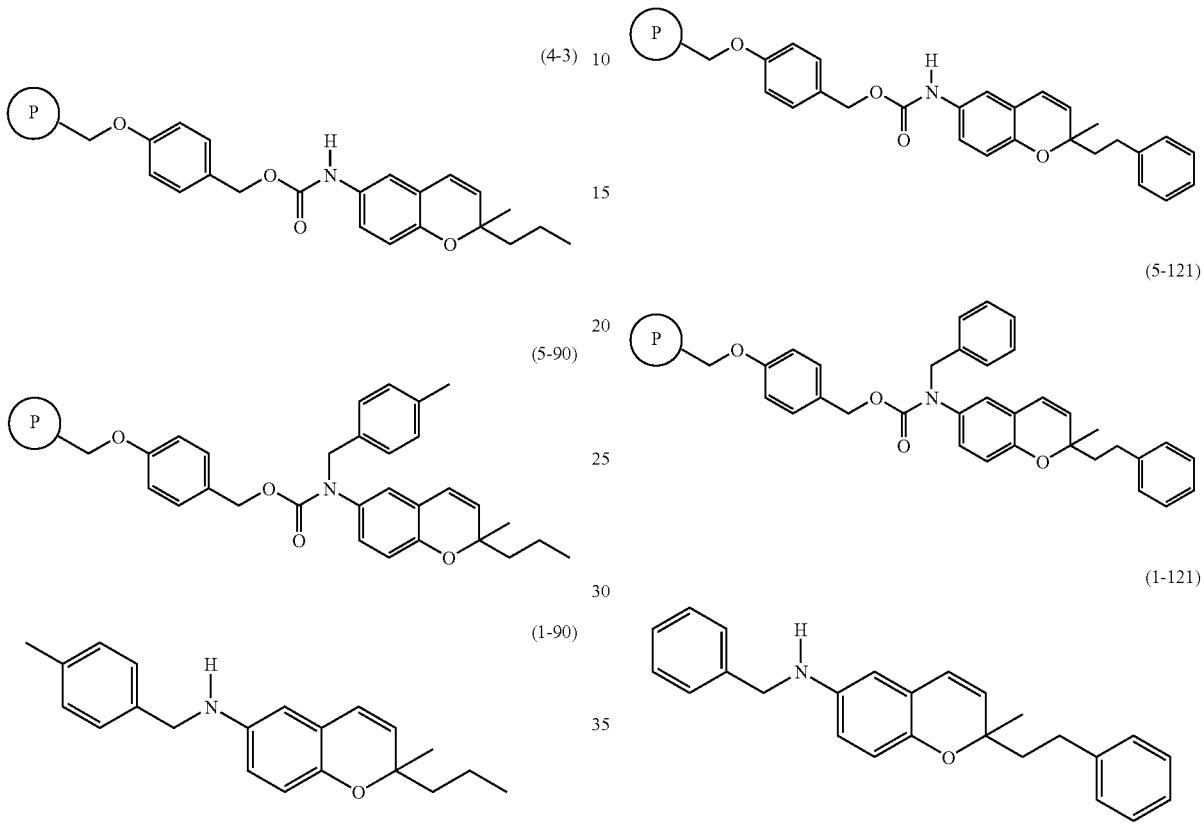

After carbamate resin of formula 4-3 (200.00 mg, 0.11 mmol) in a form of benzopyran was mixed with dimethylsulfoxide (DMSO, 3 mL) by shaking at room temperature for 10 min, 1 M lithium t-butoxide (LiOtBu-; 0.33 mL, 0.33 mmol) dissolved in tetrahydrofuran (THF) was added thereto and mixed by shaking at the same temperature for 20 min. 4-Methylbenzyl bromide (4-MeBnBr; 61 mg, 0.33 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-90; 203.7 mg).

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to is reduced concentration, the concentrate was isolated and purified with a silica gel column chromatography using a solvent mixture of hexane/ethylacetate (4/1, v/v), to obtain a lemon yellow oil of formula 1-90 (28.3 mg, resin 4-3; yield=84% from loading capacity 0.55 mmol/g).

After carbamate resin of formula 4-4 (200.00 mg, 0.10 mmol) in a form of benzopyran was mixed with dimethylsulfoxide (DMSO, 3 mL) by shaking at room temperature for 10 min, 1 M lithium t-butoxide (LiOtBu-; 0.30 mL, 0.30 mmol) dissolved in tetrahydrofuran (THF) was added thereto and mixed by shaking at the same temperature for 20 min. Benzyl bromide (BnBr; 0.036 mL, 0.30 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-121; 201.6 mg).

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-121 (28.4 mg, resin 4-4; yield=80% from loading capacity 0.50 mmol/g).

(II-8) N-(4-methoxy)benzylation (5-124) and deprotection (1-124) of 2-methyl-2-phemethyl-6-amino benzopyran resin (4-4)

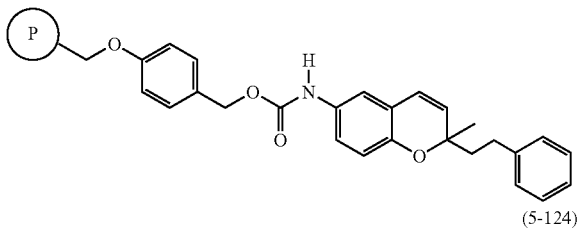
(4-4)

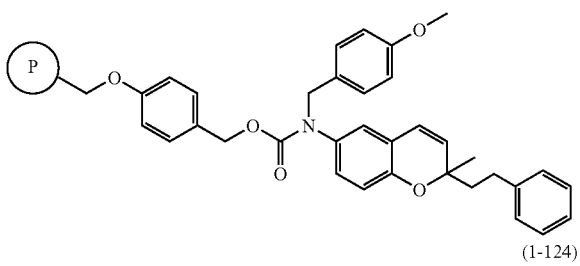
(5-124)

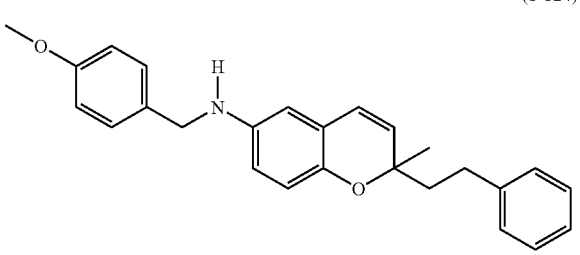
(1-124)

After carbamate resin of formula 4-4 (200.00 mg, 0.10 mmol) in a form of benzopyran was mixed with dimethylsulfoxide (DMSO, 3 mL) by shaking at room temperature for 10 min, 1 M lithium t-butoxide (LiOtBu-; 0.30 mL, 0.30 mmol) dissolved in tetrahydrofuran (THF) was added thereto and mixed by shaking at the same temperature for 20 min. 4-Methoxybenzyl chloride (4-MeOBnBr; 0.041 mL, 0.30 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-124; 202.3 mg).

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-124 (31.9 mg, resin 4-4; yield=83% from loading capacity 0.50 mmol/g).

(II-9) N-benzylation (5-161) and deprotection (1-161) of 6-amino-2-(4-methoxyphenethyl)-2-methyl-2H-benzopyran resin (4-5)

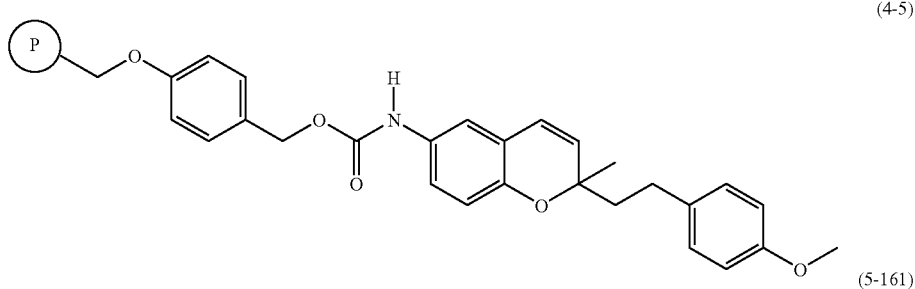
(4-5)

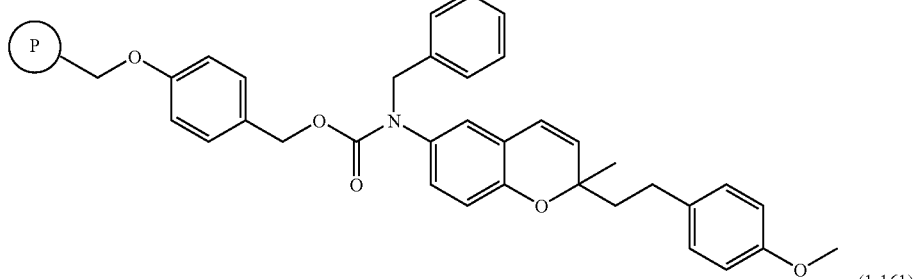
(5-161)

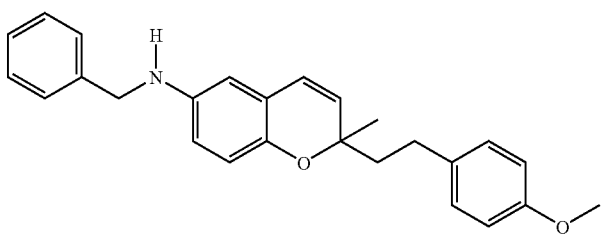
(1-161)

After carbamate resin of formula 4-5 (200.00 mg, 0.13 mmol) in a form of benzopyran was mixed with dimethylsulfoxide (DMSO, 3 mL) by shaking at room temperature for 10 min, 1 M lithium t-butoxide (LiOtBu-; 0.39 mL, 0.39 mmol) dissolved in tetrahydrofuran (THF) was added thereto and mixed by shaking at the same temperature for 20 min. Benzyl bromide (BnBr; 0.046 mL, 0.39 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-161; 204.9 mg).

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-161 (43.0 mg, resin 4-5; yield=86% from loading capacity 0.65 mmol/g).

(II-10) N-(3-fluoro)benzylation (5-172) and deprotection (1-172) of 6-amino-2-(4-methoxyphenethyl)-2-methyl-2H-benzopyran resin (4-5)

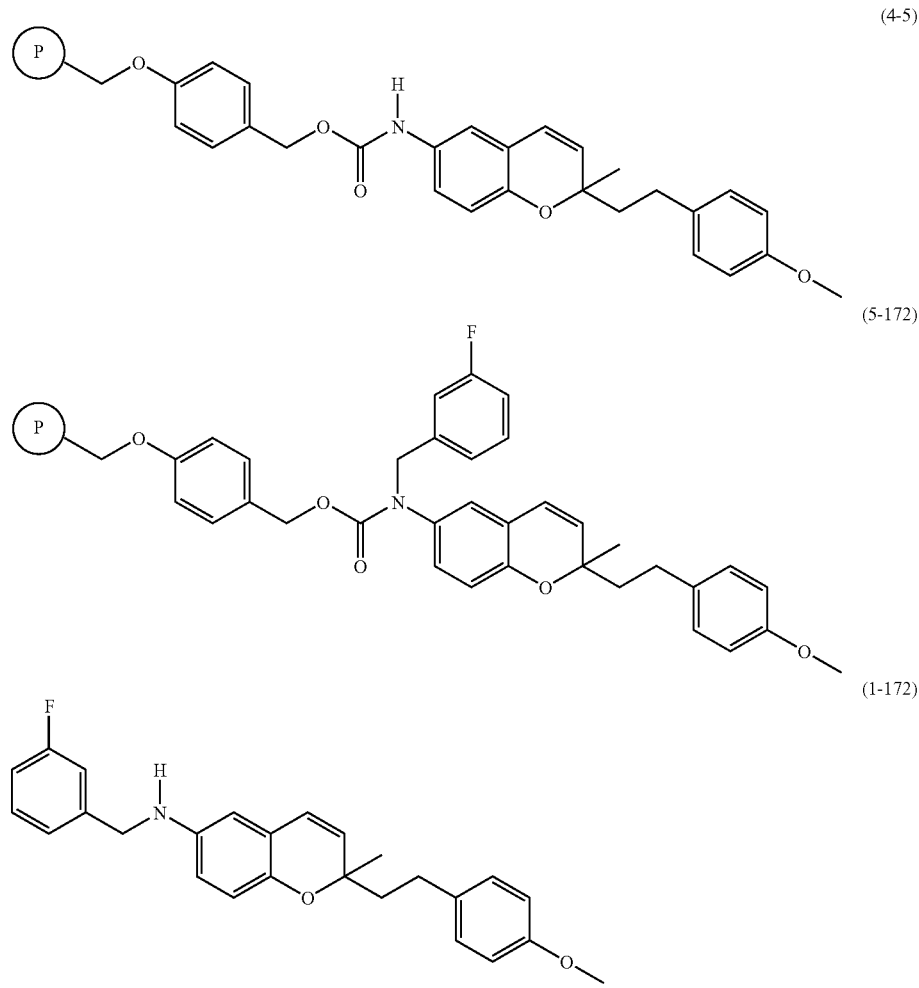

After carbamate resin of formula 4-5 (200.00 mg, 0.13 mmol) in a form of benzopyran was mixed with dimethylsulfoxide (DMSO, 3 mL) by shaking at room temperature for 10 min,. 1 M lithium t-butoxide (LiOtBu-; 0.39 mL, 0.39 mmol) dissolved in tetrahydrofuran (THF) was added thereto and mixed by shaking at the same temperature for 20 min. 3-Fluorbenzyl bromide (3-F-BnBr; 0.048 mL, 0.39 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-172; 206.0 mg).

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-172 (42.4 mg, resin 4-5; yield=81% from loading capacity 0.65 mmol/g).

(II-11) N-benzylation (5-201) and deprotection (1-201) of 6-amino-2,2,7-trimethyl-2H-benzopyran resin (4-6)

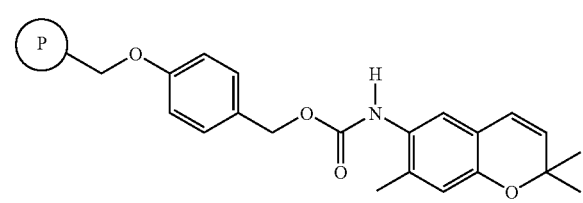

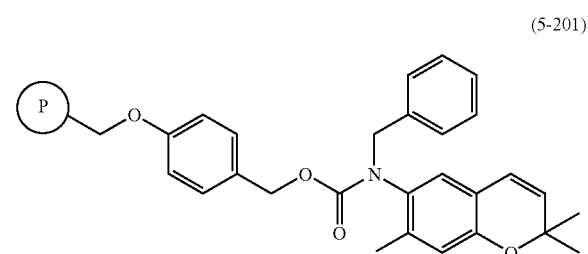

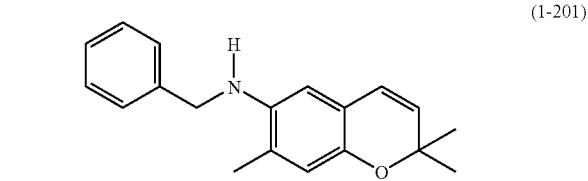

After carbamate resin of formula 4-6 (200.00 mg, 0.11 mmol) in a form of benzopyran was mixed with dimethylsulfoxide (DMSO, 3 mL) by shaking at room temperature for 10 min, 1 M lithium t-butoxide (LiOtBu-; 0.33 mL, 0.33 mmol) dissolved in tetrahydrofuran (THF) was added thereto and mixed by shaking at the same temperature for 20 min. Benzyl bromide (BnBr; 0.039 mL, 0.33 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-201; 201.9 mg).

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-201 (23.6 mg, resin 4-6; yield=77% from loading capacity 0.55 mmol/g).

(II-12) N-(4-fluoromethyl)benzylation (5-225) and deprotection (1-225) of 6-amino-2,2,7-trimethyl-2H-benzopyran resin (4-6)

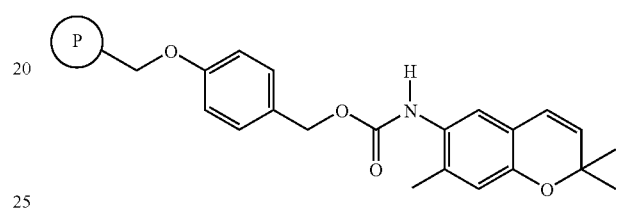

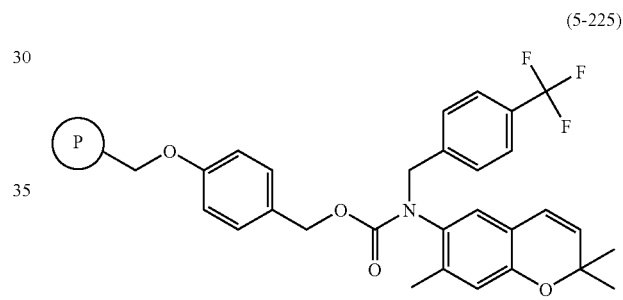

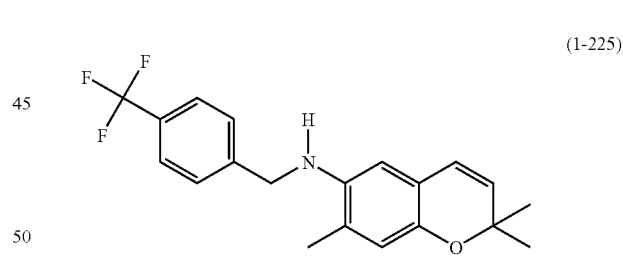

After carbamate resin of formula 4-6 (200.00 mg, 0.11 mmol) in a form of benzopyran was mixed with dimethylsulfoxide (DMSO, 3 mL) by shaking at room temperature for 10 min, 1 M lithium t-butoxide (LiOtBu-; 0.33 mL, 0.33 mmol) dissolved in tetrahydrofuran (THF) was added thereto and mixed by shaking at the same temperature for 20 min. 4-Trifluorobenzyl bromide (4-CF$_3$BnBr; 0.051 mL, 0.33 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-225; 201.9 mg).

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-225 (28.6 mg, resin 4-6; yield=75% from loading capacity 0.55 mmol/g).

(II-13) N-benzylation (5-241) and deprotection (1-241) of 6-amino-2,7-dimethyl-2-ethyl-2H-benzopyran resin (4-7)

added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-241 (28.2 mg, resin 4-7; yield=80% from loading capacity 0.60 mmol/g).

(II-14) N-(4-t-butyl)benzylation (5-247) and deprotection (1-247) of 6-amino-2,7-dianethyl-2-ethyl-2H-benzopyran resin (4-7)

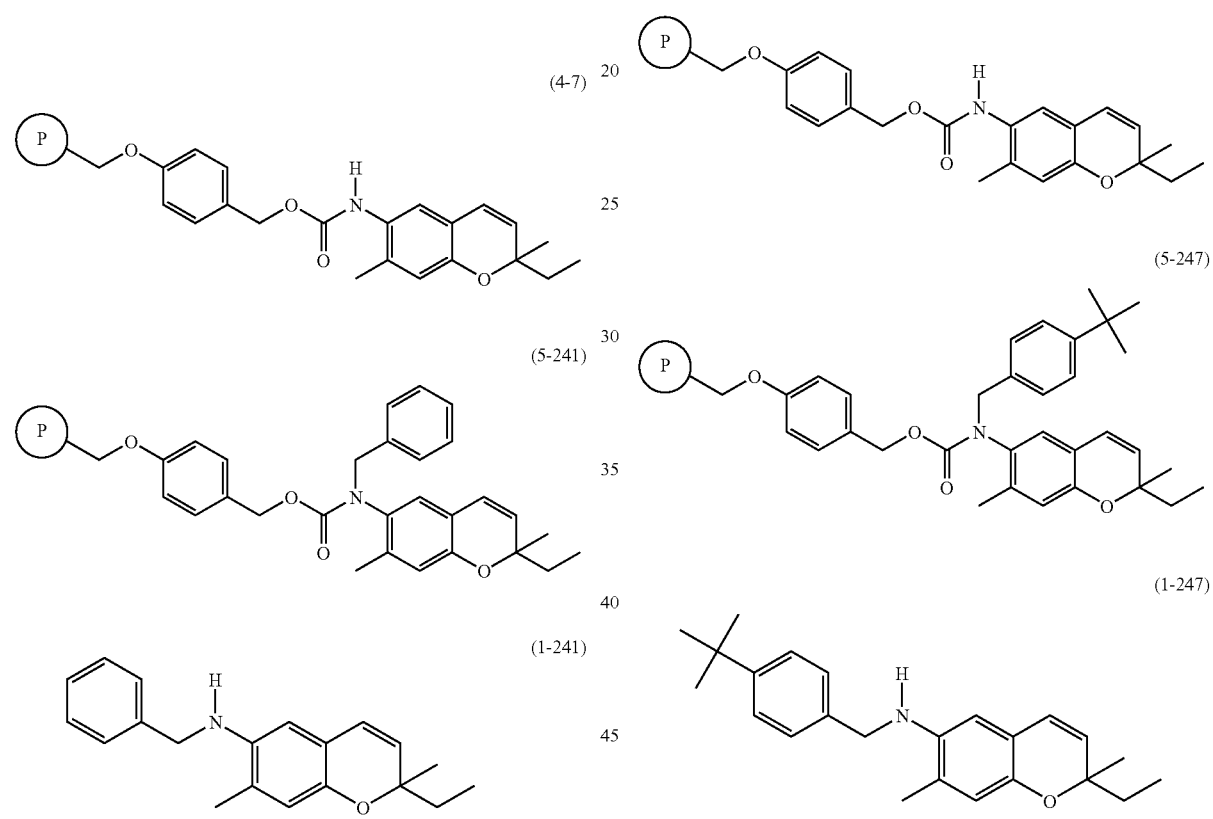

After carbamate resin of formula 4-7 (200.00 mg, 0.12 mmol) in a form of benzopyran was mixed with dimethylsulfoxide (DMSO, 3 mL) by shaking at room temperature for 10 min, 1 M lithium t-butoxide (LiOtBu-; 0.36 mL, 0.36 mmol) dissolved in tetrahydrofuran (THF) was added thereto and mixed by shaking at the same temperature for 20 min. Benzyl bromide (BnBr; 0.043 mL, 0.36 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-241; 203.3 mg).

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was After carbamate resin of formula 4-7 (200.00 mg, 0.12 mmol) in a form of benzopyran was mixed with dimethylsulfoxide (DMSO, 3 mL) by shaking at room temperature for 10 min, 1 M lithium t-butoxide (LiOtBu-; 0.36 mL, 0.36 mmol) dissolved in tetrahydrofuran (THF) was added thereto and mixed by shaking at the same temperature for 20 min. t-Butylbenzyl bromide (t-Bu-BnBr; 0.066 mL, 0.36 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-247; 203.1 mg).

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-247 (34.8 mg, resin 4-7; yield=83% from loading capacity 0.60 mmol/g).

(II-15) N-benzylation (5-281) and deprotection (1-281) of 6-amino-2,7-dimethyl-2-propyl-2H-benzopyran resin (4-8)

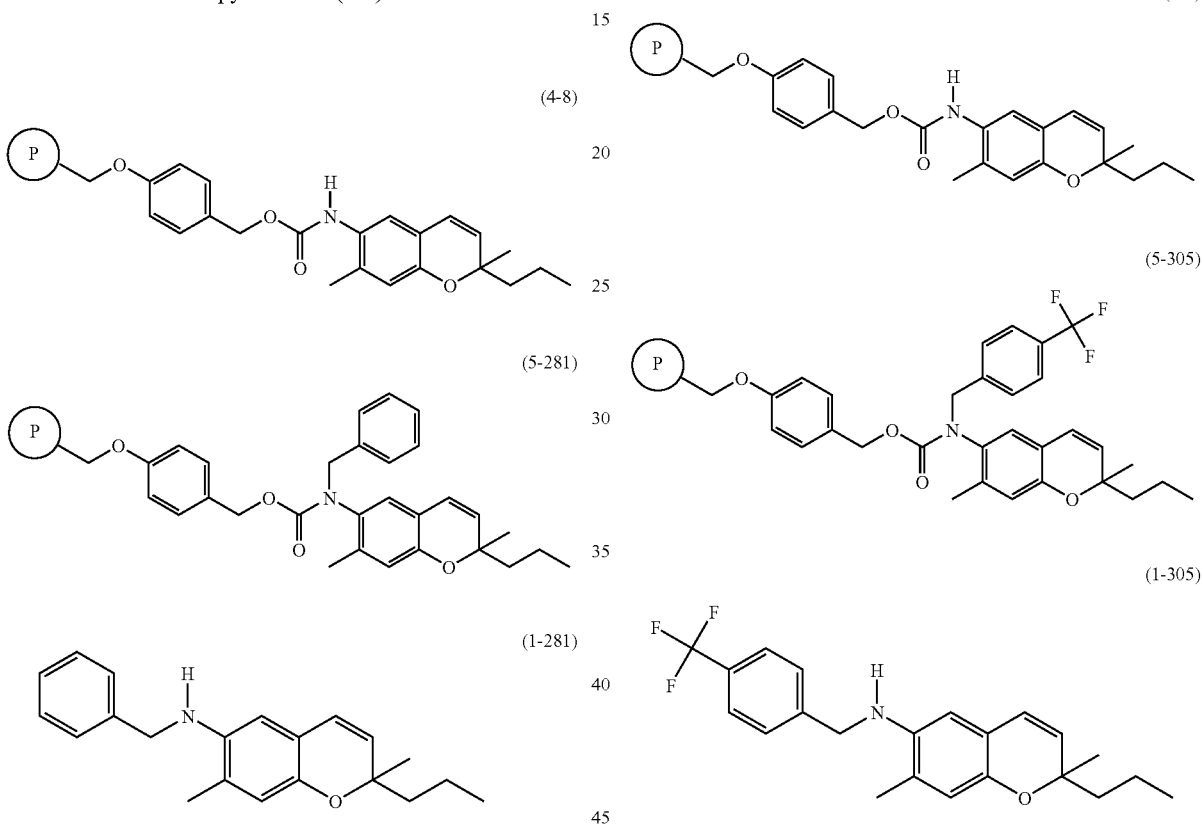

After carbamate resin of formula 4-8 (200.00 mg, 0.12 mmol) in a form of benzopyran was mixed with dimethylsulfoxide (DMSO, 3 mL) by shaking at room temperature for 10 min, 1 M lithium t-butoxide (LiOtBu-; 0.36 mL, 0.36 mmol) dissolved in tetrahydrofuran (THF) was added thereto and mixed by shaking at the same temperature for 20 min. Benzyl bromide (BnBr; 0.043 mL, 0.36 mmol) was added thereto and the reaction mixture was shaken at 35° C. for 15 hrs. After the reaction was completed, the reaction mixture was subjected to filtration and repeatedly washed with DMF, MC, MC/MeOH and MeOH, to obtain a light-brown solid resin (Formula 5-281; 202.7 mg).

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-281 (30.4 mg, resin 4-8; yield=83% from loading capacity 0.60 mmol/g).

(II-16) N-(4-trifluoromethyl)benzylation (5-305) and deprotection (1-305) of 6-amino-2,7-dinethyl-2-propyl-2H-benzopyran resin (4-8)

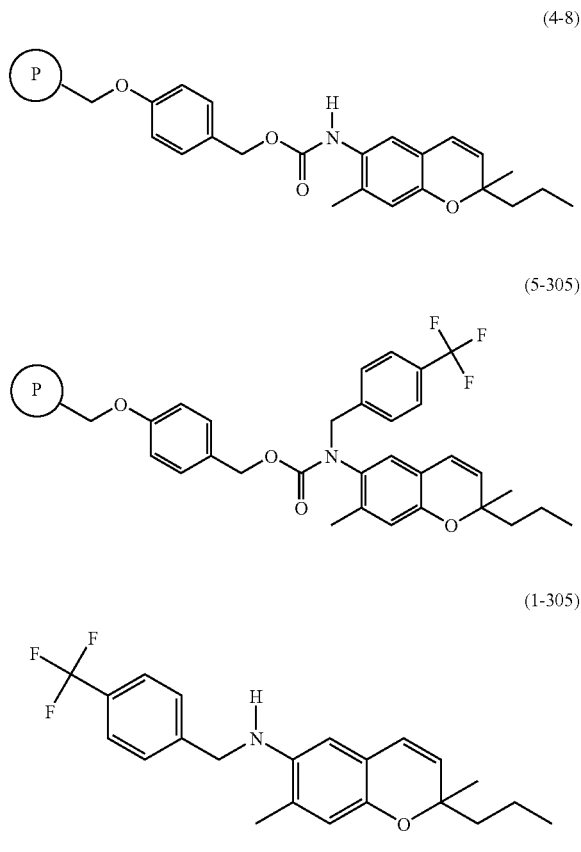

After carbamate resin of formula 4-8 (200.00 mg, 0.12 mmol) in a form of benzopyran was mixed with dimethylsulfoxide (DMSO, 3 mL) by shaking at room temperature for 10 min, 1 M lithium t-butoxide (LiOtBu-; 0.36 mL, 0.36 mmol) dissolved in tetrahydrofuran (THF) was added thereto and mixed by shaking at the same temperature for 20 min. Trifluorobenzyl bromide (4-CF₃BnBr; 0.056 mL, 0.36 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-305; 201.9 mg).

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-305 (35.1 mg, resin 4-8; yield=78% from loading capacity 0.60 mmol/g).

(II-17) N-benzylation (5-321) and deprotection (1-321) of 6-amino-2,7-dimethyl-2-phenethyl-2H-benzopyran resin (4-9)

(II-18) N-(4-methoxy)benzylation (5-324) and deprotection (1-324) of 6-amino-2,7-dimethyl-2-phenethyl-2H-benzopyran resin (4-9)

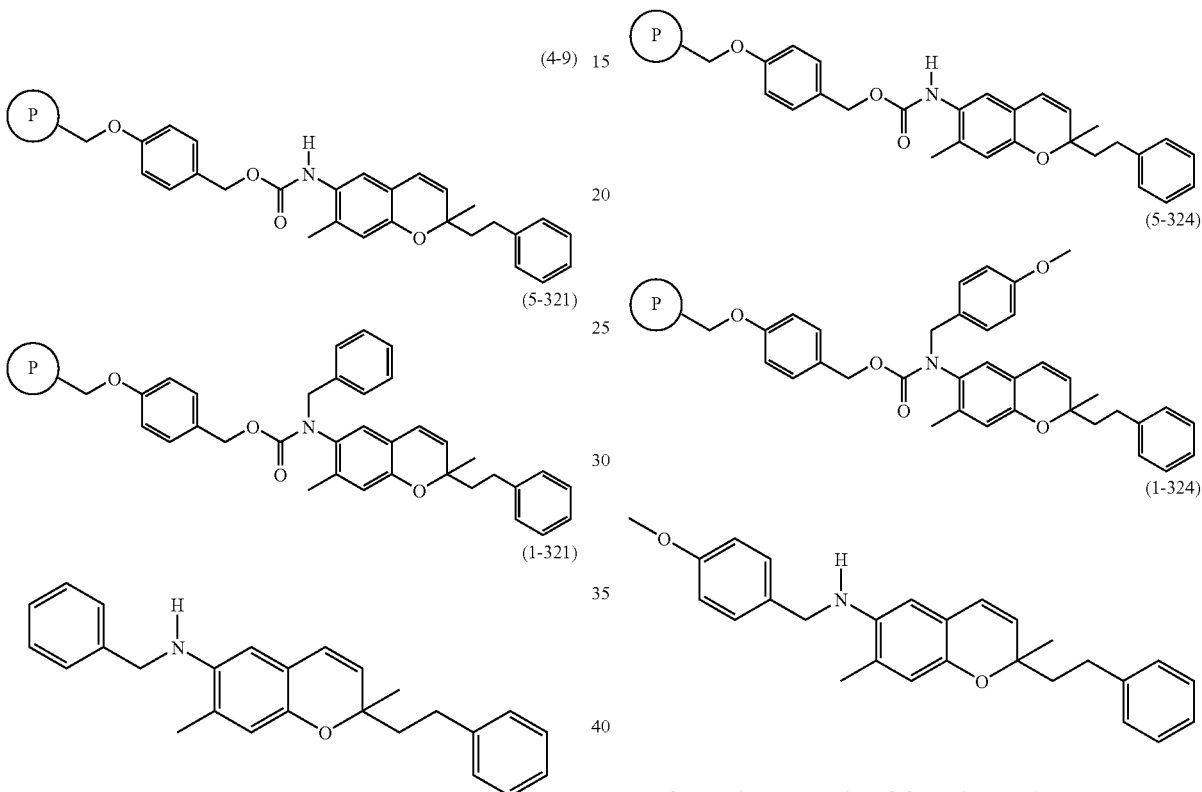

After carbamate resin of formula 4-9 (200.00 mg, 0.10 mmol) in a form of benzopyran was mixed with dimethylsulfoxide (DMSO, 3 mL) by shaking at room temperature for 10 min, 1 M lithium t-butoxide (LiOtBu-; 0.33 mL, 0.33 mmol) dissolved in tetrahydrofuran (THF) was added thereto and mixed by shaking at the same temperature for 20 min. Benzyl bromide (BnBr; 0.039 mL, 0.33 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-321; 205.7 mg).

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-321 (32.1 mg, resin 4-9; yield=87% from loading capacity 0.50 mmol/g).

After carbamate resin of formula 4-9 (200.00 mg, 0.10 mmol) in a form of benzopyran was mixed with dimethylsulfoxide (DMSO, 3 mL) by shaking at room temperature for 10 min, 1 M lithium t-butoxide (LiOtBu-; 0.33 mL, 0.33 mmol) dissolved in tetrahydrofuran (THF) was added thereto and mixed by shaking at the same temperature for 20 min. 4-Methoxybenzyl chloride (4-MeO-BnCl; 0.045 mL, 0.33 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-324; 203.5 mg).

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-324 (32.3 mg, resin 4-9; yield=81% from loading capacity 0.50 mmol/g).

(II-19) N-benzylation (5-361) and deprotection (1-361) of 6-amino-8-bromo-2,2,7-trimethyl-2H-benzopyran resin (4-10)

v/v), to obtain a lemon yellow oil of formula 1-361 (29.5 mg, resin 4-10; yield=75% from loading capacity 0.55 mmol/g).

(II-20) N-(4-methoxy)benzylation (5-364) and deprotection (1-364) of 6-amino-8-bromo-2,2,7-trimethyl-2H-benzopyran resin (4-10)

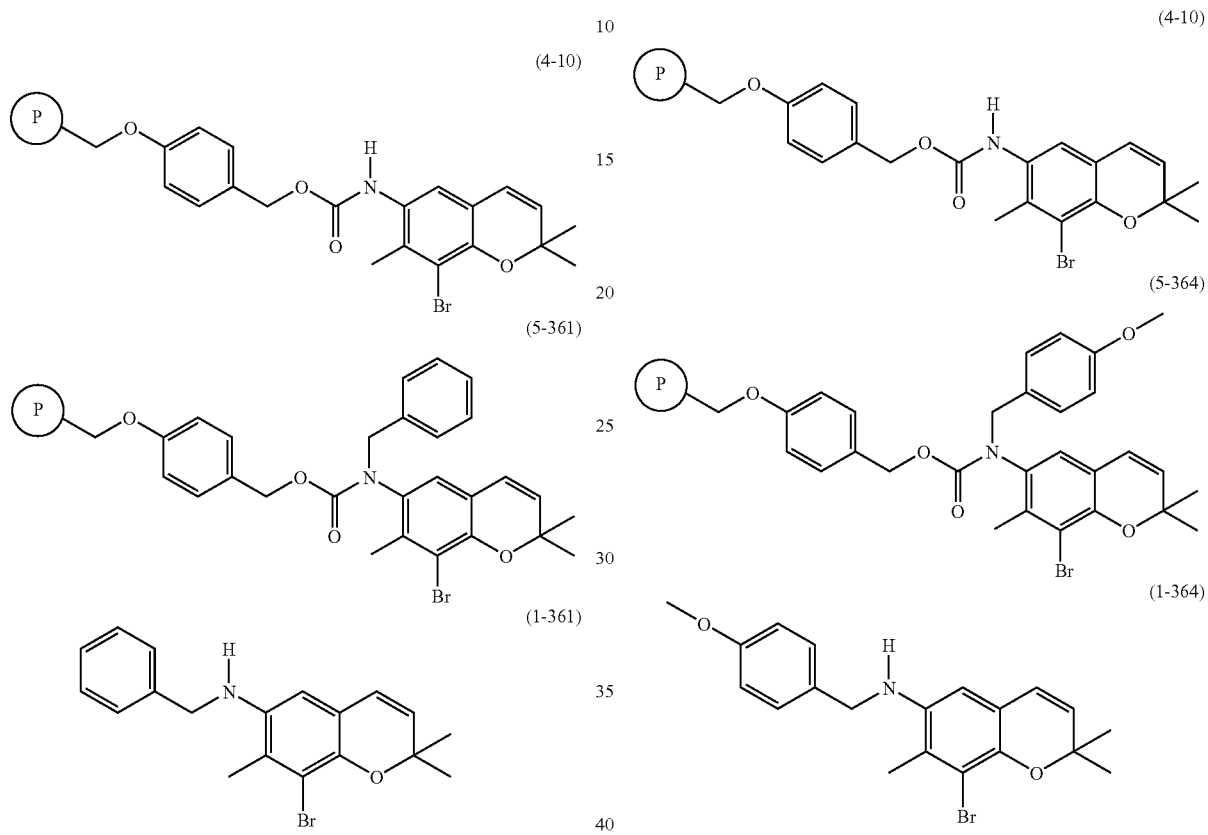

After carbamate resin of formula 4-10 (200.00 mg, 0.11 mmol) in a form of benzopyran was mixed with dimethylsulfoxide (DMSO, 3 mL) by shaking at room temperature for 10 min, 1 M lithium t-butoxide (LiOtBu-; 0.33 mL, 0.33 mmol) dissolved in tetrahydrofuran (THF) was added thereto and mixed by shaking at the same temperature for 20 min. Benzyl bromide (BnBr; 0.039 mL, 0.33 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-361; 203.9 mg).

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, After carbamate resin of formula 4-10 (200.00 mg, 0.11 mmol) in a form of benzopyran was mixed with dimethylsulfoxide (DMSO, 3 mL) by shaking at room temperature for 10 min, 1 M lithium t-butoxide (LiOtBu-; 0.36 mL, 0.36 mmol) dissolved in tetrahydrofuran (THF) was added thereto and mixed by shaking at the same temperature for 20 min. 4-Methoxybenzyl chloride (4-MeO-BnCl; 0.045 mL, 0.33 mmol) was added thereto and the reaction mixture was shaken at 35 ° C. for 15 hrs. After the reaction was completed, the reaction mixture was subjected to filtration and repeatedly washed with DMF, DCM, DCM/MeOH and MeOH, to obtain a light-brown solid resin (Formula 5-364; 202.5 mg).

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-364 (33.7 mg, resin 4-10; yield=79% from loading capacity 0.55 mmol/g).

(II-21) N-benzylation (5-401) and deprotection (1-401) of 6-amino-2,2-dimethyl-8-phenyl-2H-benzopyran resin (4-11)

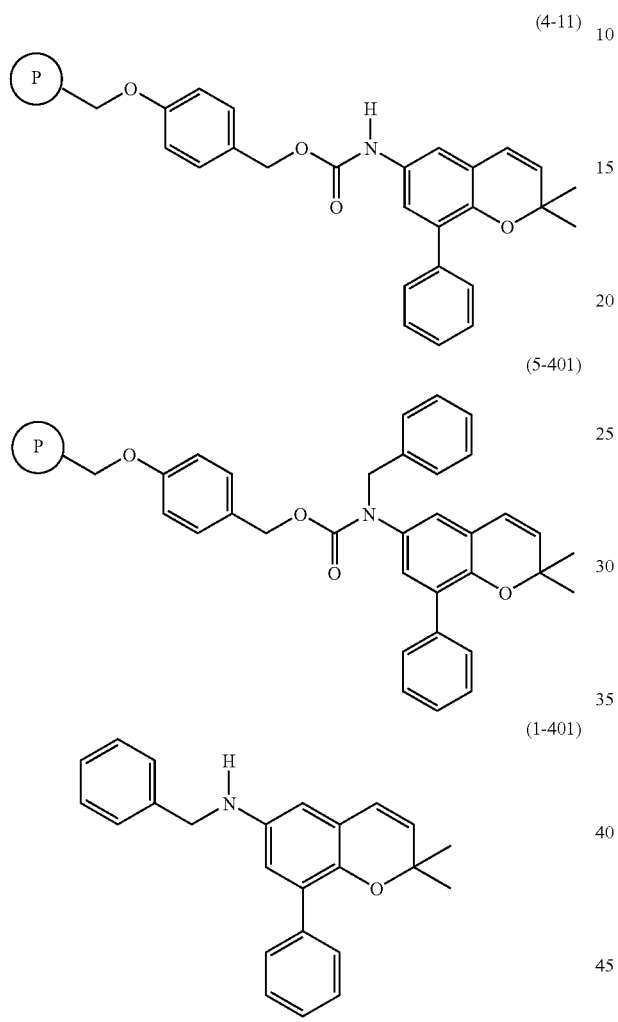

After carbamate resin of formula 4-11 (200.00 mg, 0.13 mmol) in a form of benzopyran was mixed with dimethylsulfoxide (DMSO, 3 mL) by shaking at room temperature for 10 min, 1 M lithium t-butoxide (LiOtBu-; 0.39 mL, 0.39 mmol) dissolved in tetrahydrofuran (THF) was added thereto and mixed by shaking at the same temperature for 20 min. Benzyl bromide (BnBr; 0.046 mL, 0.39 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-401; 204.0 mg).

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-401 (36.4 mg, resin 4-11; yield=82% from loading capacity 0.65 mmol/g).

(II-22) N-(3-chloro)benzylation (5-415) and deprotection (1-415) of 6-amino-2,2-dimethyl-8-phenyl-2H-benzopyran resin (4-11)

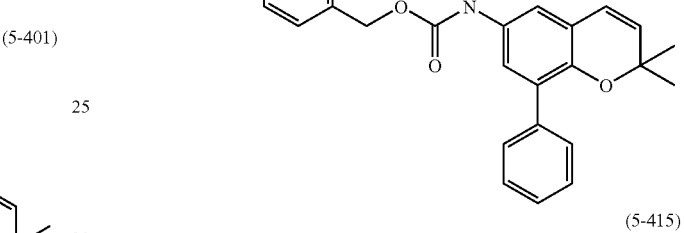

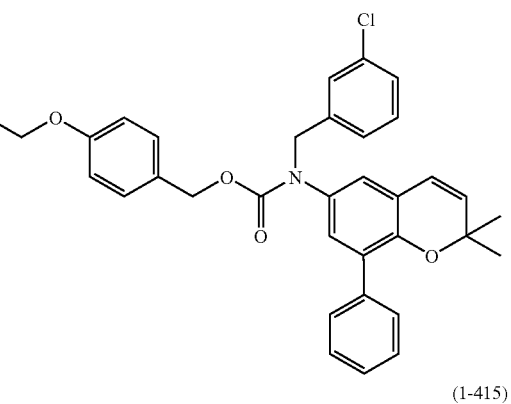

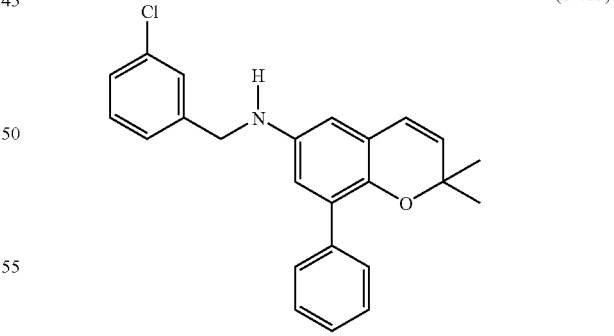

After carbamate resin of formula 4-11 (200.00 mg, 0.13 mmol) in a form of benzopyran was mixed with dimethylsulfoxide (DMSO, 3 mL) by shaking at room temperature for 10 min, 1 M lithium t-butoxide (LiOtBu-; 0.39 mL, 0.39 mmol) dissolved in tetrahydrofuran (THF) was added thereto and mixed by shaking at the same temperature for 20 min. 3-Chlorobenzyl bromide (3-ClBnBr; 0.051 mL, 0.39 mmol) was added thereto and the reaction mixture was shaken at 35° C. for 15 hrs. After the reaction was completed, the reaction mixture was subjected to filtration and repeatedly washed with DMF, DCM, DCM/MeOH and MeOH, to obtain a light-brown solid resin (Formula 5-415; 203.2 mg).

To a suspension of the resin (200 mg, 0.16 mmol) of formula 4-1 in DCM(5 mL) was added trifluoroaceic acid (TFA, 1 mL), the reaction mixture was shaken at room temperature for 4 hrs. After the reaction was completed, the resin was filtered off and repeatedly washed with DCM and MeOH and concentrated. After ethylacetate (3 mL) was added to the concentrated mixture, the reaction mixture was subjected to filtration with a strong anion exchange resin (SAX resin) and repeatedly washed with ethylacetate to remove residual trifluoroacetic acid. After the filtrate was subjected to reduced concentration, the concentrate was isolated and purified with a silica gel column chromatography using a solvent mixture of hexane/ethylacetate (4/1, v/v), to obtain a lemon yellow oil of formula 1-415 (36.1 mg, resin 4-11; yield=74% from loading capacity 0.65 mmol/g).

6-alkylamino-2,2'-disubstituted-3,4-dihydro-7,8-disubstituted benzopyran derivatives synthesized according to the same solid-phase parallel synthesis described in Examples are showin in Table 1.

TABLE 1

(1)

| Compound No. | $R^1$ | $R^2$ | $R^3$ | n | $R^4$ | NMR & Mass analytic results |
|---|---|---|---|---|---|---|
| 1-1 | Bn | H | H | 0 | Me | $^1$H NMR(300 MHz, CDCl$_3$) δ 7.39-7.26(m, 5H), 6.64(d, 1H, J= 8.5Hz), 6.45(dd, 1H, J=8.5 Hz, J=2.8 Hz), 6.33(d, 1H, J=2.8 Hz), 6.24(d, 1H, J=9.7 Hz), 5.60(d, 1H, J=9.7 Hz), 4.27(s, 2H), 1.39(s, 6H); NMR(75 $^{13}$C MHz, CDCl$_3$): 145.17, 142.19, 139.52, 131.59, 128.55, 127.62, 127.17, 122.58, 121.90, 116.80, 113.88, 111.00, 75.46, 49.34, 27.5; m/z: 256.20 |
| 1-2 | 2-MeO-Bn | H | H | 0 | Me | m/z: 295.35 |
| 1-3 | 3-MeO-Bn | H | H | 0 | Me | m/z: 295.23 |
| 1-4 | 4-MeO-Bn | H | H | 0 | Me | $^1$H NMR(200 MHz, CDCl$_3$) δ 7.27(d, 2H, J=8.6 Hz), 6.86(d, 2H, J=8.6 Hz), 6.64(d, 1H, J=8.5 Hz), 6.44(dd, 1H, J=8.5 Hz, J=2.8 Hz), 6.33(d, 1H, J=2.8 Hz), 6.23(d, 1H, J=9.8 Hz), 5.59(d, 1H, J=9.8 Hz), 4.17(s, 2H), 3.79(s, 3H), 1.39(s, 6H) m/s: 295.35 |
| 1-5 | 2-t-Bu-Bn | H | H | 0 | Me | m/z: 321.36 |
| 1-6 | 3-t-Bu-Bn | H | H | 0 | Me | m/z: 321.32 |
| 1-7 | 4-t-Bu-Bn | H | H | 0 | Me | $^1$H NMR(200 MHz, CDCl$_3$) δ 7.39-7.24(m, 4H), 6.64(d, 1H, J=8.6 Hz), 6.45(dd, 1H, J=8.6 Hz, J=2.6 Hz), 6.34(d, 1H, J=2.6 Hz), 6.24(d, 1H, J=9.8 Hz), 5.60(d, 1H, J=9.8 Hz), 4.21(s, 2H), 1.39(s, 6H), 1.32(s, 9H); m/z: 321.40 |
| 1-8 | 2-Me-Bn | H | H | 0 | Me | $^1$H NMR(300 MHz, CDCl$_3$) δ 7.26(m, 1H), 7.19(m, 3H), 6.66(d, 1H, J=8.5 Hz), 6.47(dd, 1H, J=8.5 Hz, J=2.7 Hz), 6.34(d, 1H, J=2.7 Hz), 6.25(d, 1H, J=9.8 Hz), 5.61(d, 1H, J=9.8 Hz), 4.21(s, 2H), 2.37(s, 3H), 1.40(s, 6H); m/z: 279.41 |
| 1-9 | 3-Me-Bn | H | H | 0 | Me | m/z: 279.35 |
| 1-10 | 4-Me-Bn | H | H | 0 | Me | $^1$H NMR(300 MHz, CDCl$_3$) δ 7.25(d, 1H, J=7.9 Hz), 7.14(d, 2H, J=7.92 Hz), 6.64(d, 1H, J=8.1 Hz), 6.47(dd, 1H, J=8.1 Hz, J=2.7 Hz), 6.36(d, 1H, J=2.7 Hz), 6.24(d, 1H, J=9.6 Hz), 5.60(d, 1H, J=9.6 Hz), 4.22(s, 2H), 2.34(s, 3H), 1.39(s, 6H); m/z: 279.36 |
| 1-11 | 2-F-Bn | H | H | 0 | Me | $^1$H NMR(200 MHz, CDCl$_3$) δ 7.44-7.36(m, 1H), 7.29-7.21(m, 1H), 7.15-6.70(m, 2H), 6.68(d, 1H, J=8.3 Hz), 6.48(dd, 1H, J=8.3 Hz, J=2.6 Hz), 6.36(d, 1H, J=2.6 Hz), 6.27(d, 1H, J=9.8 Hz), 5.63(d, 1H, J=9.8 Hz), 4.40(s, 2H), 3.61(br, 1H), 1.42(s, 6H); m/z: 283.37 |
| 1-12 | 3-F-Bn | H | H | 0 | Me | $^1$H NMR(300 MHz, CDCl$_3$) δ 7.28(m, 1H), 7.12(m, 2H), 6.93(m, 1H), 6.64(d, 1H, J=8.5 Hz), 6.42(dd, 1H, J=8.5 Hz, J=2.8 Hz), 6.30(d, 1H, J=2.8 Hz), 6.23(d, 1H, J=9.7 Hz), 5.60(d, 1H, J=9.7 Hz), 4.28(s, 2H), 1.39(s, 6H); m/z: 283.45 |

TABLE 1-continued (structure 1): A 2H-chromene with 2-methyl and 2-(CH₂)ₙR⁴ substituents; 6-position bears R¹–NH–; 7-position R²; 8-position R³.

| Compound No. | R¹ | R² | R³ | n | R⁴ | NMR & Mass analytic results |
|---|---|---|---|---|---|---|
| 1-13 | 4-F-Bn | H | H | 0 | Me | ¹H NMR(500 MHz, CDCl₃): δ 7.33-7.30(m, 2H), 7.02-6.99(m, 2H), 6.64(d, 1H, J=8.5 Hz), 6.45(dd, 1H, J=8.5 Hz, J=2.8 Hz), 6.34(d, 1H, J=2.8 Hz), 6.23(d, 1H, J=9.7 Hz), 5.61(d, 1H, J=9.7 Hz), 4.22(s, 2H), 1.39(s, 6H); m/z: 283.25 |
| 1-14 | 2-Cl-Bn | H | H | 0 | Me | m/z: 299.80 |
| 1-15 | 3-Cl-Bn | H | H | 0 | Me | ¹H NMR(200 MHz, CDCl₃) δ 7.37(s, 1H), 7.25(m, 3H), 6.64(d, 1H, J=8.6 Hz), 6.42(dd, 1H, J=8.6 Hz, J=2.8 Hz), 6.31(d, 1H, J=2.8 Hz), 6.23(d, 1H, J=9.8 Hz), 5.61(d, 1H, J=9.8 Hz), 4.25(s, 2H), 1.39(s, 6H); m/z: 299.84 |
| 1-16 | 4-Cl-Bn | H | H | 0 | Me | m/z: 299.81 |
| 1-17 | 2-CN-Bn | H | H | 0 | Me | ¹H NMR(200 MHz, CDCl₃) δ 7.96(d, 1H, J=6.7 Hz), 7.56-7.27(m, 3H), 7.20(dd, 1H, J=8.5 Hz, J=2.4 Hz), 7.09(d, 1H, J=2.4 Hz), 6.78(d, 1H, J=8.5 Hz), 6.35(d, 1H, J=9.7 Hz), 5.62(d, 1H, J=9.7 Hz), 5.43(s, 2H), 1.50(s, 6H); m/z: 290.35 |
| 1-18 | 3-CN-Bn | H | H | 0 | Me | m/z: 290.31 |
| 1-19 | 4-CN-Bn | H | H | 0 | Me | ¹H NMR(200 MHz, CDCl₃) δ 7.63(d, 2H, J=8.0 Hz), 7.49(d, 2H, J=8.0 Hz), 6.64(d, 1H, J=8.7 Hz), 6.41(m, 1H), 6.27(d, 1H, J=2.6 Hz), 6.21(d, 1H, J=9.8 Hz), 5.61(d, 1H, J=9.8 Hz), 4.37(s, 2H), 1.40(s, 6H); m/z: 290.34 |
| 1-20 | 2-NO₂-Bn | H | H | 0 | Me | m/z: 310.16 |
| 1-21 | 3-NO₂-Bn | H | H | 0 | Me | m/z: 310.17 |
| 1-22 | 3-NO₂-Bn | H | H | 0 | Me | ¹H NMR(300 MHz, CDCl₃) δ 8.09(d, 2H, J=9.0 Hz), 7.46(d, 2H, J=9.0 Hz), 6.95(dd, 1H, J=9.0 Hz, J=3.0 Hz), 6.90(d, 1H, J=3.0 Hz), 6.69(d, 1H, J=9.0 Hz), 6.19(d, 1H, J=9.0 Hz), 5.69(d, 1H, J=9.0 Hz), 4.38(s, 2H), 1.42(s, 6H); m/z: 310.31 |
| 1-23 | 2-CF₃-Bn | H | H | 0 | Me | m/z: 333.26 |
| 1-24 | 3-CF₃-Bn | H | H | 0 | Me | m/z: 333.24 |
| 1-25 | 4-CF₃-Bn | H | H | 0 | Me | ¹H NMR(200 MHz, CDCl₃) δ 7.59(d, 2H, J=8.2 Hz), 7.48(d, 2H, J=8.2 Hz), 6.65(d, 1H, J=8.4 Hz), 6.42(dd, 1H, J=8.4 Hz, J=2.8 Hz), 6.30(d, 1H, J=2.8 Hz), 6.23(d, 1H, J=9.9 Hz), 5.61(d, 1H, J=9.9 Hz), 4.35(s, 2H), 1.40(s, 6H); m/z: 333.35 |
| 1-26 | 4-EtO-Bn | H | H | 0 | Me | ¹H NMR(200 MHz, CDCl₃) δ 7.30(d, 2H, J=8.4 Hz), 6.89(d, 2H, J=8.4 Hz), 6.68(d, 1H, J=8.6 Hz), 6.49(m, 1H), 6.35(d, 1H, J=2.8 Hz), 6.27(d, 1H, J=9.7 Hz), 5.63(d, 1H, J=9.7 Hz), 4.20(s, 2H), 4.05(q, 2H, J=6.9 Hz), 3.57(br, 1H), 1.48-1.40(m, 9H); m/z: 309.31 |
| 1-27 | 2,5-Di-Me-Bn | H | H | 0 | Me | ¹H NMR(500 MHz, CDCl₃) δ 7.10(s, 1H), 6.97(s, 2H), 6.86(dd, 1H, J=8.6 Hz, J=2.5 Hz), 6.79(d, 1H, J=2.5 Hz), 6.67(d, 1H, J=8.6 Hz), 6.22(d, 1H, J=9.8 Hz), 5.64(d, 1H, J=9.8 Hz), 4.21(s, 2H), 2.22(s, 3H), 2.11(s, 3H), 1.40(s, 6H); m/z: 293.31 |
| 1-28 | 2,6-Di-Me-Bn | H | H | 0 | Me | ¹H NMR(200 MHz, CDCl₃) 7.07-6.93(m, 5H), 6.68(d, 1H, J=8.6 Hz), 6.21(d, 1H, J=9.8 Hz), 5.61(d, 1H, J=9.8 Hz), 4.20(s, 2H), 2.18(s, 3H), 2.04(s, 3H), 1.40(s, 6H); m/z: 293.40 |
| 1-29 | 4-Br—2-F-Bn | H | H | 0 | Me | ¹H NMR(500 MHz, CDCl₃) δ 7.23(m, 3H), 6.63(d, 1H, J=9.3 Hz), 6.46(dd, 1H, J=9.3 Hz, J=3.0 Hz), 6.34(d, 1H, J=3.0 Hz), 6.22(d, 1H, J=9.6 Hz), 5.61(d, 1H, J=9.8 Hz), 4.29(s, 2H), 1.39(s, 6H); m/z: 362.14 |
| 1-30 | — | H | H | 0 | Me | m/z: 266.26 |

TABLE 1-continued

| Compound No. | R¹ | R² | R³ | n | R⁴ | NMR & Mass analytic results |
|---|---|---|---|---|---|---|
| 1-31 | (pyridin-3-ylmethyl, gem-dimethyl) | H | H | 0 | Me | m/z: 266.27 |
| 1-32 | (pyridin-4-ylmethyl, gem-dimethyl) | H | H | 0 | Me | ¹H NMR(200 MHz, CDCl₃) δ 8.55(d, 2H, J=5.2 Hz), 7.30(d, 2H, J=5.2 Hz), 6.63(d, 1H, J=8.2 Hz), 6.38(dd, 1H, J=8.2 Hz, J=2.6 Hz), 6.25(d, 1H, J=2.6 Hz), 6.25(d, 1H, J=2.5 Hz), 6.20(d, 1H, J=10.0 Hz), 5.60(d, 1H, J=10.0 Hz), 4.32(s, 2H), 1.39(s, 6H); m/z: 266.31 |
| 1-33 | (1,3-dioxolanyl-vinyl-CH=CH-CH₂-) | H | H | 0 | Me | m/z: 309.37 |
| 1-34 | (thien-2-ylmethyl) | H | H | 0 | Me | m/z: 271.17 |
| 1-35 | (thien-3-ylmethyl) | H | H | 0 | Me | ¹H NMR(200 MHz, CDCl₃) δ 7.34-7.30(m, 1H), 7.20(m, 1H), 7.12-7.08(m, 1H), 6.69(d, 1H, J=8.5 Hz), 6.498(dd, 1H, J=8.5 Hz, J=2.8 Hz), 6.37(d, 1H, J=2.8 Hz), 6.28(d, 1H, J=9.8 Hz), 5.64(d, 1H, J=9.8 Hz), 4.29(s, 2H), 3.58(br, 1H), 1.44(s, 6H); m/z: 271.14 |
| 1-36 | (5-methylthien-2-ylmethyl) | H | H | 0 | Me | m/z: 285.36 |
| 1-37 | (5-nitrofuran-2-ylmethyl) | H | H | 0 | Me | m/z: 300.35 |
| 1-38 | (naphthalen-2-ylmethyl) | H | H | 0 | Me | ¹H NMR(500 MHz, CDCl₃) δ 7.81(m, 4H), 7.47(m, 3H), 6.66(d, 1H, J=8.6 Hz), 6.57(d, 1H, J=2.8 Hz), 6.46(d, 1H, J=2.78 Hz), 6.23(d, 1H, J=9.8 Hz), 5.61(d, 1H, J=9.8 Hz), 4.41(s, 2H), 1.41(s, 6H); m/z: 315.32 |
| 1-39 | (indol-2-ylmethyl) | H | H | 0 | Me | ¹H NMR(300 MHz, CDCl₃) δ 7.65(d, 1H, J=7.7 Hz), 7.31(d, 1H, J=8.0 Hz), 7.21-7.06(m, 3H), 6.68(d, 1H, J=8.50 Hz), 6.49(dd, 1H, J=8.5 Hz, J=2.8 Hz), 6.37(d, 1H, J=2.8 Hz), 6.25(d, 1H, J=9.7 Hz), 5.60(d, 1H, J=9.7 Hz), 4.39(s, 2H), 1.40(s, 6H); m/z: 304.26 |
| 1-40 | PhEt | H | H | 0 | Me | ¹H NMR(300 MHz, CDCl₃) 7.25(m, 5H), 6.68-6.23(m, 4H), 3.35(t, 2H), 2.91(t, 2H), 1.40(s, 6H); m/z: 279.35 |
| 1-41 | Bn | H | H | 1 | Me | ¹H NMR(200 MHz, CDCl₃) δ 7.30-7.19(m, 5H), 6.57(d, 1H, J=8.6 Hz), 6.38(dd, 1H, J=8.6 Hz, J=2.6 Hz), 6.26(d, 1H, J=2.6 Hz), 6.21(d, 1H, J=10.0 Hz), 5.50(d, 1H, J=10.0 Hz), 4.20(s, 2H), 1.62(q, 2H, J=7.5 Hz), 1.27(s, 3H), 0.88(t, 3H, J=7.5 Hz); m/z: 279.34 |
| 1-42 | 2-MeO-Bn | H | H | 1 | Me | m/z: 309.31 |
| 1-43 | 3-MeO-Bn | H | H | 1 | Me | m/z: 309.39 |
| 1-44 | 4-MeO-Bn | H | H | 1 | Me | m/z: 309.36 |
| 1-45 | 2-t-Bu-Bn | H | H | 1 | Me | m/z: 335.29 |

TABLE 1-continued

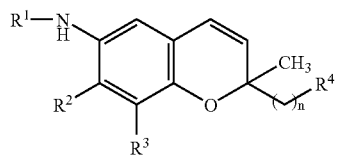

(1)

| Compound No. | R¹ | R² | R³ | n | R⁴ | NMR & Mass analytic results |
|---|---|---|---|---|---|---|
| 1-46 | 3-t-Bu-Bn | H | H | 1 | Me | m/z: 335.31 |
| 1-47 | 4-t-Bu-Bn | H | H | 1 | Me | m/z: 335.35 |
| 1-48 | 2-Me-Bn | H | H | 1 | Me | m/z: 293.31 |
| 1-49 | 3-Me-Bn | H | H | 1 | Me | m/z: 293.30 |
| 1-50 | 4-Me-Bn | H | H | 1 | Me | m/z: 293.32 |
| 1-51 | 2-F-Bn | H | H | 1 | Me | m/z: 297.36 |
| 1-52 | 3-F-Bn | H | H | 1 | Me | m/z: 297.34 |
| 1-53 | 4-F-Bn | H | H | 1 | Me | m/z: 297.38 |
| 1-54 | 2-Cl-Bn | H | H | 1 | Me | m/z: 313.80 |
| 1-55 | 3-Cl-Bn | H | H | 1 | Me | m/z: 313.73 |
| 1-56 | 4-Cl-Bn | H | H | 1 | Me | m/z: 313.81 |
| 1-57 | 2-CN-Bn | H | H | 1 | Me | m/z: 304.44 |
| 1-58 | 3-CN-Bn | H | H | 1 | Me | m/z: 304.30 |
| 1-59 | 4-CN-Bn | H | H | 1 | Me | m/z: 304.41 |
| 1-60 | 2-NO₂-Bn | H | H | 1 | Me | m/z: 324.37 |
| 1-61 | 3-NO₂-Bn | H | H | 1 | Me | m/z: 324.34 |
| 1-62 | 4-NO₂-Bn | H | H | 1 | Me | m/z: 324.34 |
| 1-63 | 2-CF₃-Bn | H | H | 1 | Me | m/z: 347.42 |
| 1-64 | 3-CF₃-Bn | H | H | 1 | Me | m/z: 347.47 |
| 1-65 | 4-CF₃-Bn | H | H | 1 | Me | m/z: 347.34 |
| 1-66 | 4-EtO-Bn | H | H | 1 | Me | m/z: 323.14 |
| 1-67 | 2,5-Di-Me-Bn | H | H | 1 | Me | m/z: 307.74 |
| 1-68 | 2,6-Di-Me-Bn | H | H | 1 | Me | m/z: 307.24 |
| 1-69 | 4-Br—2-F-Bn | H | H | 1 | Me | m/z: 376.37 |
| 1-70 | (2-pyridyl)methyl | H | H | 1 | Me | m/z: 280.47 |
| 1-71 | (3-pyridyl)methyl | H | H | 1 | Me | m/z: 280.21 |
| 1-72 | (4-pyridyl)methyl | H | H | 1 | Me | m/z: 280.30 |
| 1-73 | (1,3-benzodioxol-5-yl)methyl | H | H | 1 | Me | m/z: 323.45 |
| 1-74 | (2-thienyl)methyl | H | H | 1 | Me | m/z: 285.31 |
| 1-75 | (3-thienyl)methyl | H | H | 1 | Me | m/z: 285.21 |
| 1-76 | (5-methyl-2-thienyl)methyl | H | H | 1 | Me | m/z: 299.40 |

TABLE 1-continued

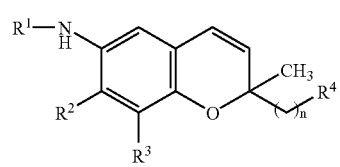

(1)

| Compound No. | R¹ | R² | R³ | n | R⁴ | NMR & Mass analytic results |
|---|---|---|---|---|---|---|
| 1-77 | (5-nitrofuran-2-yl)methyl-C(Me)— | H | H | 1 | Me | m/z: 314.30 |
| 1-78 | (naphthalen-2-yl)methyl-C(Me)— | H | H | 1 | Me | m/z: 329.25 |
| 1-79 | (1H-indol-2-yl)methyl-C(Me)— | H | H | 1 | Me | m/z: 318.40 |
| 1-80 | PhEt | H | H | 1 | Me | m/z: 293.40 |
| 1-81 | Bn | H | H | 2 | Me | ¹H NMR(200 MHz, CDCl₃) δ 7.28-7.23(m, 5H), 7.02-6.92(m, 2H), 6.66(d, 1H, J=8.5 Hz), 6.23(d, 1H, J=10.0 Hz), 5.59(d, 1H, J=10.0 Hz), 4.22(s, 2H), 1.70-1.57(m, 2H), 1.50-1.26(m, 2H), 1.36(s, 3H), 0.90(t, 3H, J=7.0 Hz); m/z: 293.43 |
| 1-82 | 2-MeO-Bn | H | H | 2 | Me | m/z: 323.42 |
| 1-83 | 3-MeO-Bn | H | H | 2 | Me | m/z: 323.42 |
| 1-84 | 4-MeO-Bn | H | H | 2 | Me | m/z: 323.41 |
| 1-85 | 2-t-Bu-Bn | H | H | 2 | Me | m/z: 349.42 |
| 1-86 | 3-t-Bu-Bn | H | H | 2 | Me | m/z: 349.42 |
| 1-87 | 4-t-Bu-Bn | H | H | 2 | Me | ¹H NMR(200 MHz, CDCl₃) δ 7.39-7.27(m, 4H), 6.65(d, 1H, J=8.5 Hz), 6.58-6.53(m, 1H), 6.44(m, 1H), 6.27(d, 1H, J=10.0 Hz), 5.57(d, 1H, J=10.0 Hz), 4.80(br, 1H), 4.22(s, 2H), 1.71-1.60(m, 2H), 1.54-1.23(m, 2H), 1.32(s, 3H), 1.31(s, 3H), 0.92(t, 3H, J=7.1 Hz); m/z: 349.57 |
| 1-88 | 2-Me-Bn | H | H | 2 | Me | ¹H NMR(200 MHz, CDCl₃) δ 7.33-7.26(m, 1H), 7.20-7.14(m, 3H), 6.65(s, 2H), 6.55(s, 1H), 6.26(d, 1H, J=9.8 Hz), 5.59(d, 1H, J=9.8 Hz), 4.25(s, 2H), 2.29(s, 3H), 1.71-1.59(m, 2H), 1.51-1.27(m, 2H), 1.36(s, 3H), 0.92(t, 3H, J=7.1 Hz); m/z: 307.41 |
| 1-89 | 3-Me-Bn | H | H | 2 | Me | m/z: 307.24 |
| 1-90 | 4-Me-Bn | H | H | 2 | Me | ¹H NMR(200 MHz, CDCl₃) δ 7.16(d, 2H, J=6.5 Hz), 7.06(d, 2H, J=6.5 Hz), 6.88-6.78(m, 2H), 6.65(d, 1H, J=8.3 Hz), 6.25(d, 1H, J=9.8 Hz), 5.59(d, 1H, J=9.8 Hz), 4.17(s, 2H), 2.26(s, 3H), 1.70-1.58(m, 2H), 1.51-1.27(m, 2H), 1.35(s, 3H), 0.96-0.87(m, 3H); m/z: 307.40 |
| 1-91 | 2-F-Bn | H | H | 2 | Me | m/z: 311.44 |
| 1-92 | 3-F-Bn | H | H | 2 | Me | ¹H NMR(200 MHz, CDCl₃) δ 7.35-7.25(m, 1H), 7.17-7.07(m, 2H), 7.00-6.91(m, 1H), 6.63(d, 1H, J=8.5 Hz), 6.46-6.40(m, 1H), 6.31(d, 1H, J=8.5 Hz), 6.46-6.40(m, 1H), 6.31(d, 1H, J=2.8 Hz), 6.25(d, 1H, J=9.9 Hz), 5.57(d, 1H, J=9.9 Hz), 4.28(s, 2H), 3.38(br, 1H), 1.70-1.59(m, 2H), 1.53-1.40(m, 2H), 1.35(s, 3H), 0.91(t, 3H, J=7.1 Hz); m/z: 311.30 |
| 1-93 | 4-F-Bn | H | H | 2 | Me | ¹H NMR(200 MHz, CDCl₃) δ 7.37-7.30(m, 2H), 7.06-6.97(m, 2H), 6.63(d, 1H, J=8.5 Hz), 6.46(dd, 1H, J=8.5 Hz, J=2.8 Hz), 6.35(d, 1H, J=2.8 Hz), 6.26(d, 1H, J=9.9 Hz), 5.57(d, 1H, J=9.9 Hz), 4.24(s, 2H), 3.6(br, 1H), 1.70-1.59(m, 2H), 1.53-1.26(m, 2H), 1.35(s, 3H), 0.91(t, 3H, J=7.1Hz); m/z: 311.43 |
| 1-94 | 2-Cl-Bn | H | H | 2 | Me | m/z: 327.56 |

TABLE 1-continued

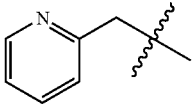

| Compound No. | R¹ | R² | R³ | n | R⁴ | NMR & Mass analytic results |
|---|---|---|---|---|---|---|
| 1-95 | 3-Cl-Bn | H | H | 2 | Me | $^1$H NMR(200 MHz, CDCl$_3$) δ 7.42-7.34(m, 1H), 7.27-7.23(m, 3H), 6.64(d, 1H, J=8.5 Hz), 6.57-6.51(m, 1H), 6.44-6.42(m, 1H), 6.26(d, 1H, J=10.0 Hz), 5.57(d, 1H, J=10.0 Hz), 4.25(s, 2H), 1.71-1.59(m, 2H), 1.50-1.27(m, 2H), 1.36(s, 3H), 0.97-0.94(m, 3H); m/z: 327.76 |
| 1-96 | 4-Cl-Bn | H | H | 2 | Me | m/z: 327.66 |
| 1-97 | 2-CN-Bn | H | H | 2 | Me | m/z: 318.52 |
| 1-98 | 3-CN-Bn | H | H | 2 | Me | m/z: 318.45 |
| 1-99 | 4-CN-Bn | H | H | 2 | Me | m/z: 318.44 |
| 1-100 | 2-NO$_2$-Bn | H | H | 2 | Me | m/z: 338.31 |
| 1-101 | 3-NO$_2$-Bn | H | H | 2 | Me | m/z: 338.40 |
| 1-102 | 4-NO$_2$-Bn | H | H | 2 | Me | m/z: 338.39 |
| 1-103 | 2-CF$_3$-Bn | H | H | 2 | Me | m/z: 361.44 |
| 1-104 | 3-CF$_3$-Bn | H | H | 2 | Me | m/z: 361.51 |
| 1-105 | 4-CF$_3$-Bn | H | H | 2 | Me | m/z: 361.61 |
| 1-106 | 4-EtO-Bn | H | H | 2 | Me | m/z: 337.43 |
| 1-107 | 2,5-Di-Me-Bn | H | H | 2 | Me | m/z: 321.27 |
| 1-108 | 2,6-Di-Me-Bn | H | H | 2 | Me | m/z: 321.44 |
| 1-109 | 4-Br—2-F-Bn | H | H | 2 | Me | m/z: 390.70 |
| 1-110 | 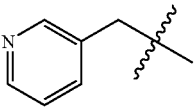 | H | H | 2 | Me | m/z: 294.50 |
| 1-111 | 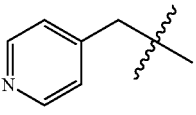 | H | H | 2 | Me | m/z: 294.44 |
| 1-112 | 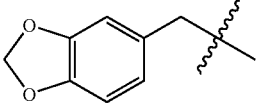 | H | H | 2 | Me | m/z: 294.41 |
| 1-113 | 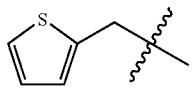 | H | H | 2 | Me | m/z: 337.34 |
| 1-114 | 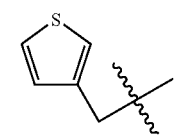 | H | H | 2 | Me | m/z: 299.24 |
| 1-115 | 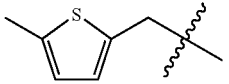 | H | H | 2 | Me | m/z: 299.14 |
| 1-116 |  | H | H | 2 | Me | m/z: 313.37 |

TABLE 1-continued (1)

| Compound No. | R¹ | R² | R³ | n | R⁴ | NMR & Mass analytic results |
|---|---|---|---|---|---|---|
| 1-117 | 5-nitro-2-furylmethyl | H | H | 2 | Me | m/z: 328.25 |
| 1-118 | polyenyl (decatetraenyl) | H | H | 2 | Me | m/z: 332.20 |
| 1-119 | indol-3-ylmethyl | H | H | 2 | Me | m/z: 307.14 |
| 1-120 | PhEt | H | H | 2 | Me | m/z: 307.23 |
| 1-121 | Bn | H | H | 2 | Ph | $^1$H NMR(200 MHz, CDCl$_3$) δ 8.07(m, 2H), 7.18(m, 8H), 6.86(dd, 1H, J=8.6 Hz, J=2.8 Hz), 6.77(d, 1H, J=2.8 Hz), 6.67(d, 1H, J=8.6 Hz), 6.28(d, 1H, J=10.0 Hz), 5.62(d, 1H, J=10.0 Hz), 4.21(s, 2H), 2.72(m, 2H), 1.95(m, 2H), 1.40(s, 3H); m/z: 355.41 |
| 1-122 | 2-MeO-Bn | H | H | 2 | Ph | m/z: 385.24 |
| 1-123 | 3-MeO-Bn | H | H | 2 | Ph | m/z: 385.22 |
| 1-124 | 4-MeO-Bn | H | H | 2 | Ph | $^1$H NMR(300 MHz, CDCl$_3$) δ 7.30-7.22(m, 5H), 7.15(d, 2H), 6.87(m, 2H), 6.66(d, 1H), 6.45(dd, 1H), 6.32(d, 1H), 6.30(d, 1H), 5.59(d, 1H, J=9.8 Hz), 4.17(s, 2H), 3.78(s, 3H), 2.74(m, 2H), 1.94(m, 2H), 1.40(s, 3H); m/z: 385.34 |
| 1-125 | 2-t-Bu-Bn | H | H | 2 | Ph | m/z: 411.28 |
| 1-126 | 3-t-Bu-Bn | H | H | 2 | Ph | m/z: 411.65 |
| 1-127 | 4-t-Bu-Bn | H | H | 2 | Ph | m/z: 411.51 |
| 1-128 | 2-Me-Bn | H | H | 2 | Ph | m/z: 369.57 |
| 1-129 | 3-Me-Bn | H | H | 2 | Ph | m/z: 369.54 |
| 1-130 | 4-Me-Bn | H | H | 2 | Ph | m/z: 369.52 |
| 1-131 | 2-F-Bn | H | H | 2 | Ph | $^1$H NMR(300 MHz, CDCl$_3$) δ 7.35(m, 1H), 7.26-7.05(m, 8H), 6.65(d, 1H, J=8.5 Hz), 6.43(dd, 1H, J=8.50 Hz, J=2.8 Hz), 6.30(d, 1H, J=2.8 Hz), 6.28(d, 1H, J=9.8 Hz), 5.57(d, 1H, J=9.8 Hz), 4.30(s, 2H), 2.73(m, 2H), 1.97(m, 2H), 1.38(s, 3H); m/z: 373.47 |
| 1-132 | 3-F-Bn | H | H | 2 | Ph | m/z: 373.58 |
| 1-133 | 4-F-Bn | H | H | 2 | Ph | m/z: 373.55 |
| 1-134 | 2-Cl-Bn | H | H | 2 | Ph | m/z: 389.84 |
| 1-135 | 3-Cl-Bn | H | H | 2 | Ph | m/z: 389.56 |
| 1-136 | 4-Cl-Bn | H | H | 2 | Ph | m/z: 389.65 |
| 1-137 | 2-CN-Bn | H | H | 2 | Ph | $^1$H NMR(300 MHz, CDCl$_3$) δ 7.95(d, 1H, J=7.5 Hz), 7.50(m, 2H), 7.38(d, 1H, J=7.5 Hz), 7.25-7.15(m, 6H), 7.09(d, 1H, J=2.4 Hz), 6.79(d, 1H, J=8.4 Hz), 6.40(d, 1H, J=9.6 Hz), 5.60(d, 1H, J=9.6 Hz), 5.40(s, 2H), 2.82-2.73(m, 2H), 2.08-1.89(m, 2H), 1.44(s, 3H); m/z: 380.26 |
| 1-138 | 3-CN-Bn | H | H | 2 | Ph | m/z: 380.38 |
| 1-139 | 4-CN-Bn | H | H | 2 | Ph | $^1$H NMR(300 MHz, CDCl$_3$) δ 7.60(d, 2H, J=8.0 Hz), 7.47(d, 2H, J=8.0 Hz), 7.23(d, 2H, J=6.6 Hz), 7.15(m, 3H), 6.65(d, 1H, J=8.4 Hz), 6.38(dd, 1H, J=8.4 Hz, J=2.7 Hz), 6.27(d, 1H, J=9.9 Hz), 6.25(d, 1H, J=2.7 Hz), 5.61(d, 1H, J=9.9 Hz), 4.35(s, 2H), 3.87(br-s, 1H), 2.78-2.67(m, 2H), 2.00-1.90(m, 2H), 1.40(s, 3H); m/z: 380.87 |
| 1-140 | 2-NO$_2$-Bn | H | H | 2 | Ph | m/z: 400.85 |
| 1-141 | 3-NO$_2$-Bn | H | H | 2 | Ph | m/z: 400.26 |

TABLE 1-continued

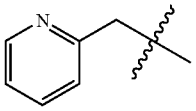

| Compound No. | R¹ | R² | R³ | n | R⁴ | NMR & Mass analytic results |
|---|---|---|---|---|---|---|
| 1-142 | 4-NO$_2$-Bn | H | H | 2 | Ph | $^1$H NMR(300 MHz, CDCl$_3$) δ 8.15(m, 2H, J=8.6 Hz), 7.50(d, 2H, J=8.6 Hz), 7.24(m, 2H), 7.14(m, 3H), 6.64(d, 1H, J=8.5 Hz), 6.37(dd, 1H, J=8.5 Hz, J=2.8 Hz), 6.26(d, 1H, J=9.8 Hz), 6.24(d, 1H, J=2.8 Hz), 5.60(d, 1H, J=9.8 Hz), 4.37(s, 2H), 2.72(m, 2H), 1.96(m, 2H), 1.39(s, 3H); m/z: 400.40 |
| 1-143 | 2-CF$_3$-Bn | H | H | 2 | Ph | m/z: 423.28 |
| 1-144 | 3-CF$_3$-Bn | H | H | 2 | Ph | m/z: 423.48 |
| 1-145 | 4-CF$_3$-Bn | H | H | 2 | Ph | m/z: 423.58 |
| 1-146 | 4-EtO-Bn | H | H | 2 | Ph | $^1$H NMR(200 MHz, CDCl$_3$) δ 7.32-7.08(m, 7H), 6.84(d, 2H, J=8.6 Hz), 6.65(d, 1H, J=8.5 Hz), 6.42(dd, 1H, J=8.50 Hz, J=2.6 Hz), 6.31(d, 1H, J=2.6 Hz,), 6.28(d, 1H, J=9.8 Hz), 5.57(d, 1H, J=9.8 Hz), 4.14(s, 2H), 3.98(q, 2H, J=7.1 Hz), 2.73(m, 2H), 1.94(m, 2H), 1.38(s, 3H), 1.38(t, 3H, J=7.1 Hz); m/z: 399.74 |
| 1-147 | 2,5-Di-Me-Bn | H | H | 2 | Ph | m/z: 383.24 |
| 1-148 | 2,6-Di-Me-Bn | H | H | 2 | Ph | m/z: 383.24 |
| 1-149 | 4-Br—2-F-Bn | H | H | 2 | Ph | m/z: 452.54 |
| 1-150 | 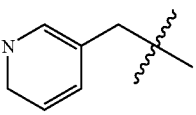 | H | H | 2 | Ph | m/z: 356.74 |
| 1-151 | 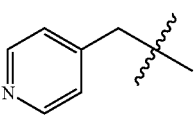 | H | H | 2 | Ph | m/z: 356.51 |
| 1-152 | 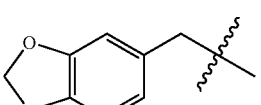 | H | H | 2 | Ph | m/z: 356.14 |
| 1-153 | 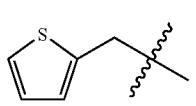 | H | H | 2 | Ph | m/z: 399.50 |
| 1-154 | 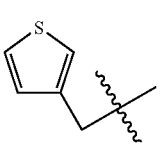 | H | H | 2 | Ph | $^1$H NMR(200 MHz, CDCl$_3$) δ 7.29-7.22(m, 6H), 7.19-6.90(m, 2H), 6.70(d, 1H, J=9.7 Hz), 6.58-6.40(m, 1H), 6.40-6.32(m, 2H), 6.64(d, 1H, J=9.8 Hz), 4.47(s, 2H), 3.60-3.20(br, 1H), 2.80-2.60(m, 2H), 2.10-1.80(m, 2H), 1.44(s, 3H)m/z: 361.52 |
| 1-155 | 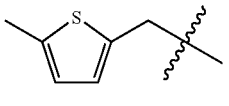 | H | H | 2 | Ph | $^1$H NMR(200 MHz, CDCl$_3$) δ 7.28-7.10(m, 7H), 7.04(dd, 1H, J=4.8 Hz, J=1.2 Hz), 6.67(d, 1H, J=8.6 Hz), 6.44(dd, 1H, J=8.6 Hz, J=2.8 Hz), 6.30(m, 2H), 5.59(d, 1H, J=9.6 Hz), 4.23(s, 2H), 3.53(br, 1H), 2.80-2.69(m, 2H), 2.06-1.89(m, 2H), 1.39(s, 3H); m/z: 361.27 |
| 1-156 | 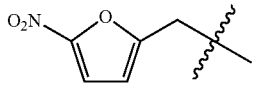 | H | H | 2 | Ph | $^1$H NMR(200 MHz, CDCl$_3$) δ 7.27-7.16(m, 5H), 6.77-6.60(m, 1H), 6.60-6.40(m, 1H), 6.38-6.31(m, 2H), 5.61(d, 1H, J=10.2 Hz), 5.17(s, 1H), 4.37(s, 2H), 2.90-2.80(m, 2H), 2.45(s, 3H), 2.07-1.80(m, 2H), 1.42(s, 3H)m/z: 375.77 |
| 1-157 | O$_2$N—furan— | H | H | 2 | Ph | m/z: 390.21 |

TABLE 1-continued (Structure: chromene with R¹-NH at position 6, CH₃ and (CH₂)ₙR⁴ at position 2, R² at position 7, R³ at position 8)

| Compound No. | R¹ | R² | R³ | n | R⁴ | NMR & Mass analytic results |
|---|---|---|---|---|---|---|
| 1-158 | (2-naphthylmethyl, gem-dimethyl) | H | H | 2 | Ph | m/z: 405.65 |
| 1-159 | (indol-2-ylmethyl, gem-dimethyl) | H | H | 2 | Ph | m/z: 394.14 |
| 1-160 | PhEt | H | H | 2 | Ph | m/z: 369.04 |
| 1-161 | Bn | H | H | 2 | 4-MeO-Ph | ¹H NMR(200 MHz, CDCl₃) δ 7.40-7.25(m, 5H), 7.08(d, 2H, J=8.5 Hz), 6.80(d, 2H, J=8.5 Hz), 6.67(d, 1H, J=8.5 Hz), 6.46(dd, 1H, J=8.5 Hz, J=2.5 Hz), 6.35-6.28(m, 2H), 5.60(d, 1H, J=9.8 Hz), 4.28(s, 2H), 3.78(s, 3H), 2.72-2.61(m, 2H), 1.99-1.87(m, 2H), 1.40(s, 3H); m/z: 385.27 |
| 1-162 | 2-MeO-Bn | H | H | 2 | 4-MeO-Ph | ¹H NMR(200 MHz, CDCl₃) δ 7.34-7.21(m, 2H), 7.09(d, 2H, J=8.6 Hz), 7.05-6.88(m, 2H), 6.81(d, 2H, J=8.7 Hz), 6.66(d, 1H, J=8.5 Hz), 6.49(dd, 1H, J=8.5 Hz, J=2.8 Hz), 6.37-6.29(m, 2H), 5.59(d, 1H, J=9.7 Hz), 4.28(s, 2H), 3.87(s, 3H), 3.78(s, 3H), 2.76-2.61(m, 2H), 1.99-1.88(m, 2H), 1.40(s, 3H); m/z: 415.82 |
| 1-163 | 3-MeO-Bn | H | H | 2 | 4-MeO-Ph | ¹H NMR(200 MHz, CDCl₃) δ 7.31-7.23(m, 1H), 7.09(d, 2H, J=8.5 Hz), 7.06-6.94(m, 2H), 6.85-6.77(m, 3H), 6.67(d, 1H, J=8.5 Hz), 6.46(dd, 1H, J=8.5 Hz, J=2.8 Hz), 6.35-6.28(m, 2H), 5.61(d, 1H, J=9.8 Hz), 4.26(s, 2H), 3.80(s, 3H), 3.78(s, 3H), 2.76-2.61(m, 2H), 2.00-1.88(m, 2H), 1.41(s, 3H); m/z: 415.74 |
| 1-164 | 4-MeO-Bn | H | H | 2 | 4-MeO-Ph | ¹H NMR(200 MHz, CDCl₃) δ 7.29(d, 2H, J=8.5 Hz), 7.08(d, 2H, J=8.5 Hz), 6.88(d, 2H, J=8.5 Hz), 6.80(d, 2H, J=8.5 Hz), 6.66(d, 1H, J=8.5 Hz), 6.46(dd, 1H, J=8.5 Hz, J=2.5 Hz), 6.35-6.29(m, 2H), 5.60(d, 1H, J=9.8 Hz), 4.20(s, 2H), 3.81(s, 3H), 3.78(s, 3H), 2.75-2.61(m, 2H), 1.99-1.87(m, 2H), 1.40(s, 3H); m/z: 415.04 |
| 1-165 | 2-t-Bu-Bn | H | H | 2 | 4-MeO-Ph | m/z: 441.17 |
| 1-166 | 3-t-Bu-Bn | H | H | 2 | 4-MeO-Ph | m/z: 441.67 |
| 1-167 | 4-t-Bu-Bn | H | H | 2 | 4-MeO-Ph | ¹H NMR(200 MHz, CDCl₃) δ 7.40-7.26(m, 4H), 7.08(d, 2H, J=8.7 Hz), 6.80(d, 2H, J=8.7 Hz), 6.67(d, 1H, J=8.5 Hz), 6.47(dd, 1H, J=8.5 Hz, J=2.7 Hz), 6.36-6.29(m, 2H), 5.60(d, 1H, J=9.8 Hz), 4.23(s, 2H), 3.78(s, 3H), 2.75-2.62(m, 2H), 1.99-1.87(m, 2H), 1.40(s, 3H), 1.32(s, 9H); m/z: 441.47 |
| 1-168 | 2-Me-Bn | H | H | 2 | 4-MeO-Ph | m/z: 399.10 |
| 1-169 | 3-Me-Bn | H | H | 2 | 4-MeO-Ph | m/z: 399.35 |
| 1-170 | 4-Me-Bn | H | H | 2 | 4-MeO-Ph | ¹H NMR(200 MHz, CDCl₃) δ 7.29-7.25(m, 2H), 7.15(d, 2H, J=8.1 Hz), 7.08(d, 2H, J=8.5 Hz), 6.80(d, 2H, J=8.5 Hz), 6.66(d, 1H, J=8.5 Hz), 6.46(dd, 1H, J=8.5 Hz, J=2.8 Hz), 6.35-6.28(m, 2H), 5.60(d, 1H, J=9.8 Hz), 4.23(s, 2H), 3.78(s, 3H), 2.75-2.61(m, 2H), 2.35(s, 3H), 1.99-1.87(m, 2H), 1.40(s, 3H); m/z: 399.40 |
| 1-171 | 2-F-Bn | H | H | 2 | 4-MeO-Ph | ¹H NMR(200 MHz, CDCl₃) δ 7.43-7.35(m, 1H), 7.30-7.20(m, 1H), 7.13-7.01(m, 4H), 6.80(d, 2H, J=8.9 Hz), 6.66(d, 1H, J=8.5 Hz), 6.47(dd, 1H, J=8.5 Hz, J=2.8 Hz), 6.35-6.28(m, 2H), 5.60(d, 1H, J=9.8 Hz), 4.35(s, 2H), 3.78(s, 3H), 2.75-2.01(m, 2H), 1.99-1.87(m, 2H), 1.40(s, 3H); m/z: 403.77 |
| 1-172 | 3-F-Bn | H | H | 2 | 4-MeO-Ph | ¹H NMR(200 MHz, CDCl₃) δ 7.33-7.26(m, 1H), 7.25-7.06(m, 4H), 7.05-6.96(m, 1H), 6.83-6.78(m, 2), 6.65(d, 1H, J=8.5 Hz), 6.43(dd, 1H, J=8.5 Hz, J=2.8 Hz), 6.32-6.27(m, 2H), 5.60(d, 1H, J=10.1 Hz), 4.28(s, 2H), 3.78(s, 3H), 2.75-2.61(m, 2H), 1.99-1.87(m, 2H), 1.40(s, 3H); m/z: 403.52 |

TABLE 1-continued

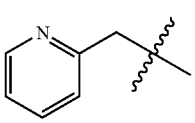

| Compound No. | R¹ | R² | R³ | n | R⁴ | NMR & Mass analytic results |
|---|---|---|---|---|---|---|
| 1-173 | 4-F-Bn | H | H | 2 | 4-MeO-Ph | $^1$H NMR(200 MHz, CDCl$_3$) δ 7.37-7.26(m, 2H), 7.10-6.98(m, 4H), 6.80(d, 2H, J=8.7 Hz), 6.66(d, 1H, J=8.5 Hz), 6.45(dd, 1H, J=8.5 Hz, J=2.5 Hz), 6.33-6.27(m, 2H), 560(d, 1H, J=9.8 Hz), 4.24(s, 2H), 3.78(s, 3H), 2.75-2.61(m, 2H), 1.99-1.87(m, 2H), 1.40(s, 3H); m/z: 403.04 |
| 1-174 | 2-Cl-Bn | H | H | 2 | 4-MeO-Ph | $^1$H NMR(200 MHz, CDCl$_3$) δ 7.45-7.36(m, 2H), 7.24-7.19(m, 2H), 7.08(d, 2H, J=8.8 Hz), 6.80(d, 2H, J=8.8 Hz), 6.66(d, 1H, J=8.6 Hz), 6.44(dd, 1H, J=8.6 Hz, J=2.9 Hz), 6.32-6.28(m, 2H), 5.60(d, 1H, J=9.8 Hz), 4.38(s, 2H), 3.78(s, 3H), 2.75-2.61(m, 2H), 1.99-1.87(m, 2H), 1.40(s, 3H); m/z: 419.71 |
| 1-175 | 3-Cl-Bn | H | H | 2 | 4-MeO-Ph | $^1$H NMR(200 MHz, CDCl$_3$) δ 7.37(s, 1H), 7.26(s, 3H), 7.08(d, 2H, J=8.5 Hz), 6.80(d, 2H, J=8.5 Hz), 6.66(d, 1H, J=8.5 Hz), 6.43(dd, 1H, J=8.5 Hz, J=2.8 Hz), 6.32-6.27(m, 2H), 5.60(d, 1H, J=9.8 Hz), 4.26(s, 2H), 3.78(s, 3H), 2.75-2.61(m, 2H), 1.99-1.87(m, 2H), 1.40(s, 3H); m/z: 419.52 |
| 1-176 | 4-Cl-Bn | H | H | 2 | 4-MeO-Ph | $^1$H NMR(200 MHz, CDCl$_3$) δ 7.30(s, 4H), 7.08(d, 2H, J=8.5 Hz), 6.80(d, 2H, J=8.5 Hz), 6.65(d, 1H, J=8.5 Hz), 6.46(dd, 1H, J=8.3 Hz, J=2.7 Hz), 6.33(d, 1H, J=2.7 Hz), 6.29(d, 1H, J=9.8 Hz), 5.60(d, 1H, J=9.8 Hz), 4.25(s, 2H), 3.77(s, 3H), 2.71-2.62(m, 2H), 1.98-1.90(m, 2H), 1.39(s, 3H); m/z: 419.94 |
| 1-177 | 2-CN-Bn | H | H | 2 | 4-MeO-Ph | m/z: 410.41 |
| 1-178 | 3-CN-Bn | H | H | 2 | 4-MeO-Ph | m/z: 410.52 |
| 1-179 | 4-CN-Bn | H | H | 2 | 4-MeO-Ph | m/z: 410.52 |
| 1-180 | 2-NO$_2$-Bn | H | H | 2 | 4-MeO-Ph | $^1$H NMR(200 MHz, CDCl$_3$) δ 8.08-8.02(m, 1H), 7.70-7.61(m, 1H), 7.60-7.52(m, 1H), 7.45-7.41(m, 1H), 7.07(d, 2H, J=8.7 Hz), 6.79(d, 2H, J=8.7 Hz), 6.63(d, 1H, J=8.5 Hz), 6.38(dd, 1H, J=8.5 Hz, J=2.8 Hz), 6.29-6.24(m, 2H), 5.59(d, 1H, J=10.2 Hz), 4.65(s, 2H), 3.77(s, 3H), 2.73-2.61(m, 2H), 1.98-1.86(m, 2H), 1.39(s, 3H); m/z: 430.21 |
| 1-181 | 3-NO$_2$-Bn | H | H | 2 | 4-MeO-Ph | $^1$H NMR(200 MHz, CDCl$_3$) δ 8.25(s, 1H), 8.12(d, 1H, J=8.5 Hz), 7.71(d, 1H, J=7.7 Hz), 7.50(t, 1H, 17.7 Hz), 7.07(d, 2H, J=8.5 Hz), 6.80(d, 2H, J=8.5 Hz), 6.65(d, 1H, J=8.5 Hz), 6.1(dd, 1H, J=8.5 Hz, J=2.8 Hz), 6.31-6.26(m, 2H), 5.61(d, 1H, J=9.8 Hz), 4.40(s, 2H), 3.77(s, 3H), 2.74-2.61(m, 2H), 1.99-1.87(m, 2H), 1.40(s, 3H); m/z: 430.24 |
| 1-182 | 4-NO$_2$-Bn | H | H | 2 | 4-MeO-Ph | $^1$H NMR(200 MHz, CDCl$_3$) δ 8.19(d, 2H, J=9.0 Hz), 7.53(d, 2H, J=9.0 Hz), 7.07(d, 2H, J=8.5 Hz), 6.80(d, 2H, J=8.5 Hz), 6.65(d, 1H, J=8.5 Hz), 6.39(dd, 1H, J=8.5 Hz, J=2.8 Hz), 6.30-6.24(m, 2H), 5.61(d, 1H, J=9.8 Hz), 4.41(s, 2H), 3.77(s, 3H), 2.74-2.05(m, 2H), 1.99-1.87(m, 2H), 1.40(s, 3H); m/z: 430.71 |
| 1-183 | 2-CF$_3$-Bn | H | H | 2 | 4-MeO-Ph | m/z: 453.95 |
| 1-184 | 3-CF$_3$-Bn | H | H | 2 | 4-MeO-Ph | m/z: 453.04 |
| 1-185 | 4-CF$_3$-Bn | H | H | 2 | 4-MeO-Ph | $^1$H NMR(200 MHz, CDCl$_3$) δ 7.59(d, 2H, J=8.3 Hz), 7.48(d, 2H, J=8.3 Hz), 7.07(d, 2H, J=8.5 Hz), 6.79(d, 2H, J=8.5 Hz), 6.65(d, 1H, J=8.5 Hz), 6.42(dd, 1H, J=8.5 Hz, J=2.8 Hz), 6.30-6.26(m, 2H), 5.60(d, 1H, J=9.8 Hz), 4.35(s, 2H), 3.77(s, 3H), 2.74-2.61(m, 2H), 1.98-1.86(m, 2H), 1.39(s, 3H); m/z: 453.24 |
| 1-186 | 4-EtO-Bn | H | H | 2 | 4-MeO-Ph | m/z: 429.74 |
| 1-187 | 2,5-Di-Me-Bn | H | H | 2 | 4-MeO-Ph | m/z: 413.04 |
| 1-188 | 2,6-Di-Me-Bn | H | H | 2 | 4-MeO-Ph | m/z: 413.46 |
| 1-189 | 4-Br—2-F-Bn | H | H | 2 | 4-MeO-Ph | m/z: 482.44 |
| 1-190 | (pyridin-2-ylmethyl, gem-dimethyl) | H | H | 2 | 4-MeO-Ph | $^1$H NMR(200 MHz, CDCl$_3$) δ 8.58(m, 1H), 7.65(m, 1H), 7.34(d, 1H, J=6.7 Hz), 7.21-7.14(m, 1H), 7.07(d, 2H, J=8.5 Hz), 6.79(d, 2H, J=8.5 Hz), 6.66(d, 1H, J=8.5 Hz), 6.48(dd, 1H, J=8.5 Hz, J=2.8 Hz), 6.35(d, 1H, J=2.8 Hz), 6.30(d, 1H, J=9.8 Hz), 5.59(d, 1H, J=9.8 Hz), 4.41(s, 2H), 3.77(s, 3H), 2.74-2.61(m, 2H), 1.98-1.86(m, 2H), 1.39(s, 3H); m/z: 386.85 |

TABLE 1-continued

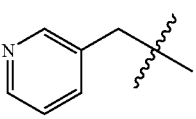
(1)

| Compound No. | R¹ | R² | R³ | n | R⁴ | NMR & Mass analytic results |
|---|---|---|---|---|---|---|
| 1-191 | 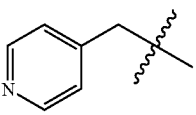 | H | H | 2 | 4-MeO-Ph | m/z: 386.50 |
| 1-192 | 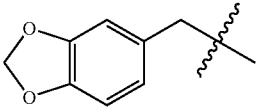 | H | H | 2 | 4-MeO-Ph | m/z: 386.25 |
| 1-193 | 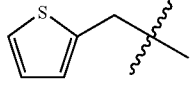 | H | H | 2 | 4-MeO-Ph | m/z: 429.34 |
| 1-194 | 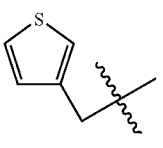 | H | H | 2 | 4-MeO-Ph | $^1$H NMR(200 MHz, CDCl$_3$) δ 7.24-7.22(m, 1H), 7.21-7.07(m, 2H), 7.06-6.94(m, 2H), 6.80(d, 2H, J=8.5 Hz), 6.68(d, 1H, J=8.5 Hz), 6.50(dd, 1H, J=8.5 Hz, J=2.8 Hz), 6.38(d, 1H, J=2.8 Hz), 6.31(d, 1H, J=10.2 Hz), 5.60(d, 1H, J=10.2 Hz), 4.46(s, 2H), 3.78(s, 3H), 2.76-2.61(m, 2H), 2.02-1.87(m, 2H), 1.41(s, 3H); m/z: 391.47 |
| 1-195 | 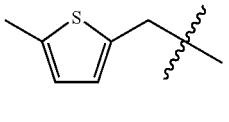 | H | H | 2 | 4-MeO-Ph | $^1$H NMR(200 MHz, CDCl$_3$) δ 7.33-7.26(m, 1H), 7.21-7.18(m, 1H), 7.11-7.07(m, 3H), 6.81(d, 2H, J=8.5 Hz), 6.68(d, 1H, J=8.5 Hz), 6.48(dd, 1H, J=8.5 Hz, J=2.8 Hz), 6.36-6.29(m, 2H), 5.61(d, 1H, J=10.2 Hz), 4.28(s, 2H), 3.78(s, 3H), 2.76-2.61(m, 2H), 1.99-1.40(m, 2H), 1.41(s, 3H); m/z: 391.95 |
| 1-196 | 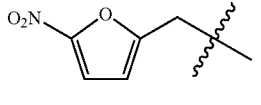 | H | H | 2 | 4-MeO-Ph | $^1$H NMR(200 MHz, CDCl$_3$) δ 7.09(d, 2H, J=8.5 Hz), 6.83-6.77(m, 4H), 6.68(d, 1H, J=8.6 Hz), 6.61-6.59(m, 1H), 6.49(dd, 1H, J=8.6 Hz, J=2.8 Hz), 6.37-6.29(m, 2H), 5.60(d, 1H, J=9.7 Hz), 4.36(s, 2H), 3.78(s, 3H), 2.76-2.65(m, 2H), 2.45(s, 3H), 2.00-1.88(m, 2H), 1.41(s, 3H); m/z: 405.47 |
| 1-197 | 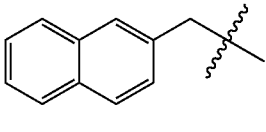 | H | H | 2 | 4-MeO-Ph | m/z: 420.74 |
| 1-198 | 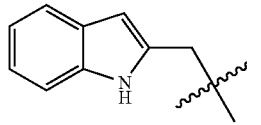 | H | H | 2 | 4-MeO-Ph | $^1$H NMR(200 MHz, CDCl$_3$) δ 7.85-7.79(m, 4H), 7.52-7.27(m, 3H), 7.08(d, 2H, J=8.5 Hz), 6.80(d, 2H, J=8.5 Hz), 6.67(d, 1H, J=8.5 Hz), 6.50(dd, 1H, J=8.5 Hz, J=2.7 Hz), 6.38(d, 1H, J=2.7 Hz), 6.30(d, 1H, J=9.8 Hz), 5.60(d, 1H, J=9.8 Hz), 4.44(s, 2H), 3.77(s, 3H), 2.75-2.61(m, 2H), 1.999-1.87(m, 2H), 1.40(s, 3H); m/z: 435.95 |
| 1-199 |  | Me | H | 2 | 4-MeO-Ph | m/z: 424.57 |

TABLE 1-continued (1)

[Structure: chromene with R¹-NH at 6-position, R² at 7, R³ at 8, CH₃ and (CH₂)ₙR⁴ at 2-position]

| Compound No. | R¹ | R² | R³ | n | R⁴ | NMR & Mass analytic results |
|---|---|---|---|---|---|---|
| 1-200 | PhEt | Me | H | 2 | 4-MeO-Ph | ¹H NMR(200 MHz, CDCl₃) δ 7.37-7.13(m, 5H), 7.08(d, 2H, J=8.5 Hz), 6.80(d, 2H, J=8.5 Hz), 6.66(d, 1H, J=8.5 Hz), 6.44(dd, 1H, J=8.5 Hz, J=2.8 Hz), 6.34-6.29(m, 2H), 5.60(d, 1H, J=9.8 Hz), 3.77(s, 3H), 3.36(t, 2H, J=6.9 Hz), 2.91(t, 2H, J=6.9 Hz), 2.75-2.61(m, 2H), 1.99-1.87(m, 2H), 1.40(s, 3H); m/z: 399.74 |
| 1-201 | Bn | Me | H | 0 | Me | ¹H NMR(200 MHz, CDCl₃) δ 7.41-7.32(m, 5H), 6.61(s, 1H), 6.32(s, 1H), 6.26(d, 1H, J=9.8 Hz), 5.55(d, 1H, J=9.8 Hz), 4.32(s, 2H), 2.13(s, 3H), 1.41(s, 6H); m/z: 279.65 |
| 1-202 | 2-MeO-Bn | Me | H | 0 | Me | m/z: 309.77 |
| 1-203 | 3-MeO-Bn | Me | H | 0 | Me | m/z: 309.05 |
| 1-204 | 4-MeO-Bn | Me | H | 0 | Me | ¹H NMR(200 MHz, CDCl₃) δ 7.32(d, 2H, J=8.8 Hz), 6.90(d, 2H, J=8.8 Hz), 6.59(s, 1H), 6.32(s, 1H), 6.26(d, 1H, J=9.7 Hz), 5.54(d, 1H, J=9.7 Hz), 4.23(s, 2H), 3.82(s, 3H), 2.11(s, 3H), 1.40(s, 6H); m/z: 309.35 |
| 1-205 | 2-t-Bu-Bn | Me | H | 0 | Me | m/z: 335.88 |
| 1-206 | 3-t-Bu-Bn | Me | H | 0 | Me | m/z: 335.95 |
| 1-207 | 4-t-Bu-Bn | Me | H | 0 | Me | ¹H NMR(200 MHz, CDCl₃) δ 7.43-7.27(m, 4H), 6.61(s, 1H), 6.37(s, 1H), 6.29(d, 1H, J=9.8 Hz), 5.56(d, 1H, J=9.8 Hz), 4.28(s, 2H), 2.13(s, 3H), 1.41(s, 6H), 1.35(s, 9H) m/z: 335.01 |
| 1-208 | 2-Me-Bn | Me | H | 0 | Me | ¹H NMR(200 MHz, CDCl₃) δ 7.37-7.33(m, 1H), 7.25-7.18(m, 3H), 6.61(s, 1H), 6.34(s, 1H), 6.29(d, 1H, J=9.8 Hz), 5.56(d, 1H, J=9.8 Hz), 4.26(s, 2H), 2.40(s, 3H), 2.11(s, 3H), 1.42(s, 6H); m/z: 293.74 |
| 1-209 | 3-Me-Bn | Me | H | 0 | Me | m/z: 293.25 |
| 1-210 | 4-Me-Bn | Me | H | 0 | Me | ¹H NMR(200 MHz, CDCl₃) δ 7.30(d, 2H, J=7.9 Hz), 7.18(d, 2H, J=7.9 Hz), 6.60(s, 1H), 6.34(s, 1H), 6.27(d, 1H, J=9.7 Hz), 5.55(d, 1H, J=9.7 Hz), 4.27(s, 2H), 2.37(s, 3H), 2.12(s, 3H), 1.41(s, 6H); m/z: 293.65 |
| 1-211 | 2-F-Bn | Me | H | 0 | Me | ¹H NMR(200 MHz, CDCl₃) δ 7.38(m, 1H), 7.13-7.01(m, 3H), 6.58(s, 1H), 6.32(s, 1H), 6.23(d, 1H, J=9.8 Hz), 5.53(d, 1H, J=9.8 Hz), 4.38(s, 2H), 2.13(s, 3H), 1.39(s, 6H); m/z: 297.17 |
| 1-212 | 3-F-Bn | Me | H | 0 | Me | ¹H NMR(200 MHz, CDCl₃) δ 7.37-7.29(m, 1H), 7.19-7.09(m, 2H), 7.02-6.94(m, 1H), 6.61(s, 1H), 6.24(s, 1H), 6.23(d, 1H, J=9.7 Hz), 5.54(d, 1H, J=9.7 Hz), 4.33(s, 2), 2.15(s, 3H), 1.40(s, 6H); m/z: 297.31 |
| 1-213 | 4-F-Bn | Me | H | 0 | Me | ¹H NMR(200 MHz, CDCl₃) δ 7.40-7.32(m, 2H), 7.09-7.00(m, 2H), 6.60(s, 1H), 6.28(s, 1H), 6.24(d, 1H, J=9.6 Hz), 5.55(d, 1H, J=9.6 Hz), 4.28(s, 2H), 2.13(s, 3H), 1.40(s, 6H); m/z: 297.37 |
| 1-214 | 2-Cl-Bn | Me | H | 0 | Me | ¹H NMR(200 MHz, CDCl₃) δ 7.42-7.37(m, 2H), 7.2-7.20(m, 2H), 6.60(s, 1H), 6.23(m, 2H), 5.53(d, 1H, J=9.8 Hz), 4.43(s, 3H), 2.16(s, 3H), 1.40(s, 6H); m/z: 313.78 |
| 1-215 | 3-Cl-Bn | Me | H | 0 | Me | ¹H NMR(200 MHz, CDCl₃) δ 7.40(s, 1H), 7.28(m, 3H), 6.61(s, 1H), 6.26-6.21(m, 2H), 5.59-5.52(m, 1H), 4.31(s, 2H), 2.15(s, 3H), 1.41(s, 6H); m/z: 313.28 |
| 1-216 | 4-Cl-Bn | Me | H | 0 | Me | m/z: 313.52 |
| 1-217 | 2-CN-Bn | Me | H | 0 | Me | m/z: 304.47 |
| 1-218 | 3-CN-Bn | Me | H | 0 | Me | m/z: 304.47 |
| 1-219 | 4-CN-Bn | Me | H | 0 | Me | ¹H NMR(200 MHz, CDCl₃) δ 7.63(d, 2H, J=8.4 Hz), 7.48(d, 2H, J=8.4 Hz), 6.60(s, 1H), 6.16(d, 1H, J=9.8 Hz), 6.12(s, 1H), 5.52(d, 1H, J=9.8 Hz), 4.41(s, 2H), 2.15(s, 3H), 1.38(s, 6H); m/z: 304.74 |
| 1-220 | 2-NO₂-Bn | Me | H | 0 | Me | m/z: 324.58 |
| 1-221 | 3-NO₂-Bn | Me | H | 0 | Me | m/z: 324.24 |
| 1-222 | 4-NO₂-Bn | Me | H | 0 | Me | ¹H NMR(200 MHz, CDCl₃) δ 8.19(d, 2H, J=8.8 Hz), 7.54(d, 2H, J=8.8 Hz), 6.60(s, 1H), 6.18(s, 1H), 6.12(d, 1H, J=9.8 Hz), 5.52(d, 1H, J=9.8 Hz), 4.45(s, 2H), 2.17(s, 3H), 1.38(s, 6H); m/z: 324.77 |

TABLE 1-continued (1)

| Compound No. | R¹ | R² | R³ | n | R⁴ | NMR & Mass analytic results |
|---|---|---|---|---|---|---|
| 1-223 | 2-CF₃-Bn | Me | H | 0 | Me | m/z: 347.75 |
| 1-224 | 3-CF₃-Bn | Me | H | 0 | Me | m/z: 347.85 |
| 1-225 | 4-CF₃-Bn | Me | H | 0 | Me | ¹H NMR(200 MHz, CDCl₃) δ 7.60(d, 2H, J=8.2H), 7.50(d, 2H, J=8.2 Hz), 6.61(s, 1H), 6.21(m, 2H), 5.53(d, 1H, J=9.6 Hz), 4.40(s, 2H), 2.15(s, 3H), 1.39(s, 6H); m/z: 347.59 |
| 1-226 | 4-EtO-Bn | Me | H | 0 | Me | ¹H NMR(200 MHz, CDCl₃) δ 7.32-7.26(m, 2H), 6.88(d, 2H, J=8.7 Hz), 6.58(s, 1H), 6.33(s, 1H), 6.26(d, 1H, J=9.7 Hz), 5.53(d, 1H, J=9.7 Hz), 4.22(s, 2H), 4.05(q, 2H, J=7.0 Hz), 2.10(s, 3H), 1.45-1.26(m, 9H); m/z: 323.35 |
| 1-227 | 2,5-Di-Me-Bn | Me | H | 0 | Me | m/z: 307.74 |
| 1-228 | 2,6-Di-Me-Bn | Me | H | 0 | Me | m/z: 307.74 |
| 1-229 | 4-Br—2-F-Bn | Me | H | 0 | Me | m/z: 376.57 |
| 1-230 | (pyridin-2-ylmethyl) | Me | H | 0 | Me | m/z: 376.74 |
| 1-231 | (pyridin-3-ylmethyl) | Me | H | 0 | Me | m/z: 376.14 |
| 1-232 | (pyridin-4-ylmethyl) | Me | H | 0 | Me | m/z: 376.05 |
| 1-233 | (benzo[d][1,3]dioxol-5-ylmethyl) | Me | H | 0 | Me | m/z: 323.19 |
| 1-234 | (thiophen-2-ylmethyl) | Me | H | 0 | Me | ¹H NMR(200 MHz, CDCl₃) δ 7.48-7.41(m, 1H), 7.26-7.21(m, 1H), 7.04-6.96(m, 1H), 6.68(s, 1H), 6.37(s, 1H), 6.26(d, 1H, J=9.6 Hz), 5.55(d, 1H, J=9.6 Hz), 4.49(s, 2H), 2.12(s, 3H), 1.40(s, 6H); m/z: 285.54 |
| 1-235 | (thiophen-3-ylmethyl) | Me | H | 0 | Me | ¹H NMR(200 MHz, CDCl₃) δ 7.33(dd, 1H, J=4.8 Hz, J=3.0 Hz), 7.23(dd, 1H, J=3.0 Hz, J=1.0 Hz), 7.12(dd, 1H, J=4.8 Hz, J=1.0 Hz), 6.62(s, 1H), 6.36(s, 1H), 6.29(d, 1H, J=9.8 Hz), 5.56(d, 1H, J=9.8 Hz), 4.33(s, 2H), 2.13(s, 3H), 1.42(s, 6H); m/z: 285.74 |
| 1-236 | (5-methylthiophen-2-ylmethyl) | Me | H | 0 | Me | ¹H NMR(200 MHz, CDCl₃) 6.80-6.66(m, 1H), 6.64-6.58(m, 2H), 6.37(s, 1H), 6.27(d, 1H, J=9.7 Hz), 5.55(d, 1H, J=9.8 Hz), 4.40(s, 2H), 2.46(s, 3H), 2.10(s, 3H), 1.39(s, 6H); m/z: 299.47 |
| 1-237 | (5-nitrofuran-2-ylmethyl) | Me | H | 0 | Me | m/z: 314.95 |
| 1-238 | (naphthalen-2-ylmethyl) | Me | H | 0 | Me | ¹H NMR(200 MHz, CDCl₃) δ 7.88-7.82(m, 4H), 7.56-7.47(m, 3H), 6.63(s, 1H), 6.36(s, 1H), 6.24(d, 1H, J=9.8 Hz), 5.53(d, 1H, J=9.8 Hz), 4.49(s, 2H), 2.16(s, 3H), 1.41(s, 6H); m/z: 329.74 |

TABLE 1-continued

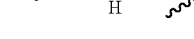

| Compound No. | $R^1$ | $R^2$ | $R^3$ | n | $R^4$ | NMR & Mass analytic results |
|---|---|---|---|---|---|---|
| 1-239 | 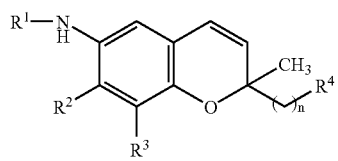 | Me | H | 0 | Me | m/z: 318.54 |
| 1-240 | PhEt | Me | H | 0 | Me | m/z: 293.74 |
| 1-241 | Bn | Me | H | 1 | Me | m/z: 293.85 |
| 1-242 | 2-MeO-Bn | Me | H | 1 | Me | m/z: 323.52 |
| 1-243 | 3-MeO-Bn | Me | H | 1 | Me | m/z: 323.38 |
| 1-244 | 4-MeO-Bn | Me | H | 1 | Me | $^1$H NMR(200 MHz, CDCl$_3$) δ 7.34(d, 2H, J=8.8 Hz), 6.92(d, 2H, J=8.8 Hz), 6.62(s, 1H), 6.34(s, 1H), 6.32(d, 1H, J=9.8 Hz), 5.52(d, 1H, J=9.8 Hz), 4.25(s, 2H), 3.83(s, 3H), 2.12(s, 3H), 1.71(q, 2H, J=7.4 Hz), 1.36(s, 3H), 0.98(t, 3H, J=7.4 Hz); m/z: 323.47 |
| 1-245 | 2-t-Bu-Bn | Me | H | 1 | Me | m/z: 349.48 |
| 1-246 | 3-t-Bu-Bn | Me | H | 1 | Me | m/z: 349.85 |
| 1-247 | 4-t-Bu-Bn | Me | H | 1 | Me | $^1$H NMR(200 MHz, CDCl$_3$) δ 7.41(d, 2H, J=8.6 Hz), 7.34(d, 2H, J=8.6 Hz), 6.60(s, 1H), 6.35(s, 1H), 6.33(d, 1H, J=9.8 Hz), 5.51(d, 1H, J=9.8 Hz), 4.28(s, 2H), 2.12(s, 3H), 1.70(q, 2H, J=7.6 Hz), 1.35(s, 12H), 0.97(t, 3H, J=7.6 Hz); m/z: 349.57 |
| 1-248 | 2-Me-Bn | Me | H | 1 | Me | $^1$H NMR(200 MHz, CDCl$_3$) δ 7.35(m, 1H), 7.25-7.20(m, 3H), 6.61(s, 1H), 6.33(m, 2H), 5.52(d, 1H, J=9.8 Hz), 4.26(s, 2H), 2.40(s, 3H), 2.11(s, 3H), 1.71(q, 2H, J=7.6 Hz), 1.36(s, 3H), 0.97(t, 3H, J=7.6 Hz); m/z: 307.65 |
| 1-249 | 3-Me-Bn | Me | H | 1 | Me | m/z: 307.44 |
| 1-250 | 4-Me-Bn | Me | H | 1 | Me | $^1$H NMR(200 MHz, CDCl$_3$) δ 7.30(d, 2H, J=7.8 Hz), 7.17(d, 2H, J=7.8 Hz), 6.59(s, 1H), 6.32(s, 1H), 6.30(d, 1H, J=9.8 Hz), 5.50(d, 1H, J=9.8 Hz), 4.27(s, 2H), 2.37(s, 3H), 2.12(s, 3H), 1.70(q, 2H, J=7.4 Hz), 1.35(s, 3H), 0.96(t, 3H, J=7.4 Hz); m/z: 307.58 |
| 1-251 | 2-F-Bn | Me | H | 1 | Me | m/z: 311.57 |
| 1-252 | 3-F-Bn | Me | H | 1 | Me | $^1$H NMR(200 MHz, CDCl$_3$) δ 7.32(m, 1H), 7.15(m, 2H), 6.68(m, 1H), 6.61(s, 1H), 6.27(d, 1H, J=10.0 Hz), 6.23(s, 1H), 5.50(d, 1H, J=10.0 Hz), 4.33(s, 2H), 2.15(s, 3H), 1.70(q, 2H, J=7.6 Hz), 1.35(s, 3H), 0.96(t, 3H, J=7.6 Hz); m/z: 311.17 |
| 1-253 | 4-F-Bn | Me | H | 1 | Me | $^1$H NMR(200 MHz, CDCl$_3$) δ 7.40-7.33(m, 2H), 7.09-7.00(m, 2H), 6.60(s, 1H), 6.28(d, 1H, J=9.9 Hz), 6.27(s, 1H), 5.50(d, 1H, J=9.9 Hz), 4.28(s, 2H), 2.13(s, 3H), 1.70(q, 2H, J=7.5 Hz), 1.35(s, 3H), 0.96(t, 3H, 17.5 Hz); m/z: 311.47 |
| 1-254 | 2-Cl-Bn | Me | H | 1 | Me | $^1$H NMR(200 MHz, CDCl$_3$) δ 7.44-7.37(m, 2H), 7.25-7.20(m, 2H), 6.59(s, 1H), 6.27(d, 1H, J=9.8 Hz), 6.22(s, 1H), 5.49(d, 1H, J=9.8 Hz), 4.42(s, 2H), 2.16(s, 3H), 1.69(q, 2H, J=7.5 Hz), 1.34(s, 3H), 0.95(t, 3H, J=7.5 Hz); m/z: 327.52 |
| 1-255 | 3-Cl-Bn | Me | H | 1 | Me | $^1$H NMR(200 MHz, CDCl$_3$) δ 7.40(s, 1H), 7.28(m, 3H), 6.60(s, 1H), 6.27(d, 1H, J=9.8 Hz), 6.22(s, 1H), 5.50(d, 1H, J=9.8 Hz), 4.30(s, 2H), 2.15(s, 3H), 1.69(q, 2H, J=7.4 Hz), 1.34(s, 3H), 0.96(t, 3H, J=7.4 Hz); m/z: 327.74 |
| 1-256 | 4-Cl-Bn | Me | H | 1 | Me | m/z: 327.67 |
| 1-257 | 2-CN-Bn | Me | H |  | Me | m/z: 318.48 |
| 1-258 | 3-CN-Bn | Me | H | 1 | Me | m/z: 318.95 |
| 1-259 | 4-CN-Bn | Me | H | 1 | Me | $^1$H NMR(200 MHz, CDCl$_3$) δ 7.62(d, 2H, J=8.2 Hz), 7.48(d, 2H, J=8.2 Hz), 6.59(s, 1H), 6.20(d, 1H, J=9.8 Hz), 6.09(s, 1H), 5.47(d, 1H, J=9.8 Hz), 4.40(s, 2H), 3.32(brs, 1H), 2.15(s, 3H), 1.67(q, 2H, J=7.6 Hz), 1.32(s, 3H), 0.93(t, 3H, J=7.6 Hz); m/z: 318.74 |
| 1-260 | 2-NO$_2$-Bn | Me | H | 1 | Me | m/z: 338.64 |
| 1-261 | 3-NO$_2$-Bn | Me | H | 1 | Me | m/z: 338.85 |
| 1-262 | 4-NO$_2$-Bn | Me | H | 1 | Me | m/z: 338.95 |
| 1-263 | 2-CF$_3$-Bn | Me | H | 1 | Me | m/z: 361.74 |
| 1-264 | 3-CF$_3$-Bn | Me | H | 1 | Me | m/z: 361.58 |

TABLE 1-continued (1)

| Compound No. | R¹ | R² | R³ | n | R⁴ | NMR & Mass analytic results |
|---|---|---|---|---|---|---|
| 1-265 | 4-CF₃-Bn | Me | H | 1 | Me | ¹H NMR(200 MHz, CDCl₃) δ 7.62(d, 2H, J=8.4 Hz), 7.51(d, 2H, J=8.4 Hz), 6.61(s, 1H), 6.25(d, 1H, J=9.8 Hz), 6.20(s, 1H), 5.50(d, 1H, J=9.8 Hz), 4.40(s, 2H), 2.16(s, 3H), 1.70(q, 2H, J=7.4 Hz), 1.34(s, 3H), 0.96(t, 3H, J=7.4 Hz); m/z: 361.95 |
| 1-266 | 4-EtO-Bn | Me | H | 1 | Me | ¹H NMR(200 MHz, CDCl₃) δ 7.32-7.26(m, 2H), 6.87(d, 2H, J=8.7 Hz), 6.85(s, 1H), 6.57(s, 1H), 6.28(d, 1H, J=9.9 Hz), 5.49(d, 1H, J=9.9 Hz), 4.22(s, 2H), 4.03(t, 2H, J=6.9 Hz), 2.09(s, 3H), 1.70-1.66(m, 2H), 1.45-1.23(m, 5H), 0.94(m, 3H); m/z: 337.74 |
| 1-267 | 2,5-Di-Me-Bn | Me | H | 1 | Me | m/z: 321.58 |
| 1-268 | 2,6-Di-Me-Bn | Me | H | 1 | Me | m/z: 321.54 |
| 1-269 | 4-Br—2-F-Bn | Me | H | 1 | Me | ¹H NMR(200 MHz, CDCl₃) δ 7.28-7.24(m, 3H), 6.58(s, 1H), 6.25(d, 1H, J=9.9 Hz), 6.20(s, 1H), 5.49(d, 1H, J=9.9 Hz), 4.34(s, 2H), 2.13(s, 2H), 1.68(q, 2H, J=7.5 Hz), 1.33(s, 3H), 0.96(t, 3H, J=7.5 Hz); m/z: 390.57 |
| 1-270 | 2-pyridylmethyl | Me | H | 1 | Me | m/z: 294.74 |
| 1-271 | 3-pyridylmethyl | Me | H | 1 | Me | m/z: 294.41 |
| 1-272 | 4-pyridylmethyl | Me | H | 1 | Me | m/z: 294.47 |
| 1-273 | 1,3-benzodioxol-5-ylmethyl | Me | H | 1 | Me | m/z: 337.34 |
| 1-274 | 2-thienylmethyl | Me | H | 1 | Me | m/z: 299.85 |
| 1-275 | 3-thienylmethyl | Me | H | 1 | Me | ¹H NMR(200 MHz, CDCl₃) δ 7.33(dd, 1H, J=4.8 Hz, J=3.2 Hz), 7.23(dd, 1H, J=3.2 Hz, J=1.2 Hz), 7.14(dd, 1H, J=4.8 Hz, J=1.2 Hz), 6.62(s, 1H), 6.35(s, 1H), 6.33(d, 1H, J=9.8 Hz), 5.53(d, 1H, J=9.8 Hz), 4.33(s, 2H), 2.13(s, 3H), 1.71(q, 2H, J=7.6 Hz), 1.37(s, 3H), 0.98(t, 3H, J=7.6 Hz); m/z: 299.77 |
| 1-276 | 5-methyl-2-thienylmethyl | Me | H | 1 | Me | m/z: 313.65 |
| 1-277 | 5-nitro-2-furylmethyl | Me | H | 1 | Me | m/z: 328.95 |

TABLE 1-continued (1)

[Structure: R¹-NH- attached to a 2H-chromene with CH₃ and (CH₂)ₙR⁴ at position 2, R² and R³ on the benzene ring]

| Compound No. | R¹ | R² | R³ | n | R⁴ | NMR & Mass analytic results |
|---|---|---|---|---|---|---|
| 1-278 | [penta-dienyl/polyene chain] | Me | H | 1 | Me | ¹H NMR(200 MHz, CDCl₃) δ 7.88-7.82(m, 4H), 7.56-7.46(m, 3H), 6.62(s, 1H), 6.35(s, 1H), 6.28(d, 1H, J=9.8 Hz), 5.49(d, 1H, J=9.8 Hz), 4.48(s, 2H), 2.16(s, 3H), 1.70(q, 2H, J=7.6 Hz), 1.35(s, 3H), 0.96(t, 3H, J=7.6 Hz); m/z: 343.44 |
| 1-279 | [1H-indol-2-ylmethyl] | Me | H | 1 | Me | m/z: 332.48 |
| 1-280 | PhEt | Me | H | 1 | Me | m/z: 307.05 |
| 1-281 | Bn | Me | H | 2 | Me | m/z: 307.65 |
| 1-282 | 2-MeO-Bn | Me | H | 2 | Me | m/z: 337.84 |
| 1-283 | 3-MeO-Bn | Me | H | 2 | Me | m/z: 337.14 |
| 1-284 | 4-MeO-Bn | Me | H | 2 | Me | m/z: 337.84 |
| 1-285 | 2-t-Bu-Bn | Me | H | 2 | Me | m/z: 363.74 |
| 1-286 | 3-t-Bu-Bn | Me | H | 2 | Me | m/z: 363.28 |
| 1-287 | 4-t-Bu-Bn | Me | H | 2 | Me | m/z: 363.55 |
| 1-288 | 2-Me-Bn | Me | H | 2 | Me | m/z: 321.42 |
| 1-289 | 3-Me-Bn | Me | H | 2 | Me | m/z: 321.74 |
| 1-290 | 4-Me-Bn | Me | H | 2 | Me | m/z: 321.41 |
| 1-291 | 2-F-Bn | Me | H | 2 | Me | ¹H NMR(200 MHz, CDCl₃) δ 7.50-7.30(m, 1H), 7.30-7.20(m, 1H), 7.20-7.00(m, 2H), 6.58(s, 1H), 6.58-6.25(m, 2H), 5.49(d, 1H, J=9.8 Hz), 2.13(s, 3H), 1.73-1.62(m, 2H), 1.39-1.22(m, 5H), 1.01-0.91(m, 3H); m/z: 325.78 |
| 1-292 | 3-F-Bn | Me | H | 2 | Me | m/z: 325.14 |
| 1-293 | 4-F-Bn | Me | H | 2 | Me | m/z: 325.13 |
| 1-294 | 2-Cl-Bn | Me | H | 2 | Me | m/z: 341.80 |
| 1-295 | 3-Cl-Bn | Me | H | 2 | Me | m/z: 341.20 |
| 1-296 | 4-Cl-Bn | Me | H | 2 | Me | m/z: 341.41 |
| 1-297 | 2-CN-Bn | Me | H | 2 | Me | m/z: 332.47 |
| 1-298 | 3-CN-Bn | Me | H | 2 | Me | m/z: 332.84 |
| 1-299 | 4-CN-Bn | Me | H | 2 | Me | m/z: 332.44 |
| 1-300 | 2-NO₂-Bn | Me | H | 2 | Me | m/z: 352.47 |
| 1-301 | 3-NO₂-Bn | Me | H | 2 | Me | m/z: 352.44 |
| 1-302 | 4-NO₂-Bn | Me | H | 2 | Me | m/z: 352.15 |
| 1-303 | 2-CF₃-Bn | Me | H | 2 | Me | m/z: 375.65 |
| 1-304 | 3-CF₃-Bn | Me | H | 2 | Me | m/z: 375.25 |
| 1-305 | 4-CF₃-Bn | Me | H | 2 | Me | m/z: 375.58 |
| 1-306 | 4-EtO-Bn | Me | H | 2 | Me | m/z: 351.25 |
| 1-307 | 2,5-Di-Me-Bn | Me | H | 2 | Me | m/z: 335.58 |
| 1-308 | 2,6-Di-Me-Bn | Me | H | 2 | Me | m/z: 335.77 |
| 1-309 | 4-Br—2-F-Bn | Me | H | 2 | Me | m/z: 404.47 |
| 1-310 | [pyridin-2-ylmethyl] | Me | H | 2 | Me | m/z: 308.44 |
| 1-311 | [pyridin-3-ylmethyl] | Me | H | 2 | Me | m/z: 308.44 |
| 1-312 | [pyridin-4-ylmethyl] | Me | H | 2 | Me | m/z: 308.47 |

TABLE 1-continued (1)

[Structure: chromene core with R¹-NH at 6-position, CH₃ and (CH₂)ₙR⁴ at 2-position, R² at 7-position, R³ at 8-position]

| Compound No. | R¹ | R² | R³ | n | R⁴ | NMR & Mass analytic results |
|---|---|---|---|---|---|---|
| 1-313 | benzo[1,3]dioxol-5-ylmethyl | Me | H | 2 | Me | m/z: 351.10 |
| 1-314 | thiophen-2-ylmethyl | Me | H | 2 | Me | m/z: 313.78 |
| 1-315 | thiophen-3-ylmethyl | Me | H | 2 | Me | $^1$H NMR(200 MHz, CDCl$_3$) δ 7.36-7.32(m, 1H), 7.27-7.23(m, 1H), 7.16-7.12(m, 1H), 6.61(s, 1H), 6.36(s, 1H), 6.32(d, 1H, J=9.7 Hz), 5.53(d, 1H, J=9.7 Hz), 4.34(s, 2H), 3.36(br, 1H), 2.14(s, 3H), 1.74-1.66(m, 2H), 1.64-1.41(m, 2H), 1.38(s, 3H), 0.95(m, 3H); m/z: 313.14 |
| 1-316 | (5-methylthiophen-2-yl)methyl | Me | H | 2 | Me | m/z: 327.44 |
| 1-317 | (5-nitrofuran-2-yl)methyl | Me | H | 2 | Me | m/z: 342.45 |
| 1-318 | naphthalen-2-ylmethyl | Me | H | 2 | Me | m/z: 357.51 |
| 1-319 | (1H-indol-2-yl)methyl | Me | H | 2 | Me | m/z: 346.47 |
| 1-320 | PhEt | Me | H | 2 | Me | m/z: 321.47 |
| 1-321 | Bn | Me | H | 2 | Ph | m/z: 369.78 |
| 1-322 | 2-MeO-Bn | Me | H | 2 | Ph | m/z: 399.51 |
| 1-323 | 3-MeO-Bn | Me | H | 2 | Ph | m/z: 399.17 |
| 1-324 | 4-MeO-Bn | Me | H | 2 | Ph | m/z: 399.65 |
| 1-325 | 2-t-Bu-Bn | Me | H | 2 | Ph | m/z: 425.17 |
| 1-326 | 3-t-Bu-Bn | Me | H | 2 | Ph | m/z: 425.54 |
| 1-327 | 4-t-Bu-Bn | Me | H | 2 | Ph | m/z: 425.84 |
| 1-328 | 2-Me-Bn | Me | H | 2 | Ph | m/z: 383.57 |
| 1-329 | 3-Me-Bn | Me | H | 2 | Ph | m/z: 383.84 |
| 1-330 | 4-Me-Bn | Me | H | 2 | Ph | m/z: 383.58 |
| 1-331 | 2-F-Bn | Me | H | 2 | Ph | m/z: 387.41 |
| 1-332 | 3-F-Bn | Me | H | 2 | Ph | m/z: 387.05 |
| 1-333 | 4-F-Bn | Me | H | 2 | Ph | m/z: 387.15 |
| 1-334 | 2-Cl-Bn | Me | H | 2 | Ph | m/z: 403.71 |
| 1-335 | 3-Cl-Bn | Me | H | 2 | Ph | m/z: 403.91 |
| 1-336 | 4-Cl-Bn | Me | H | 2 | Ph | m/z: 403.41 |
| 1-337 | 2-CN-Bn | Me | H | 2 | Ph | m/z: 394.51 |
| 1-338 | 3-CN-Bn | Me | H | 2 | Ph | m/z: 394.04 |
| 1-339 | 4-CN-Bn | Me | H | 2 | Ph | m/z: 394.14 |
| 1-340 | 2-NO$_2$-Bn | Me | H | 2 | Ph | m/z: 414.51 |
| 1-341 | 3-NO$_2$-Bn | Me | H | 2 | Ph | m/z: 414.50 |
| 1-342 | 4-NO$_2$-Bn | Me | H | 2 | Ph | m/z: 414.15 |
| 1-343 | 2-CF$_3$-Bn | Me | H | 2 | Ph | m/z: 437.52 |
| 1-344 | 3-CF$_3$-Bn | Me | H | 2 | Ph | m/z: 437.22 |

TABLE 1-continued
(1)
| Compound No. | R¹ | R² | R³ | n | R⁴ | NMR & Mass analytic results |
|---|---|---|---|---|---|---|
| 1-345 | 4-CF₃-Bn | Me | H | 2 | Ph | m/z: 437.27 |
| 1-346 | 4-EtO-Bn | Me | H | 2 | Ph | m/z: 413.54 |
| 1-347 | 2,5-Di-Me-Bn | Me | H | 2 | Ph | m/z: 397.04 |
| 1-348 | 2,6-Di-Me-Bn | Me | H | 2 | Ph | m/z: 397.85 |
| 1-349 | 4-Br—2-F-Bn | Me | H | 2 | Ph | m/z: 466.52 |
| 1-350 | 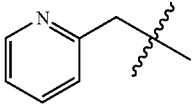 | Me | H | 2 | Ph | m/z: 370.01 |
| 1-351 | 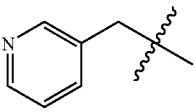 | Me | H | 2 | Ph | m/z: 370.71 |
| 1-352 | 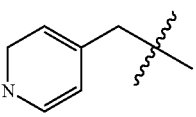 | Me | H | 2 | Ph | m/z: 370.65 |
| 1-353 | 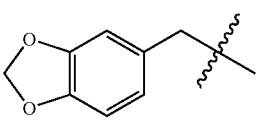 | Me | H | 2 | Ph | m/z: 413.56 |
| 1-354 | 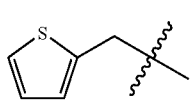 | Me | H | 2 | Ph | m/z: 375.31 |
| 1-355 | 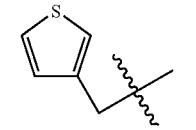 | Me | H | 2 | Ph | m/z: 375.14 |
| 1-356 | 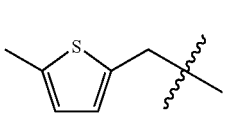 | Me | H | 2 | Ph | ¹H NMR(200 MHz, CDCl₃) δ 7.39-7.16(m, 7H), 6.69(s, 1H), 6.41(d, 1H, J=9.8 Hz), 6.41(s, 1H), 5.61(d, 1H, J=9.8 Hz), 4.37(s, 2H), 3.39(br, 1H), 2.89-2.78(m, 2H), 2.18(s, 6H), 2.14-2.00(m, 2H), 1.48(s, 3H); m/z: 389.41 |
| 1-357 | 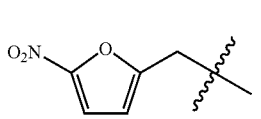 | Me | H | 2 | Ph | m/z: 404.21 |
| 1-358 | 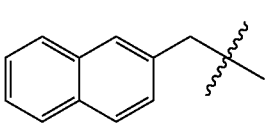 | Me | H | 2 | Ph | m/z: 419.14 |
| 1-359 | 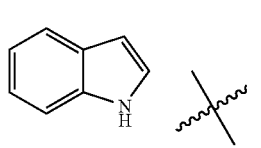 | Me | H | 2 | Ph | m/z: 408.51 |

TABLE 1-continued

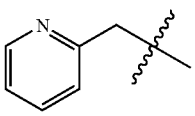

(1)

| Compound No. | R¹ | R² | R³ | n | R⁴ | NMR & Mass analytic results |
|---|---|---|---|---|---|---|
| 1-360 | PhEt | Me | H | 2 | Ph | m/z: 383.47 |
| 1-361 | Bn | Me | Br | 0 | Me | m/z: 358.47 |
| 1-362 | 2-MeO-Bn | Me | Br | 0 | Me | m/z: 388.01 |
| 1-363 | 3-MeO-Bn | Me | Br | 0 | Me | m/z: 388.47 |
| 1-364 | 4-MeO-Bn | Me | Br | 0 | Me | ¹H NMR(200 MHz, CDCl₃) δ 7.30(d, 2H, J=8.6 Hz), 6.89(d, 2H, J=8.6 Hz), 6.30(s, 1H), 6.23(d, 1H, J=8.6 Hz, J=2.8 Hz), 5.59(d, 1H, J=9.8 Hz), 4.22(s, 2H), 3.81(s, 3H), 2.28(s, 3H), 1.44(s, 6H); m/z: 388.71 |
| 1-365 | 2-t-Bu-Bn | Me | Br | 0 | Me | m/z: 414.14 |
| 1-366 | 3-t-Bu-Bn | Me | Br | 0 | Me | m/z: 414.47 |
| 1-367 | 4-t-Bu-Bn | Me | Br | 0 | Me | m/z: 414.47 |
| 1-368 | 2-Me-Bn | Me | Br | 0 | Me | m/z: 372.74 |
| 1-369 | 3-Me-Bn | Me | Br | 0 | Me | m/z: 372.45 |
| 1-370 | 4-Me-Bn | Me | Br | 0 | Me | m/z: 372.58 |
| 1-371 | 2-F-Bn | Me | Br | 0 | Me | m/z: 376.84 |
| 1-372 | 3-F-Bn | Me | Br | 0 | Me | m/z: 376.77 |
| 1-373 | 4-F-Bn | Me | Br | 0 | Me | m/z: 376.44 |
| 1-374 | 2-Cl-Bn | Me | Br | 0 | Me | m/z: 392.74 |
| 1-375 | 3-Cl-Bn | Me | Br | 0 | Me | m/z: 392.44 |
| 1-376 | 4-Cl-Bn | Me | Br | 0 | Me | m/z: 392.55 |
| 1-377 | 2-CN-Bn | Me | Br | 0 | Me | m/z: 383.45 |
| 1-378 | 3-CN-Bn | Me | Br | 0 | Me | m/z: 383.20 |
| 1-379 | 4-CN-Bn | Me | Br | 0 | Me | m/z: 383.44 |
| 1-380 | 2-NO₂-Bn | Me | Br | 0 | Me | m/z: 403.61 |
| 1-381 | 3-NO₂-Bn | Me | Br | 0 | Me | m/z: 403.20 |
| 1-382 | 4-NO₂-Bn | Me | Br | 0 | Me | m/z: 403.74 |
| 1-383 | 2-CF₃-Bn | Me | Br | 0 | Me | m/z: 426.47 |
| 1-384 | 3-CF₃-Bn | Me | Br | 0 | Me | m/z: 426.62 |
| 1-385 | 4-CF₃-Bn | Me | Br | 0 | Me | m/z: 426.20 |
| 1-386 | 4-EtO-Bn | Me | Br | 0 | Me | m/z: 402.35 |
| 1-387 | 2,5-Di-Me-Bn | Me | Br | 0 | Me | m/z: 386.74 |
| 1-388 | 2,6-Di-Me-Bn | Me | Br | 0 | Me | m/z: 386.68 |
| 1-389 | 4-Br—2-F-Bn | Me | Br | 0 | Me | m/z: 455.55 |
| 1-390 | 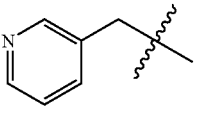 | Me | Br | 0 | Me | m/z: 359.57 |
| 1-391 | 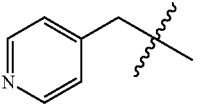 | Me | Br | 0 | Me | m/z: 359.28 |
| 1-392 | 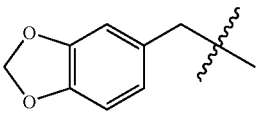 | Me | Br | 0 | Me | m/z: 359.57 |
| 1-393 | 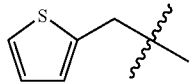 | Me | Br | 0 | Me | m/z: 402.13 |
| 1-394 |  | Me | Br | 0 | Me | m/z: 364.14 |

TABLE 1-continued (1)

R¹—NH— [chromene core with CH₃, R⁴, (CH₂)n, O, R², R³ substituents]

| Compound No. | R¹ | R² | R³ | n | R⁴ | NMR & Mass analytic results |
|---|---|---|---|---|---|---|
| 1-395 | thiophen-3-ylmethyl | Me | Br | 0 | Me | m/z: 364.58 |
| 1-396 | (5-methylthiophen-2-yl)methyl | Me | Br | 0 | Me | m/z: 378.47 |
| 1-397 | (5-nitrofuran-2-yl)methyl | Me | Br | 0 | Me | m/z: 393.17 |
| 1-398 | naphthalen-2-ylmethyl | Me | Br | 0 | Me | m/z: 408.14 |
| 1-399 | (1H-indol-2-yl)methyl | Me | Br | 0 | Me | m/z: 397.25 |
| 1-400 | PhEt | Me | Br | 0 | Me | m/z: 372.65 |
| 1-401 | Bn | H | Ph | 0 | Me | ¹H NMR(200 MHz, CDCl₃) δ 6.8(d, 2H, J=7.55 Hz), 7.53-.26(m, 8H), 6.57(d, 1H, J=2.8 Hz), 6.36(d, 1H, J=2.8 Hz), 6.30(d, 1H, J=9.8 Hz), 5.65(d, 1H, J=9.8 Hz), 4.31(s, 2H), 1.41(s, 6H); m/z: 341.57 |
| 1-402 | 2-MeO-Bn | H | Ph | 0 | Me | m/z: 371.34 |
| 1-403 | 3-MeO-Bn | H | Ph | 0 | Me | m/z: 371.41 |
| 1-404 | 4-MeO-Bn | H | Ph | 0 | Me | ¹H NMR(200 MHz, CDCl₃) δ 7.58-7.53(m, 2H), 7.42-7.26(m, 5H), 6.89(d, 2H, J=8.9 Hz), 6.56(d, 1H, J=2.8 Hz), 6.35(d, 1H, J=2.8 Hz), 6.30(d, 1H, J=9.8 Hz), 5.65(d, 1H, J=9.8 Hz), 4.23(s, 2H), 3.81(s, 3H), 1.40(s, 6H); m/z: 371.17 |
| 1-405 | 2-t-Bu-Bn | H | Ph | 0 | Me | m/z: 397.57 |
| 1-406 | 3-t-Bu-Bn | H | Ph | 0 | Me | m/z: 397.51 |
| 1-407 | 4-t-Bu-Bn | H | Ph | 0 | Me | ¹H NMR(200 MHz, CDCl₃) δ 7.58-7.53(m, 2H), 7.43-7.29(m, 7H), 6.57(d, 1H, J=2.8 Hz), 6.38(d, 2H, J=2.8 Hz), 6.31(d, 1H, J=9.8 Hz), 5.65(d, 1H, J=9.8 Hz), 4.27(s, 2H), 1.41(s, 6H), 1.34(s, 9H); m/z: 397.54 |
| 1-408 | 2-Me-Bn | H | Ph | 0 | Me | ¹H NMR(200 MHz, CDCl₃) δ 7.60-7.55(m, 2H), 7.44-7.20(m, 7H), 6.57(d, 1H, J=2.8 Hz), 6.37(d, 1H, J=2.8 Hz), 6.31(d, 1H, J=9.8 Hz), 5.65(d, 1H, J=9.8 Hz), 4.26(s, 2H), 2.39(s, 3H), 1.42(s, 6H); m/z: 355.77 |
| 1-409 | 3-Me-Bn | H | Ph | 0 | Me | m/z: 355.95 |
| 1-410 | 4-Me-Bn | H | Ph | 0 | Me | ¹H NMR(200 MHz, CDCl₃) δ 7.58-7.53(m, 2H), 7.43-7.26(m, 5H), 7.16(d, 2H, J=7.7 Hz), 6.57(d, 1H, J=2.8 Hz), 6.36(d, 1H, J=2.8 Hz), 6.31(d, 1H, J=9.8 Hz), 5.64(d, 1H, J=9.8 Hz), 4.62(s, 2H), 2.36(s, 3H), 1.451(s, 6H); m/z: 355.57 |

TABLE 1-continued (1)

| Compound No. | R¹ | R² | R³ | n | R⁴ | NMR & Mass analytic results |
|---|---|---|---|---|---|---|
| 1-411 | 2-F-Bn | H | Ph | 0 | Me | m/z: 359.74 |
| 1-412 | 3-F-Bn | H | Ph | 0 | Me | $^1$H NMR(200 MHz, CDCl$_3$) δ 7.57-7.51(m, 2H), 7.43-7.26(m, 4H), 7.18-7.09(m, 2H), 7.01-6.93(m, 1H), 6.53(d, 1H, J=2.8 Hz), 6.32(d, 1H, J=2.8 Hz), 6.28(d, 1H, J=9.8 Hz), 5.65(d, 1H, J=9.8 Hz), 4.32(s, 2H), 1.41(s, 6H); m/z: 359.55 |
| 1-413 | 4-F-Bn | H | Ph | 0 | Me | $^1$H NMR(200 MHz, CDCl$_3$) δ 7.57-7.52(m, 2H), 7.43-7.26(m, 5H), 7.08-6.99(m, 2H), 6.54(d, 1H, J=2.8 Hz), 6.34(d, 1H, J=2.8 Hz), 6.29(d, 1H, J=9.8 Hz), 5.65(d, 1H, J=9.8 Hz), 4.27(d, 2H), 1.40(s, 6H); m/z: 359.25 |
| 1-414 | 2-Cl-Bn | H | Ph | 0 | Me | $^1$H NMR(200 MHz, CDCl$_3$) δ 7.56-7.52(m, 2H), 7.48-7.29(m, 5H), 7.26-7.20(m, 2H), 6.55(d, 1H, J=2.8 Hz), 6.33(d, 1H, J=2.8 Hz), 6.29(d, 1H, J=9.8 Hz), 5.63(d, 1H, J=9.8 Hz), 4.41(s, 2H), 1.40(s, 6H); m/z: 375.04 |
| 1-415 | 3-Cl-Bn | H | Ph | 0 | Me | $^1$H NMR(200 MHz, CDCl$_3$) δ 7.57(m, 2H), 7.43-7.26(m, 7H), 6.53(d, 1H, J=2.9 Hz), 6.32(d, 1H, J=2.9 Hz), 5.29(d, 1H, J=9.8 Hz), 5.65(d, 1H, J=9.8 Hz), 4.29(s, 6H); m/z: 375.97 |
| 1-416 | 4-Cl-Bn | H | Ph | 0 | Me | m/z: 375.71 |
| 1-417 | 2-CN-Bn | H | Ph | 0 | Me | m/z: 366.62 |
| 1-418 | 3-CN-Bn | H | Ph | 0 | Me | m/z: 366.58 |
| 1-419 | 4-CN-Bn | H | Ph | 0 | Me | $^1$H NMR(200 MHz, CDCl$_3$) δ 7.64(d, 2H, J=8.5 Hz), 7.54-7.42(m, 4H), 7.41-7.26(m, 3H), 6.50(d, 1H, J=2.9 Hz), 6.29-6.45(m, 2H), 5.66(d, 1H, J=9.4 Hz), 4.40(s, 2H), 1.41(s, 6H); m/z: 366.54 |
| 1-420 | 2-NO$_2$-Bn | H | Ph | 0 | Me | m/z: 386.64 |
| 1-421 | 3-NO$_2$-Bn | H | Ph | 0 | Me | m/z: 386.74 |
| 1-422 | 4-NO$_2$-Bn | H | Ph | 0 | Me | m/z: 386.54 |
| 1-423 | 2-CF$_3$-Bn | H | Ph | 0 | Me | m/z: 409.65 |
| 1-424 | 3-CF$_3$-Bn | H | Ph | 0 | Me | m/z: 409.05 |
| 1-425 | 4-CF$_3$-Bn | H | Ph | 0 | Me | $^1$H NMR(200 MHz, CDCl$_3$ δ 7.63-7.48(m, 6H), 7.43-7.26(m, 3H), 6.53(d, 1H, J=2.8 Hz), 6.31(d, 1H, J=2.8 Hz), 6.28(d, 1H, J=9.8 Hz), 5.65(d, 1H, J=9.8 Hz), 4.38(s, 2H), 1.40(s, 6H); m/z: 409.12 |
| 1-426 | 4-EtO-Bn | H | Ph | 0 | Me | m/z: 385.84 |
| 1-427 | 2,5-Di-Me-Bn | H | Ph | 0 | Me | m/z: 369.74 |
| 1-428 | 2,6-Di-Me-Bn | H | Ph | 0 | Me | $^1$H NMR(200 MHz, CDCl$_3$) 7.60-7.56(m, 2H), 7.44-7.26(m, 4H), 7.12-7.01(m, 2H), 6.57(d, 1H, J=2.4 Hz), 6.37(d, 1H, J=2.8 Hz), 6.31(d, 1H, J=9.8 Hz), 5.65(d, 1H, J=9.8 Hz), 4.21(s, 2H), 2.34(s, 3H), 2.33(s, 3H), 1.41(s, 6H); m/z: 369.65 |
| 1-429 | 3,5-Di-MeO-Bn | H | Ph | 0 | Me | $^1$H NMR(200 MHz, CDCl$_3$) δ 7.55-7.42(m, 2H), 7.41-7.26(m, 5H), 6.60-6.56(m, 3H), 6.40-6.37(m, 2H), 6.29(d, 1H, J=9.8 Hz), 5.64(d, 1H, J=9.8 Hz), 4.24(s, 2H), 3.78(s, 6H), 1.40(s, 6H); m/z: 401.98 |
| 1-430 | pyridin-2-ylmethyl (2-pyridyl-CH₂–) | H | Ph | 0 | Me | m/z: 342.85 |
| 1-431 | pyridin-3-ylmethyl (3-pyridyl-CH₂–) | H | Ph | 0 | Me | m/z: 342.28 |

TABLE 1-continued
(1)
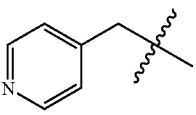
| Compound No. | R¹ | R² | R³ | n | R⁴ | NMR & Mass analytic results |
|---|---|---|---|---|---|---|
| 1-432 | 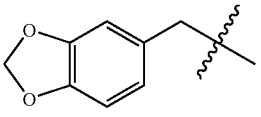 | H | Ph | 0 | Me | $^1$H NMR(200 MHz, CDCl$_3$) δ 8.59-8.56(m, 2H), 7.53-7.48(m, 2H), 7.41-7.26(m, 5H), 6.47(d, 1H, J=1.6 Hz), 6.28-6.23(m, 2H), 5.64(d, 1H, J=9.7 Hz), 4.37(s, 2H), 1.40(s, 6H); m/z: 342.64 |
| 1-433 | 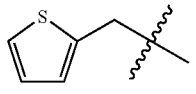 | H | Ph | 0 | Me | m/z: 385.42 |
| 1-434 | 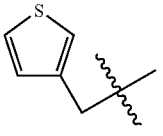 | H | Ph | 0 | Me | m/z: 347.55 |
| 1-435 | 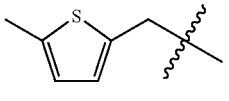 | H | Ph | 0 | Me | m/z: 347.24 |
| 1-436 | 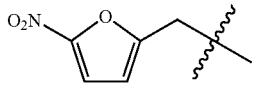 | H | Ph | 0 | Me | m/z: 361.01 |
| 1-437 | 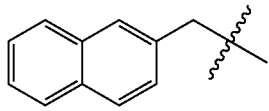 | H | Ph | 0 | Me | $^1$H NMR(200 MHz, CDCl$_3$) δ 7.52(d, 2H, J=6.5 Hz), 7.43-7.24(m, 5H), 6.53(d, 1H, J=2.8 Hz), 6.47(d, 1H, J=3.7 Hz), 6.32(d, 1H, J=2.8 Hz), 6.28(d, 1H, J=9.8 Hz), 5.66(d, 1H, J=9.8 Hz), 4.41(s, 2H), 4.40-3.80(br, 1H), 1.39(s, 6H); m/z: 376.41 |
| 1-438 | 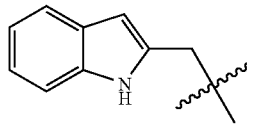 | H | Ph | 0 | Me | $^1$H NMR(200 MHz, CDCl$_3$) δ 7.85-7.82(m, 4H), 7.56-7.26(m, 8H), 6.63-6.60(m, 1H), 6.40-6.31(m, 1H), 6.28-6.27(d, 1H, J=9.8 Hz), 5.65(d, 1H, J=9.8 Hz), 4.47(s, 2H), 1.41(s, 6H); m/z: 391.77 |
| 1-439 |  | H | Ph | 0 | Me | m/z: 380.14 |

TABLE 1-continued

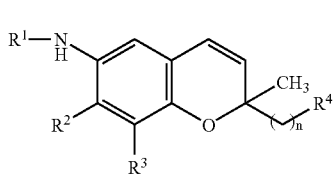

(1)

| Compound No. | R¹ | R² | R³ | n | R⁴ | NMR & Mass analytic results |
|---|---|---|---|---|---|---|
| 1-440 | PhEt | H | Ph | 0 | Me | m/z: 355.17 |
| 1-441 | 4-F-Bn | H | H | 2 | | m/z: 379.46 |
| 1-442 | 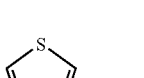 | H | H | 2 | | m/z: 369.42 |
| 1-443 | 2-F-Bn | H | H | 2 | | m/z: 363.87 |
| 1-444 | 4-MeO-Bn | H | H | 2 | | m/z: 375.50 |

Example III

Biological Examination Test (III-1) Biological Examination Using 5-LO (5-Lipoxygenase Enzyme Assay)

(III-1-1) 5-LO Enzyme Assay Using a FOX Reagent

Each test sample was added to lysates (7 μg) obtained from 5-LO expressing insect cells at a final concentration of 1 μM and reacted at room temperature for 3 min. Arachidonic acid as an enzyme substrate (40 μM) was added thereto and further reacted at room temperature for 4 min. Then, a FOX reagent (sulfuric acid 25 mM, xylenol orange 100 μM, FeSO₄ 100 μM; methanol: water=9:1) 100 μl was added thereto, and the absorbance of the reaction mixture was measured at 575 nm after 5 min.

(III-1-2) 5-LO-Enzyme Assay Using Spectroscopic Measureent (234 nm)

Each test sample was added to lysates (7 μg) obtained from 5-LO expressing insect cells at a final concentration of 1 μM and reacted at room temperature for 3 min. A reaction buffer solution (50 mM Tris buffer solution, pH 7.4, 0.4 mM CaCl₂, 24 μg/mL phosphatidylcholine, 40 μM arachidonic acid) was added thereto, and the absorbance of the reaction mixture was measured at 234 nm for 4 min.

(III-2) Measurement of Inhibitory Effect on LTB4 Synthesis Using RBL-1 Cells (LTB4 Cell-Based Assay)

RBL-1 (rat basophilic leukemia) cells were inoculated at a 24-well plate at a final concentration of 7.5×10⁵ cells/well and incubated for 2 hrs to adhere to the bottom of the well. After 2 hrs, the cells were treated with 10 μM (final conc.) A23187 for 10 min and reacted with each test sample (final conc. 10 μM) for 10 min. Then, the well plate was subjected to centrifugation at 1,500 g for 20 min to isolate a supernatant, and the supernatant was subjected to ELISA analysis to measure the amount of LTB4.

(III-3) Biological Examination Using an Animal Model (In vivo Assay: Mouse Ear Edema Model)

The inside of the right ear of ICR mouse (6 week old) was treated with 2 mg of arachidonic acid dissolved in 20 μl of acetone for 1 hr to induce an inflammation.

After 1 hr, the difference between the right ear treated with arachidonic acid and the nontreated left ear was measured with a microgauge. Further, to measure the amount of neutrophil penetrated into a tissue as a primary marker for inflammation induction, the myeloperoxidase (MPO) activity was measured. In particular, the tissue obtained from the arachidonic acid-treated right ear was homogenized in 50 mM phosphate buffer solution (pH 6.0) supplemented with 0.5% hexadecyltrimethylammonium bromide (HTAB), subjected to centrifugation, and then, the MPO activity of the supernatant was measured.

To measure in vivo activity of each test compound, each compound was dissolved in 0.5% methylcellulose (10 mL/kg) and orally administered to the mice 1 hr before the arachidonic acid treatment. After the arachidonic acid was treated for 1 hr, the ear thickness and MPO activity were measured, and in vivo activity of the test compound was estimated by comparing them with those of a control which was treated with arachidonic acid only without the test compound.

TABLE 2
| Test compound | 5-LO (% inhibition at 1 μM) | Cells (% inhibition at 1 μM) | Animal model (% inhibition) (Thickness (T) %, MPO % |
|---|---|---|---|
| Zileuton 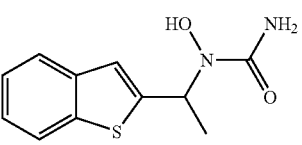 | 85 | 80 | Thickness 67% MPO 38% |
| 1-10 | 85 | 74 | |
| 1-11 | 84 | 72 | |
| 1-13 | 82 | 71 | |
| 1-16 | 78 | 69 | |
| 1-24 | 61 | 52 | |
| 1-34 | 78 | 55 | |
| 1-35 | 81 | 58 | |
| 1-39 | 60 | 40 | |
| 1-47 | 41 | | |
| 1-51 | 47 | | |
| 1-70 | 52 | 48 | |
| 1-75 | 62 | 67 | T: 25, MPO: 43 |
| 1-81 | 61 | 85 | |
| 1-86 | 35 | | |
| 1-88 | 71 | 78 | |
| 1-91 | 37 | | |
| 1-93 | 38 | | |
| 1-94 | 90 | 98 | T: 40, MPO: 51 |
| 1-95 | 92 | 99 | |
| 1-96 | 90 | 98 | |
| 1-104 | 72 | 64 | |
| 1-108 | 62 | 55 | |
| 1-112 | 76 | 81 | |
| 1-115 | 78 | 72 | |
| 1-124 | 84 | 98 | |
| 1-131 | 96 | 97 | T: 40, MPO: 78 |
| 1-137 | 38 | | |
| 1-143 | 40 | | |
| 1-151 | 86 | 90 | |
| 1-154 | 82 | 98 | |
| 1-155 | 84 | 100 | |
| 1-158 | 55 | 61 | |
| 1-161 | 72 | 68 | |
| 1-162 | 74 | 84 | |
| 1-170 | 80 | 92 | |
| 1-171 | 80 | 94 | |
| 1-173 | 81 | 95 | |
| 1-175 | 54 | 76 | |
| 1-179 | 52 | 58 | |
| 1-180 | 45 | | |
| 1-184 | 47 | | |
| 1-187 | 52 | 61 | |
| 1-190 | 87 | 93 | |
| 1-194 | 58 | 90 | |
| 1-195 | 89 | 97 | |
| 1-198 | 47 | | |
| 1-202 | 43 | | |
| 1-210 | 53 | 49 | |
| 1-217 | 37 | | |
| 1-220 | 24 | | |
| 1-231 | 46 | | |

TABLE 2-continued

| Test compound | 5-LO (% inhibition at 1 μM) | Cells (% inhibition at 1 μM) | Animal model (% inhibition) (Thickness (T) %, MPO % |
|---|---|---|---|
| 1-234 | 31 | | |
| 1-237 | 34 | | |
| 1-245 | 27 | | |
| 1-249 | 14 | | |
| 1-270 | 55 | 62 | |
| 1-275 | 83 | 95 | T: 54, MPO: 59 |
| 1-282 | 20 | | |
| 1-293 | 34 | | |
| 1-307 | 24 | | |
| 1-312 | 36 | 97 | |
| 1-314 | 80 | 98 | |
| 1-315 | 75 | 49 | |
| 1-324 | 51 | | |
| 1-337 | 42 | 89 | |
| 1-351 | 70 | 98 | T: 58, MPO: 75 |
| 1-356 | 81 | 82 | |
| 1-359 | 68 | | |
| 1-369 | 21 | | |
| 1-385 | 36 | | |
| 1-395 | 56 | 41 | |
| 1-404 | 72 | 91 | |
| 1-412 | 52 | 38 | |
| 1-423 | 44 | | |
| 1-432 | 66 | 62 | |
| 1-440 | 48 | | |

As shown in Table 2, it has been found that the inventive compounds are capable of effectively inhibiting the 5-LO activity, and some of them show a powerful inhibitory effect that is competitive with Zileuton used as a reference drug in enzyme, cell and animal experiments. Since the inventive compounds have potent inhibition actvitics of 5-LO with a unique structure entirely different 50000 that of Zileuton, they can be effectively used to develop a new drug for preventing or treating chronic inflammation, rheumatic arthritis, colitis, asthma, psoriasis and so on.

The following Formulation Examples are intended to further illustrate several formulating methods comprising the inventive compound as an effective ingredient and are not intended to limit the scope of the invention.

Formulation Example

Formulation 1: Tablet (Direct Pressurization)

After an effective ingredient 5.0 mg was sieved, it was mixed with lactose 14.1 mg, crosspovidone USNF 0.8 mg and magnesium stearate 0.1 mg and the mixture was subjected to direct pressurization, to obtain a tablet.

Formulation 2: Tablet (Wetting Assembly)

After an effective ingredient 5.0 mg was sieved, it was mixed with lactose 16.0 mg and starch 4.0 mg. Polysorbate 80 0.3 mg was dissolved in pure water, added to the mixture in a sutable amount, and then, the reaction mixture was subjected to microparticulation. After the microparticles were dried and sieved, they mixed with colloid silicon dioxide 2.7 mg and magnesium stearate 2.0 mg. The microparticles were subjected to pressurization, to obtain a tablet.

Formulation 3: Powder and Capsule

After an effective ingredient 5.0 mg was sieved, it was mixed with lactose 14.8 mg, polyvinyl pyrrolidone 10.0 mg and magnesium stearate 0.2 mg. The mixture was filled into a hard gelatin capsule No. 5 using a proper equipment.

Formulation 4: Injection

An effective ingredient 100 mg, mannitol 180 mg and $Na_2HPO_4 \cdot 12H_2O$ 26 mg were mixed in distillied water 2,974 mg, to obtain an injection.

While the embodiments of the subject invention have been described and illustrated, it is obvious that various changes and modifications can be made therein without departing from the spirit of the present invention which should be limited only by the scope of the appended claims.

What is claimed is:

1. 6-alkylamino-2,2-disubstituted-7,8-disubstituted-2H-1-benzopyran compound of formula 1 or an isomer thereof:

[Formula 1]

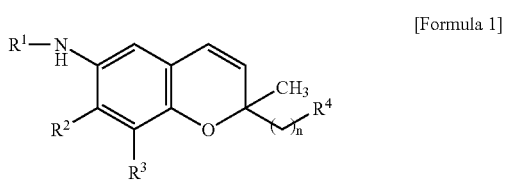

wherein $R_1$ is $C_1$~$C_{10}$ alkyl, benzyl or substituted benzyl, phenethyl, 2-pyridinylmethyl, 2-thiophenemethyl, 5-methyl-2-thiophenemethyl, 3-thiophenemethyl, indolylmethyl, benzodioxoranylmethyl, naphtalenylmethyl, or furanylmethyl;

$R^2$ and $R^3$ are hydrogen, $C_1$~$C_5$ alkyl, halogen, or phenyl and substituted phenyl, respectively;

$R^4$ and $R^4$ is $C_1$~$C_{10}$ alkyl, phenyl or substituted phenyl; and the phenyl or heterocycle is substituted with 1~4 substituents selected from the group consisting of $C_1$~$C_6$ alkyl, $C_1$~$C_6$ haloalkyl, halogen, nitro, cyano and $C_1$~$C_6$ alkoxy, n is an integer ranging from 1 to 5.

2. A method for preparing 6-alkylamino-2,2'-disubstituted-7,8-disubstituted-2H-1-benzopyran compound of formula 1 of claim 1, which comprises step 1 of synthesizing carbarnate resin in a form of 6-amino-2,2'-25 disubstituted-7,8-disubstituted-2H-1-benzopyran of formula 4 by incorporating 6-amino-2,2'-disubstituted-7,8-disubstituted-2H-1-benzopyran of formula 3 into the solid support coupled with a carbonate linker of formula 2;

step 2 of synthesizing resin in a form of 6-alkylamino-2,2'-disubstituted-7,8-disubstituted-2H-1-benzopran of formula 5 by selectively incorporating $R^1$ substitutent into a nitrogen atom of the benzopyran coupled with the carbamate linker of formula 4; and step 3 of synthesizing 6-alkylamino-2,2'-disubstituted-7,8-disubstituted-2H-1-benzopyran compound of formula 1 by deprotecting the compound of formula 5 with a dichioromethane solution containing trifluoroacetate (TFA) or an organic solvent containing an organic acid:

3. Carbamate resin in a form of 6-amino-2,2'-disubstituted-7,8-disubstituted-2H-1-benzopyran of formula 4:

[Formula 4]

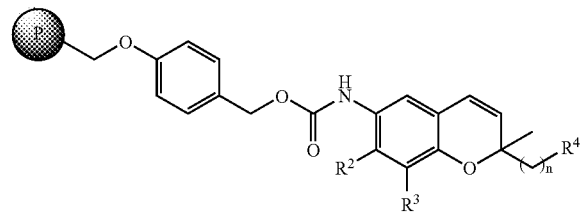

wherein $R^2$, $R^3$, $R^4$ and n are the same as described in claim 1,

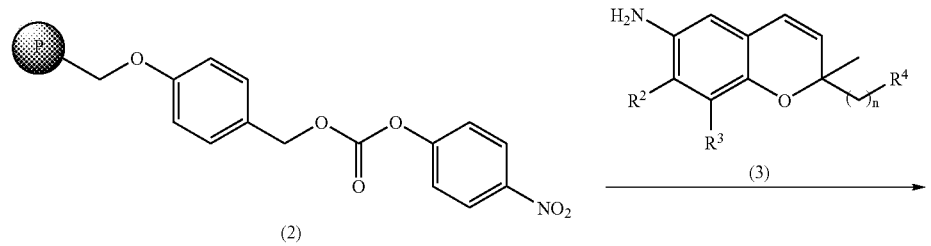

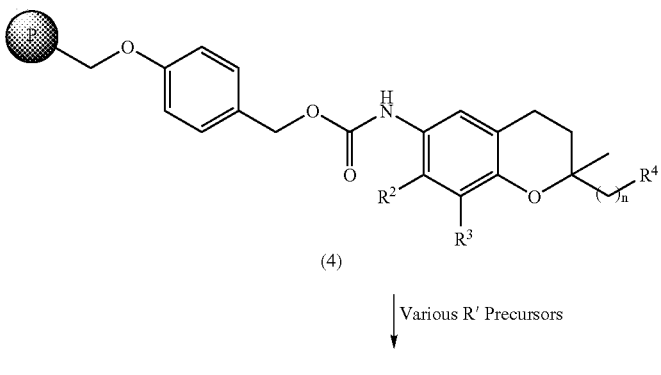

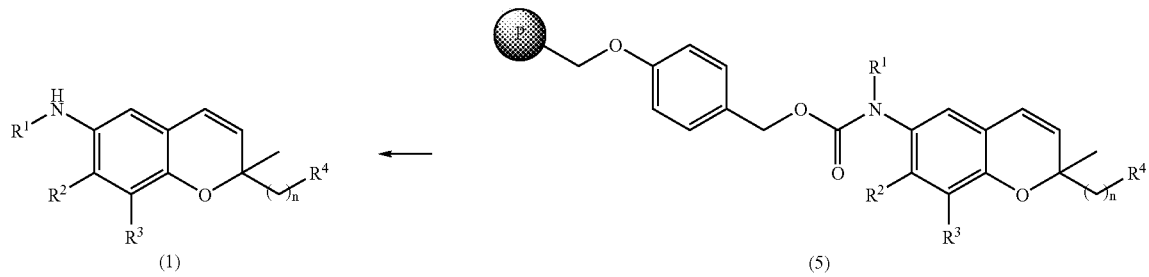

wherein $R^1$, $R^2$, $R^3$, $R^4$ and n are the same as described in claim 1;

ⓟ is a solid supporter in a form of high molecular weight polymer 10 selected from the group consisting of polystyrene-divinylbenzen, methacrylic acid-dimethylacrylamide and hydroxyl methacrylic acid.

ⓟ is a solid supporter in a form of high molecular weight polymer selected from the group consisting of polystyrene-dlvinylbenzen, methacrylic acid-dimethylacrylamide and hydroxyl methacrylic acid.

* * * * *